(12) United States Patent
Gambhir et al.

(10) Patent No.: US 8,178,654 B2
(45) Date of Patent: May 15, 2012

(54) ESTROGEN RECEPTOR INTRAMOLECULAR FOLDING SYSTEMS, ESTROGEN RECEPTOR INTRAMOLECULAR FOLDING SENSORS, METHODS OF USE THEREOF, METHODS OF DETECTING ER LIGANDS, AND METHODS OF DETECTING ER AGONISTS AND ANTAGONISTS

(75) Inventors: Sanjiv S. Gambhir, Portola Valley, CA (US); Ramasamy Paulmurugan, Mountain View, CA (US)

(73) Assignee: Stanford University, Palo Alto, CA (US)

( * ) Notice: Subject to any disclaimer, the term of this patent is extended or adjusted under 35 U.S.C. 154(b) by 1114 days.

(21) Appl. No.: 11/805,460

(22) Filed: May 23, 2007

(65) Prior Publication Data
US 2009/0044286 A1 Feb. 12, 2009

Related U.S. Application Data

(60) Provisional application No. 60/802,731, filed on May 23, 2006.

(51) Int. Cl.
*C07K 14/705* (2006.01)

(52) U.S. Cl. ......................................... 530/350
(58) Field of Classification Search .................. None
See application file for complete search history.

(56) References Cited

U.S. PATENT DOCUMENTS

| | | | |
|---|---|---|---|
| 6,270,964 B1 | 8/2001 | Michnick et al. | 435/6 |
| 6,294,330 B1 | 9/2001 | Michnick et al. | 435/6 |
| 6,428,951 B1 | 8/2002 | Michnick et al. | 435/4 |
| 6,828,099 B2 | 12/2004 | Michnick et al. | 435/6 |
| 6,872,871 B2 | 3/2005 | Brisson et al. | 800/288 |
| 6,897,017 B1 | 5/2005 | Michnick et al. | 435/6 |
| 6,929,916 B2 | 8/2005 | Michnick et al. | 435/6 |
| 7,062,219 B2 | 6/2006 | Michnick et al. | 434/4 |
| 7,160,691 B2 | 1/2007 | Michnick et al. | 435/8 |
| 2007/0022484 A1* | 1/2007 | Umezawa et al. | 800/14 |
| 2009/0113563 A1* | 4/2009 | Umezawa et al. | 800/14 |

* cited by examiner

*Primary Examiner* — Michael Pak
(74) *Attorney, Agent, or Firm* — Thomas, Kayden, Horstemeyer & Risley, LLP

(57) ABSTRACT

Briefly described, embodiments of this disclosure include estrogen receptor (ER) intramolecular folding systems, methods of detecting ER ligands and distinguishing between ER agonists and antagonists, cells including ER intramolecular folding systems, transgenic animals including ER intramolecular folding systems, fusion proteins, and the like.

20 Claims, 11 Drawing Sheets
(3 of 11 Drawing Sheet(s) Filed in Color)

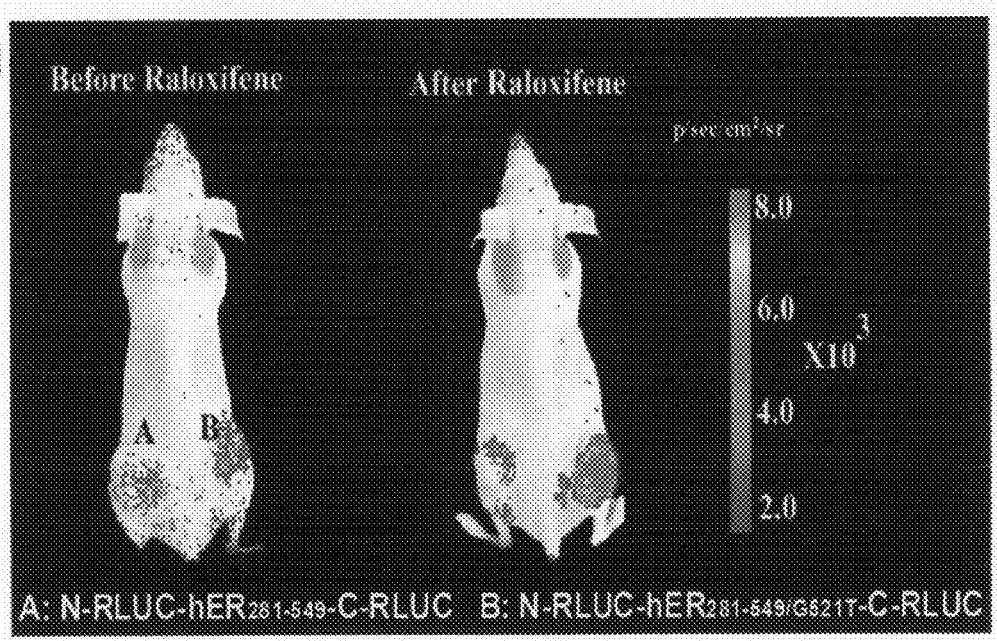
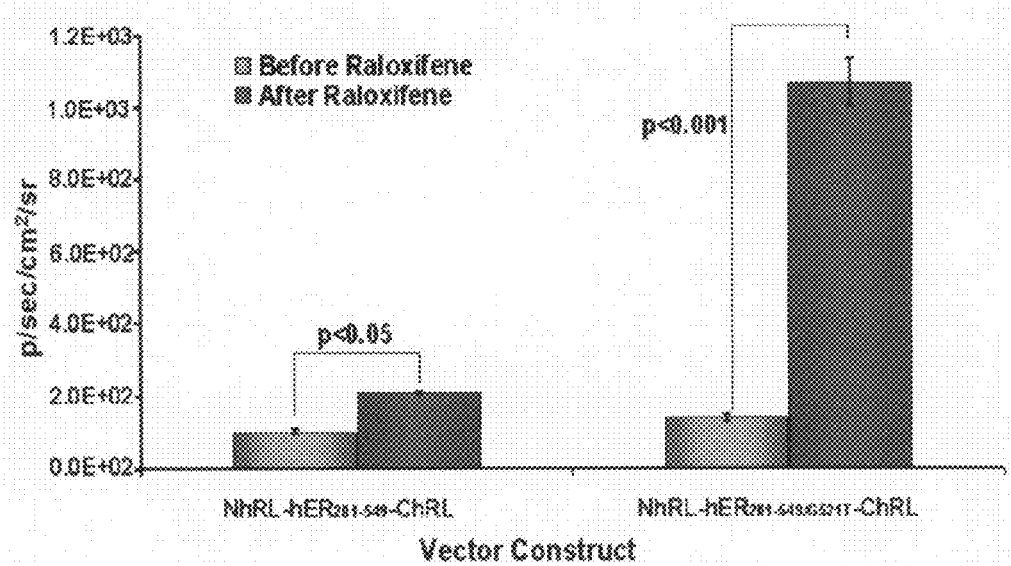
FIG. 5

Table 1

| Con | E2 | DES | OHT | Ral | Gen | ICI | 521 |
|---|---|---|---|---|---|---|---|
| 1.537182 | 100 | 92.14092 | 96.78062 | 80.95113 | 1.396585 | 7.002063 | G |
| 3.83679 | 6.002425 | 70.86455 | 84.1556 | 61.90189 | 2.682569 | 7.653152 | T |
| 1.846348 | 1.748077 | 1.765008 | 5.852995 | 2.310649 | 1.541783 | 1.958053 | Y |
| 2.531851 | 2.288014 | 2.332733 | 5.140625 | 1.866223 | 1.603432 | 1.640789 | F |
| 0.120722 | 0.146854 | 0.130476 | 0.101767 | 0.143357 | 0.133236 | 0.140045 | M |
| 1.315613 | 1.333647 | 1.967622 | 2.583194 | 2.174469 | 1.227648 | 1.250835 | N |
| 1.115023 | 1.523748 | 1.111526 | 8.180391 | 3.245509 | 1.130481 | 1.567362 | H |
| 2.733177 | 16.49531 | 28.69449 | 57.56675 | 61.54101 | 3.000569 | 0.161024 | C |
| 1.900636 | 3.042711 | 1.858678 | 2.790409 | 2.006636 | 1.988969 | 2.082271 | D |
| 1.881313 | 2.038105 | 2.255625 | 14.37881 | 2.548413 | 1.846532 | 2.670055 | Q |
| 1.391432 | 1.840091 | 1.647598 | 2.429531 | 1.843404 | 1.284512 | 1.862727 | R |
| 1.394376 | 2.412049 | 1.706671 | 4.342681 | 1.500008 | 1.342665 | 2.049698 | W |
| 10.53263 | 16.4747 | 20.83504 | 103.1782 | 271.3808 | 11.42756 | 22.88953 | V |
| 3.404509 | 68.59239 | 44.08747 | 62.80657 | 99.23573 | 3.14135 | 14.18852 | S |
| 5.731169 | 8.996369 | 33.62661 | 30.82792 | 48.41414 | 6.269817 | 11.28751 | I |
| 5.814717 | 129.0186 | 86.91932 | 121.8301 | 118.1085 | 7.758232 | 18.28387 | A |
| 1.279543 | 2.064421 | 3.309735 | 7.539055 | 5.168413 | 1.813407 | 1.867879 | L |
| 1.354995 | 1.51197 | 1.679435 | 1.955292 | 1.906709 | 1.575828 | 2.024487 | E |
| 1.111526 | 1.176856 | 1.347449 | 2.804211 | 2.330893 | 1.075457 | 1.586133 | P |
| 1.442224 | 2.069757 | 1.830338 | 7.907662 | 6.010891 | 1.416828 | 2.49026 | K |
|  |  |  |  |  |  |  |  |

FIG. 11

ESTROGEN RECEPTOR INTRAMOLECULAR FOLDING SYSTEMS, ESTROGEN RECEPTOR INTRAMOLECULAR FOLDING SENSORS, METHODS OF USE THEREOF, METHODS OF DETECTING ER LIGANDS, AND METHODS OF DETECTING ER AGONISTS AND ANTAGONISTS

CROSS-REFERENCE TO RELATED APPLICATION

This application claims priority to U.S. provisional applications entitled, "Estrogen receptor intramolecular folding systems, estrogen receptor intramolecular folding sensors, methods of use thereof, methods of detecting ER ligand, and methods of detecting ER agonists and antagonists," having Ser. No. 60/802,731, filed on May 23, 2006, which is entirely incorporated herein by reference.

FEDERALLY-SPONSORED RESEARCH OR DEVELOPMENT

This invention was made with Government support under contracts CA114747 and CA082214 awarded by the National Institutes of Health. The Government has certain rights in this invention.

BACKGROUND

Estrogens are responsible for the growth, development and maintenance of many reproductive cells. The physiological effects of these hormones are mediated by a ligand-inducible nuclear transcription factor, the estrogen receptor (ER). In the classical pathway of steroid hormone action, 17β-estradiol binds to the ligand binding domain (LBD) of an estrogen receptor and induces homodimerization, which then binds to a specific regulatory sequence of promoters of ER target genes, the estrogen response elements (ERE). The binding of hormones and a variety of other chemicals to the LBD of ER leads to a series of downstream molecular events. This includes the activation or repression of many downstream target genes through direct interaction with the transcription machinery.

Abnormal levels of estrogen have been linked with many diseases and disorders including cancer. The deficiency in the level of estrogen in post menopausal women can lead to reduced bone densities. Similarly, the presence of excess hormones has been reported to induce the development of different types of cancers including breast cancer. Most of these cancers respond to hormonal therapy (anti-estrogens) via the estrogen receptor. Hence, estrogen receptors are a major cellular therapeutic target.

The ER-LBD is folded into a three-layered, anti-parallel, α-helical sandwich composed of a central core layer of three helices that includes H5/6, H9, and H10. This is in turn sandwiched between two additional layers of helices (H1-4 and H7, H8, H11). This helical arrangement creates a "wedge shaped" molecular scaffold that maintains a sizeable ligand binding property at the narrower end of the domain. The remaining secondary structural elements, a small two-stranded, anti-parallel β-sheet (S1 and S2) and an α-helical H12, are located at this ligand binding portion of the molecule and flank the three-layered motif. The helix 12 (H12) is mainly located in the pocket of the ligand binding region. Therefore, it is a key element of the receptor in developing conformational modifications in response to various ligands.

The crystal structures of the LBD complexed with 17β-estradiol and Raloxifene show that although both ligands bind at the same site within the core of the LBD, each of these ligands induces a different conformational change on H12. In addition, the binding of ligands to the ligand-binding domain of ERα causes a conformational shift of helix 12 into an adjacent co-activator site that either prevents or enhances ERα from binding to a co-activator (NR box peptide), which would then activate a specific DNA sequence, the estrogen response element (ERE). This process controls many genes that are responsible for cell growth. Hence, helix 12 is one of the major portions of ER that plays a critical role in the ligand-induced proliferative effect of cells, and it is therefore important to develop an assay based on the movement of helix 12 in response to different ligands.

To date, several assays have been developed for screening ER ligands by using either purified ER protein or ER from cell lysates. Very few fluorescence resonance energy transfer (FRET) based assays have been used to study ER ligands in intact cells. FRET measures either ligand induced conformational changes while using the full length ER or the recruitment of co-activator peptides (LXXLL) by ER in response to ligand binding. For example, FRET measuring ligand induced conformational change with full length ER was used to study the phosphorylation mediated arrest induced by tamoxifen in breast cancer cells. FRET is a semi-quantitative assay and does not currently translate to imaging living animals. Some assays have been designed to study the effects of chemical agonists and antagonists of ER through their downstream target gene activations.

SUMMARY

Briefly described, embodiments of this disclosure include estrogen receptor (ER) intramolecular folding systems, methods of detecting ER ligands and detecting and/or distinguishing between ER agonists and antagonists, cells including ER intramolecular folding systems, transgenic animals including ER intramolecular folding systems, fusion proteins, and the like.

One exemplary estrogen receptor (ER) intramolecular folding system, among others, includes: a first split protein fragment, an ER ligand binding domain, and a second split protein fragment; wherein the first split protein fragment is attached to a first portion of the ER ligand binding domain, and wherein the second split protein fragment is attached to a second portion of the ER ligand binding domain; and wherein the first split protein fragment and the second split protein fragment are not bioluminescent, and wherein the first split protein fragment and the second split protein fragment are adapted to substantially complement to form a bioluminescent protein.

One exemplary method of detecting an ER ligand, among others, includes: providing an ER intramolecular folding system of the present disclosure; introducing a ligand to the system; and detecting a bioluminescent signal in the presence of a bioluminescence initiating compound.

One exemplary cell, among others, includes: an ER intramolecular folding system comprising: a first split protein fragment, an ER ligand binding domain, and a second split protein fragment; wherein the first split protein fragment is attached to a first portion of the ER ligand binding domain, and wherein the second split protein fragment is attached to a second portion of the ER ligand binding domain; and wherein the first split protein fragment and the second split protein fragment are not bioluminescent, and wherein the first split protein fragment and the second split protein fragment are adapted to substantially complement to form a bioluminescent protein.

One exemplary transgenic animal, among others, includes: an ER intramolecular folding system comprising: a first split protein fragment, an ER ligand binding domain, and a second split protein fragment; wherein the first split protein fragment is attached to a first portion of the ER ligand binding domain, and wherein the second split protein fragment is attached to a second portion of the ER ligand binding domain; and wherein the first split protein fragment and the second split protein fragment are not bioluminescent, and wherein the first split protein fragment and the second split protein fragment are adapted to substantially complement to form a bioluminescent protein.

One exemplary fusion protein, among others, includes: a first split protein fragment, an ER ligand binding domain, and a second split protein fragment, wherein the first split protein fragment is attached to a first portion of the ER ligand binding domain, wherein the second split protein fragment is attached to a second portion of the ER ligand binding domain, wherein the first split protein fragment and the second split protein fragment are not bioluminescent, and wherein the first split protein fragment and the second split protein fragment are adapted to substantially complement to form a bioluminescent protein.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

The patent or application file contains at least one drawing executed in color. Copies of this patent or patent application publication with color drawing(s) will be provided by the Office upon request and payment of the necessary fee.

FIG. 5A illustrates imaging of estrogen receptor ligand-induced intramolecular folding using a xenograft mouse model. The 293T cells stably expressing the fusion protein N-RLUC-hER$_{281-549(Seq\ ID\ No.\ 1)}$-C-RLUC and N-RLUC-mutant-hER$_{281-549/G521T(Seq\ ID\ No.\ 12)}$-C-RLUC were imaged immediately and 18 hours after injecting 0.5 mg of the ligand antagonist Raloxifene (i.p.). The site implanted with the cells expressing the fusion protein containing the mutant form of the ER showed a higher RLUC complementation signal. FIG. 5B illustrates the average photons measured (n=3) from the image of mice at site A and B. The error bars represent SEM of triplicate determinations.

FIG. 11 is Table 1, which illustrates 293T cells expressing fusion protein N-RLUC-hER$_{281-595(Seq\ ID\ No.\ 2)}$-C-RLUC with 20 different single amino acid mutations generated at position 521 studied for RLUC complementation using different ligands. The results identified that the fusion protein containing mutation G521T showed 95% reduction, specifically to endogenous ligand 17β-estradiol, without significantly affecting the other ligands RLUC complementation. The complementation induced by agonist 17β-estradiol (100%) was used as a control for comparison.

DETAILED DESCRIPTION

Figure 1:
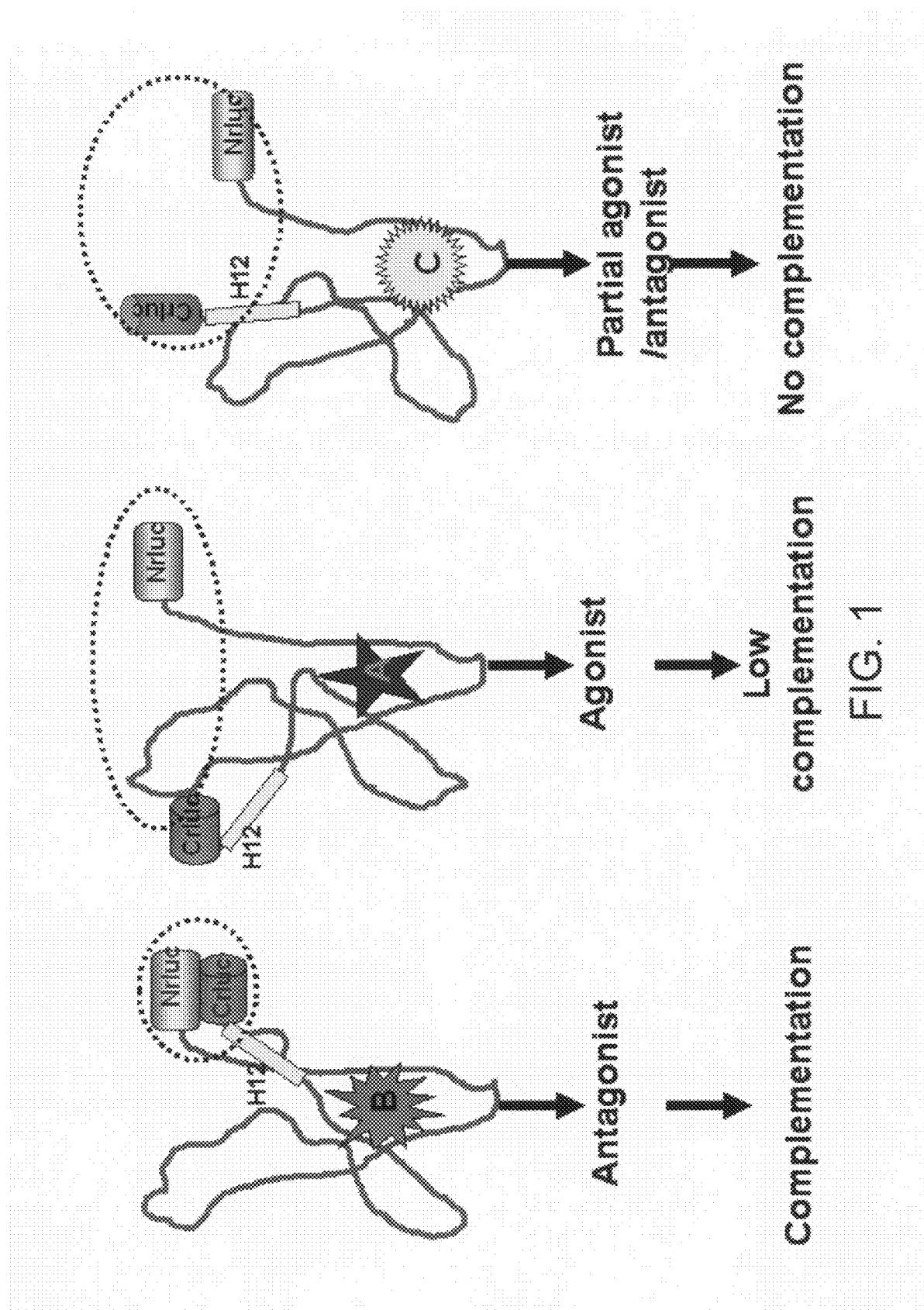
FIG. 1 illustrates a schematic representation of a strategy showing the hypothetical model of ligand-induced intramolecular folding of an estrogen receptor leading to split RLUC (*Renilla* Luciferase) complementation. In this strategy N- and C-terminal fragments of split RLUC (N-RLUC: SEQ ID No. 36 (nucleotide sequence) and SEQ ID No. 37 (amino acid sequence); C-RLUC: SEQ ID No. 38 (nucleotide sequence) and SEQ ID No. 39 (amino acid sequence)) are respectively fused to the N- and C-terminus of the human estrogen receptor to produce the fusion protein N-RLUC-hER-C-RLUC. The human estrogen receptor sequence may have varying lengths (e.g., amino acids 355-549, 355-595, 281-549 and 281-595, of SEQ. ID No. 3). The cells expressing the fusion protein N-RLUC-hER-C-RLUC bind to ER ligands that potentially induce folding of the ligand-binding domain, based on the type of ligand. This folding leads to split RLUC complementation if the ligand is an antagonist (B) and leads to low or no complementation if the ligand is an agonist (A) or partial agonist/antagonist (C), respectively. Even though the distance between the N- and C-RLUC fragments after binding with partial agonist in the model is closer than with the one binding with agonists, this model indicates the importance of the orientations of the RLUC fragments for generating complementation.

Embodiments of the present disclosure will employ, unless otherwise indicated, techniques of synthetic organic chemistry, biochemistry, molecular biology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

In describing and claiming the disclosed subject matter, the following terminology will be used in accordance with the definitions set forth below.

The term "complementing fragments" or "complementary fragments" when used in reference to split protein fragments refers to fragments of a bioluminescent protein that are individually inactive (e.g., do not express the reporter phenotype), wherein binding of the complementing fragments restores reporter activity. The terms "complementing" or "complementation" refer to when the fragments bind together. The terms "self-complementing", "self-assembling", and "spontaneously-associating", when used to describe two fragments of the same protein, indicates that the fragments are capable of reconstituting into an active bioluminescent protein when the individual fragments are soluble and are sufficiently close to or in contact with one another.

A "bioluminescent initiator molecule" is a molecule that can react with a bioluminescent protein to generate bioluminescence.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall (homologous) and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of this disclosure and still result in a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biologically functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take one or more of the foregoing characteristics into consideration are well known to those of skill in the art and include, but are not limited to (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Iie: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also refers to the degree of sequence relatedness between polypeptide as determined by the match between strings of such sequences. "Identity" and "similarity" can be readily calculated by known methods, including, but not limited to, those described in Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073, (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present invention.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution (including conservative and non-conservative substitution), or insertion, and wherein said alterations may occur at the amino- or carboxy-terminus positions of the reference polypeptide sequence or anywhere between those terminal positions, interspersed either individually among the amino acids in the reference sequence, or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

Conservative amino acid variants can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenyl-alanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. (Robertson, et al., *J. Am. Chem. Soc.*, 113: 2722, 1991; Ellman, et al., *Methods Enzymol.*, 202: 301, 1991; Chung, et al., *Science*, 259: 806-9, 1993; and Chung, et al., *Proc. Natl. Acad. Sci. USA*, 90: 10145-9, 1993). In a second method, translation is carried out in *Xenopus* oocytes by microinjection of mutated mRNA and chemically aminoacylated suppressor tRNAs (Turcatti, et al., *J. Biol. Chem.*, 271: 19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. (Koide, et al., *Biochem.*, 33: 7470-6, 1994). Naturally occurring amino acid residues can be converted to non-naturally occurring species by in vitro chemical modification. Chemical modification can be combined with site-directed mutagenesis to further expand the range of substitutions (Wynn, et al., *Protein Sci.*, 2: 395-403, 1993).

As used herein, the term "polynucleotide" generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid," "nucleic acid sequence," or "oligonucleotide" also encompass a polynucleotide as defined above.

In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically, or metabolically modified forms of polynucleotides, as well as the chemical forms of DNA and RNA characteristic of viruses and cells, including simple and complex cells, inter alia.

By way of example, a polynucleotide sequence of the present disclosure may be identical to the reference sequence, that is be 100% identical, or it may include up to a certain integer number of nucleotide alterations as compared to the reference sequence. Such alterations are selected from the group including at least one nucleotide deletion, substitution, including transition and transversion, or insertion, and wherein said alterations may occur at the 5' or 3' terminus positions of the reference nucleotide sequence or anywhere between those terminus positions, interspersed either individually among the nucleotides in the reference sequence or in one or more contiguous groups within the reference sequence. The number of nucleotide alterations is determined by multiplying the total number of nucleotides in the reference nucleotide by the numerical percent of the respective percent identity (divided by 100) and subtracting that product from said total number of nucleotides in the reference nucleotide. Alterations of a polynucleotide sequence encoding the polypeptide may alter the polypeptide encoded by the polynucleotide following such alterations.

The term "codon" means a specific triplet of mononucleotides in the DNA chain or mRNA that make up an amino acid or termination signal.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (e.g., GAU and GAC triplets each encode Asp).

"Operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will direct the linked protein to be localized at the specific organelle.

As used herein, the term "exogenous DNA" or "exogenous nucleic acid sequence" or "exogenous polynucleotide" refers to a nucleic acid sequence that was introduced into a cell or organelle from an external source. Typically the introduced exogenous sequence is a recombinant sequence.

As used herein, the term "transfection" refers to the introduction of a nucleic acid sequence into the interior of a membrane enclosed space of a living cell, including introduction of the nucleic acid sequence into the cytosol of a cell as well as the interior space of a mitochondria, nucleus or chloroplast. The nucleic acid may be in the form of naked DNA or RNA, associated with various proteins, or the nucleic acid may be incorporated into a vector.

As used herein, the term "vector" or "expression vector" is used to denote a DNA molecule, linear or circular, which includes a segment encoding a polypeptide of interest operably linked to additional segments that provide for its transcription and translation upon introduction into a host cell or host cell organelles. Such additional segments include promoter and terminator sequences, and may also include one or more origins of replication, one or more selectable markers, an enhancer, a polyadenylation signal, etc. Expression vectors are generally derived from yeast or bacterial genome or plasmid DNA, animal virus genome, or viral DNA, or may contain elements of both.

"DNA regulatory sequences", as used herein, are transcriptional and translational control sequences, such as promoters, enhancers, polyadenylation signals, termination signals, and the like, that provide for and/or regulate expression of a coding sequence in a host cell.

A "promoter sequence" is a DNA regulatory region in an operon capable of binding RNA polymerase in a cell and initiating transcription of a downstream (3' direction) coding sequence. For purposes of defining the present invention, the promoter sequence is bound at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present disclosure.

As used herein, the term "hybridization" refers to the process of association of two nucleic acid strands to form an antiparallel duplex stabilized by means of hydrogen bonding between residues of the opposite nucleic acid strands.

"Hybridizing" and "binding", with respect to polynucleotides, are used interchangeably. The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions.

The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

"Stringent hybridization conditions" and "stringent hybridization wash conditions" in the context of nucleic acid hybridization (e.g., as in array, Southern or Northern hybridizations) are sequence dependent, and are different under different experimental parameters. Stringent hybridization conditions that can be used to identify nucleic acids within the scope of the disclosure can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions sets forth the conditions that determine whether a nucleic acid will specifically hybridize to a surface bound nucleic acid. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, substantially similar conditions. Stringent conditions for washing can also be, e.g., 0.2×SSC/0.1% SDS at 42° C.

A specific example of stringent assay conditions is a rotating hybridization at 65° C. in a salt based hybridization buffer with a total monovalent cation concentration of 1.5 M (e.g., as described in U.S. patent application Ser. No. 09/655,482 filed on Sep. 5, 2000, the disclosure of which is herein incorporated by reference) followed by washes of 0.5×SSC and 0.1× SSC at room temperature. Stringent assay conditions are hybridization conditions that are at least as stringent as the above representative conditions, where a given set of conditions are considered to be "at least as stringent" if substantially no additional binding complexes that lack sufficient complementarity to provide for the desired specificity are produced in the given set of conditions as compared to the above specific conditions, where by "substantially no more" is meant less than about 5-fold more, typically less than about 3-fold more.

By "administration" is meant introducing a sensor of the present disclosure into a subject. The preferred route of administration of the sensor is intravenous. However, any route of administration, such as oral, topical, subcutaneous, peritoneal, intraarterial, inhalation, vaginal, rectal, nasal, introduction into the cerebrospinal fluid, or instillation into body compartments can be used.

In accordance with the present disclosure, "a detectably effective amount" of the sensor of the present disclosure is defined as an amount sufficient to yield an acceptable image using equipment that is available for clinical use. A detectably effective amount of the sensor of the present disclosure may be administered in more than one injection. The detectably effective amount of the sensor of the present disclosure can vary according to factors such as the degree of susceptibility of the individual, the age, sex, and weight of the individual, idiosyncratic responses of the individual, the dosimetry, and the like. Detectably effective amounts of the sensor of the present disclosure can also vary according to instrument and film-related factors. Optimization of such factors is well within the level of skill in the art.

As used herein, the term "organelle" refers to cellular membrane-bound structures such as the chloroplast, mitochondrion, and nucleus. The term "organelle" includes natural and synthetic organelles.

As used herein, the term "non-nuclear organelle" refers to any cellular membrane bound structure present in a cell, except the nucleus.

As used herein, the term "host" or "organism" includes humans, mammals (e.g., cats, dogs, horses, etc.), living cells, and other living organisms. A living organism can be as simple as, for example, a single eukaryotic cell or as complex as a mammal.

General Discussion

The present disclosure includes estrogen receptor (ER) intramolecular folding systems, ER intramolecular folding sensors, methods of producing ER intramolecular folding systems and sensors, methods of using ER intramolecular folding systems and sensors, methods of using ER intramolecular folding sensors for detecting ER ligands, methods of using ER intramolecular folding sensors for detecting ER agonists and/or antagonists, methods of detecting ER ligands, methods of detecting/distinguishing ER agonists and/or antagonists, methods of screening ER related molecules (e.g., drugs), and the like.

In general, systems, sensors, and methods of the present disclosure include a first split protein fragment, an ER ligand binding domain (LBD), and a second split protein fragment. The first split protein fragment is attached to the N-terminus (amino terminus) of the ER ligand binding domain, while the second split protein fragment is attached to the C-terminus (carboxy terminus) of the ER ligand binding domain. The first split protein fragment and the second split protein fragment are not bioluminescent, while the first split protein fragment and the second split protein fragment can complement to form a bioluminescent protein. It should be noted that peptide linkers can be positioned between one or more of the first split protein fragment, the ER ligand binding domain, and/or the second split protein fragment.

The ER ligand binding domain can be designed to distinguish between different types of compounds and be used in different systems. For example, the ER ligand binding domain can be designed to distinguish between ER ligands and non-ER ligands and between/among ER agonists, ER antagonists, and/or Selective Estrogen Receptor Modulators (SERMs). In another example, the ER ligand binding domain can be designed to reduce interaction between the ER ligand binding domain and endogenous ER ligands (e.g., 17β-estradiol). Reducing the interaction with the endogenous ER ligands extends the ER intramolecular folding system's ability to be used in living hosts.

In an embodiment, the ER ligand binding domain has a folding arrangement in a three-dimensional space that substantially inhibits the interaction of the first split protein fragment and the second split protein fragment. The ER ligand binding domain can undergo a conformational change into one or more folding arrangements under the inducement of a compound (e.g., ER ligands, ER agonists, ER antagonists and/or SERMs). The conformational change can be detected and measured through the interaction of the first split protein fragment and the second split protein fragment. Thus, the systems, sensors, and methods of the present disclosure can be used to detect, measure, quantitate, image, and the like, interactions of compounds with the ER ligand binding domain, in vitro and in vivo.

In an embodiment, the ER ligand binding domain can be induced by an ER ligand to undergo a conformational change that substantially increases the possibility of interaction of the first split protein fragment and the second split protein fragment.

In another embodiment, the ER ligand binding domain can be induced by an ER agonist to undergo a conformational change that partially increases the possibility of interaction of the first split protein fragment and the second split protein fragment, while the ER ligand binding domain can be induced by an ER antagonist to undergo a conformational change that substantially increases the possibility of interaction of the first split protein fragment and the second split protein fragment. The difference of the interaction of the first split protein fragment and the second split protein fragment when exposed to an agonist or an antagonist is detectable and statistically significant so that the ER intramolecular folding system can be used to distinguish between interactions of the agonist and the antagonist, as well as SERMs, with the ER ligand binding domain.

The first split protein fragment and the second split protein fragment can complement (e.g., self complement or spontaneously self complement) with one another to form a bioluminescent protein. The bioluminescent protein emits bioluminescent energy when exposed to a bioluminescence initiating compound. Although embodiments of the split protein fragments are not bioluminescent when separated, the split protein fragments can be induced to complement or are able to spontaneously self complement upon coming into sufficiently close contact with one another to form a bioluminescent protein (e.g., a Luciferase protein).

Thus, embodiments of the present disclosure can be used to detect, study, monitor, evaluate, and/or screen, biological events in vivo and/or in vitro, such as, but not limited to, ER related interactions with ER ligands and non-ER-ligands as well as between/among ER agonist, SERM, and/or ER antagonist. In addition, embodiments of the present disclosure can be used to screen molecules (e.g., drugs) related to the ER interactions with ER ligands and non-ER-ligands.

Embodiments of the present disclosure can be used to detect (and visualize) and/or quantitate ER related interactions events in in vitro as well as in in vivo studies, which can decrease time and expense since the same system can be used for cells and living organisms. Embodiments of the present disclosure can be used to test an event occurrence in a large number of samples, and has the capacity to transition from single cells to living animals without changing the ER intramolecular folding system/sensor and/or the imaging device.

Briefly described, embodiments of this disclosure, among others, include ER intramolecular folding sensors and systems, fusion proteins including ER intramolecular folding sensors and systems, vectors and other encoding schemes for encoding ER intramolecular folding sensors and systems, and methods of using the ER intramolecular folding sensors and systems, fusion proteins, vectors, and the like. Note that for each of the ER intramolecular folding sensors and systems, proteins, fusion proteins, protein fragments, and nucleotides, one skilled in the art would be able to determine the corresponding nucleotide sequence or protein sequence, respectively, and be able to introduce each into a system of interest.

ER Intramolecular Folding System for ER Ligands

In general, ER intramolecular folding sensors or systems can be used in vivo and/or in vitro. In an embodiment, the ER intramolecular folding sensors or systems can be introduced into a system (e.g., inside a cell or outside a cell and/or to a host), the ER intramolecular folding sensors or systems can be expressed (e.g., using a vector or other appropriate expression system) in the system, and/or the ER intramolecular folding sensors or systems can be included in a transgenic animal or plant. In an embodiment, the ER intramolecular folding sensors or systems can be introduced into a host or organism in vivo.

As mentioned above, an embodiment of the present disclosure includes an ER intramolecular folding system having a first split protein fragment (e.g., N-terminal fragment, N-RLUC (SEQ ID No. 37 (amino acid sequence))), an ER ligand binding domain (also known as "intramolecular folding domain"), and a second split protein fragment (e.g., C-terminal fragment, C-RLUC (SEQ ID No. 39 (amino acid sequence))). In this embodiment, the ER ligand binding domain is designed to distinguish between ER ligands and non-ER ligands and also to distinguish between agonist ER-ligands and antagonist ER-ligands.

The ER ligand binding domain can have a sequence selected from: SEQ. ID No. 1 (human estrogen receptor alpha, amino acids 281-549), SEQ. ID No. 2 (human estrogen receptor alpha, amino acids 281-595), SEQ. ID No. 3 (human estrogen receptor alpha, amino acids 1-595), SEQ. ID No. 4 (mouse estrogen receptor alpha, amino acids 281-549), SEQ. ID No.5 (mouse estrogen receptor alpha, amino acids 281-599), SEQ. ID No. 6 (mouse estrogen receptor amino acids 1-599), and SEQ. ID No. 40 (estrogen receptor beta).

It should be noted that peptide linkers can be positioned between one or more of the first split protein fragment, the ER ligand binding domain, and the second split protein fragment. In an embodiment, the GGGGSGGGGS (Seq. ID No. 15) and/or the GGGGSGGGGSGGGGS peptide linker (Seq. ID No. 16) can be used between the N-RLUC and ER-ligand binding domain and also between ER-ligand binding domain and C-RLUC fragment.

The first split protein fragment is attached to a N-terminus of the ER ligand binding domain (e.g., in front of starting amino acid (e.g., methionine)), while the second split protein fragment is attached to the C-terminus (e.g., in front of starting amino acid (e.g., methionine)) of the ER ligand binding domain. The first split protein fragment and the second split protein fragment are not bioluminescent. The first split protein fragment and the second split protein fragment are adapted to substantially complement to one another to form a bioluminescent protein. The bioluminescent protein emits a bioluminescent energy when it interacts with a bioluminescence initiating compound.

The ER ligand binding domain has a folding arrangement (e.g., a first conformational position) in a three-dimensional space that substantially inhibits the interaction of the first split protein fragment and the second split protein fragment. The ER ligand binding domain has a characteristic of changing from a first conformational position to a second conformational position upon binding with an ER ligand. Therefore, if the ER ligand binding domain undergoes a conformational change to the second conformation position, the first split protein fragment and the second split protein fragment can complement and emit a bioluminescent energy upon interaction with a bioluminescence initiating compound. Thus, the emission of bioluminescent energy can be detected and would indicate that the ligand introduced to the ER intramolecular folding system is an ER ligand.

For example, in the first conformational position, the first split protein fragment and the second protein fragment are proximally separated (e.g., separated in a three-dimensional space) so that the first split protein fragment and the second protein fragment do not substantially complement. In the second conformation position when an ER ligand binds, the first split protein fragment and the second protein fragment are proximally separated so that the first split protein fragment and the second protein fragment are able to substantially complement.

The phrase "do not substantially complement" does not mean that the first split protein fragment and the second protein fragment never complement, but rather that the first split protein fragment and the second protein fragment do not complement to a significant degree (to produce more than about 99% of the expected emission of the bioluminescent protein). The phrase "are able to substantially complement" does not mean that the first split protein fragment and the second protein fragment complement 100% of the time (e.g., to produce more than about 1% of the expected emission of the bioluminescent protein), but rather complement to a greater degree relative to when the first split protein fragment and the second protein fragment "do not substantially complement". In other words, there is a measurable and statistically significant difference (e.g., a statistically significant difference is enough of a difference to distinguish between these two states, such as about 0.1%, 1%, 3%, 5%, 10%, 15%, 20%, 25%, 30%, or 40% or more difference between the amount of energy emitted in each state, where the statistically significant difference is determined, at least in part, by the components of the ER intramolecular folding sensors or systems as well as the detection system) between when the first split protein fragment and the second protein fragment "do not substantially complement" and when the first split protein fragment and the second protein fragment "are able to substantially complement". The measurable difference (fold activation) can be used to distinguish between instances where a particular ligand interacts with the ER ligand binding domain and when the ligand does not interact with the ER ligand binding domain. Standards can be used to determine the relative amount of energy that is emitted. Additional details are described in the Example.

The ER intramolecular folding system or sensor can be used in methods of detecting an ER ligand (e.g., an agonist and an antagonist) using an ER intramolecular folding system having a ER ligand binding domain designed to distinguish between ER ligands and non-ER ligands. The ER intramolecular folding system or sensor is introduced to or is part of a cell or a host. A ligand is introduced to the ER intramolecular folding system. The ligand may interact with the ER ligand binding domain and may cause a conformational change. A bioluminescence initiating compound is introduced to the system (prior to and/or after the ligand). If a bioluminescent signal is detected, this indicates that a conformational change occurred and that the ligand is an ER ligand. If no bioluminescent signal is detected, a conformational change did not occur and the ligand is a non-ER ligand. Additional details are described in the Example.

The method can be conducted in vitro or in vivo. The ER intramolecular folding system or sensor can be introduced, incorporated into, or expressed in a part of a cell or a host as well as in a transgenic animal or a transgenic plant.

In another embodiment, the ER ligand binding domain can be designed to reduce interaction between the ER ligand binding domain and endogenous ER ligands. This mutation extends the ability to use the ER intramolecular folding system in living hosts.

In an embodiment, the ER ligand binding domain is designed to reduce the interaction between the ER ligand binding domain and 17β-estradiol. In an embodiment, the sequence of the ER ligand binding domain can be modified by changing the amino acid at a position 521 from glycine to threonine (Seq. ID No. 3), which reduced interaction of the ER ligand binding domain with 17β-estradiol by about 90%, while only reducing the interaction of the ER ligand binding domain with other ER ligands by about 10-20%. The change from glycine to threonine (Seq. ID Nos. 3, 11, and 12) was conducted by creating a mutation at 521 with all 20 amino acids and screened with more than 10 ER-ligands. Additional details are described in the Example. It should also be noted that the amino acid at position 521 could be changed from glycine to any one of the other amino acids (e.g., the other 19 amino acids (e.g., SEQ ID No. 11, 12, 13, and 14), which is described in more detail in the Example.

ER Intramolecular Folding System for Agonists and Antagonists

As mentioned above, an embodiment of the present disclosure includes an ER intramolecular folding system having a first split protein fragment, an ER ligand binding domain, and a second split protein fragment. In this embodiment, the ER ligand binding domain is designed to distinguish between ER agonists and ER antagonists. In an embodiment, the ER intramolecular folding system can be designed to distinguish between/among ER agonists, ER antagonists, and/or SERMs. The ER ligand binding domain can have a sequence selected from: SEQ. ID No. 1 (amino acids 281-549 for human ER ligand binding domain) and SEQ. ID No. 4 (amino acids 281-549 for mouse ER ligand binding domain).

It should be noted that peptide linkers can be positioned between one or more of the first split protein fragment, the ER ligand binding domain, and the second split protein fragment.

The first split protein fragment is attached to a first portion of the ER ligand binding domain, while the second split protein fragment is attached to a second portion of the ER ligand binding domain. The first split protein fragment and the second split protein fragment are not bioluminescent. The first split protein fragment and the second split protein fragment are adapted to substantially complement to form a bioluminescent protein. The bioluminescent protein emits a bioluminescent energy when it interacts with a bioluminescence initiating compound.

The ER ligand binding domain has a folding arrangement (e.g., a first conformational position) in a three-dimensional space that substantially inhibits the interaction of the first split protein fragment and the second split protein fragment. The ER ligand binding domain has a characteristic of changing from a first conformational position to a second conformational position upon interaction with an ER agonist. In addition, the ER ligand binding domain has a characteristic of changing from a first conformational position to a third conformational position upon interaction with an ER antagonist.

In the first conformational position the first split protein fragment and the second protein fragment are proximally separated so that the first split protein fragment and the second protein fragment do not substantially complement. In the second conformational position the first split protein fragment and the second protein fragment are proximally separated so that the first split protein fragment and the second protein fragment are able to partially complement. When the first split protein fragment and the second protein fragment partially complement in the presence of a bioluminescence initiating compound, a first amount of bioluminescent energy is emitted.

In the third conformation position the first split protein fragment and the second protein fragment are proximally separated so that the first split protein fragment and the second protein fragment are able to substantially complement. When the first split protein fragment and the second protein fragment substantially complement in the presence of a bioluminescence initiating compound, a second amount of bioluminescent energy is emitted. The first amount of bioluminescent energy and the second amount of bioluminescent energy are distinguishable. In an embodiment, the first amount of bioluminescent energy that is emitted is about 30 to 40% of the expected emission of the fully complemented bioluminescent protein (e.g., agonists interaction with the ER binding domain), while the second amount of bioluminescent energy is emitted is about 80 to 100% of the expected emission of the fully complemented bioluminescent protein (e.g., antagonists interaction with the ER binding domain).

The phrase "do not substantially complement" does not mean that the first split protein fragment and the second protein fragment never complement, but rather that the first split protein fragment and the second protein fragment do not complement to a significant degree. In an embodiment, the phrase "do not substantially complement" means that the first split protein and the second split protein complement to produce about 0 to 30% of the expected emission of the fully complemented bioluminescent protein.

The phrase "are able to partially complement" means that the first split protein fragment and the second protein fragment complement to a greater degree than when the first split protein fragment and the second protein fragment "do not substantially complement". There is a measurable and statistically significant difference (e.g., a statistically significant difference is enough of a difference to distinguish between these two states, such as about 0.1%, 1%, 3%, 5%, 10%, 15%, 20%, 25%, 30%, or 40% or more, difference between the amount of energy emitted in each state, where the statistically significant difference is determined, at least in part, by the components of the ER intramolecular folding sensors or systems as well as the detection system) between when the first split protein fragment and the second protein fragment "do not substantially complement" and when the first split protein fragment and the second protein fragment "are able to partially complement". In an embodiment, the phrase "are able to partially complement" means that the first split protein and the second split protein complement to produce about 30 to 40% of the expected emission of the fully complemented bioluminescent protein.

The phrase "are able to substantially complement" does not mean that the first split protein fragment and the second protein fragment complement 100% of the time, but rather complement to a greater degree relative to when the first split protein fragment and the second protein fragment "does not substantially complement" and when the first split protein fragment and the second protein fragment "are able to partially complement". In other words, there is a measurable and statistically significant difference (e.g., a statistically significant difference is enough of a difference to distinguish between these two states, such as about 0.1%, 1%, 3%, 5%, 10%, 15%, 20%, 25%, 30%, or 40% or more, difference between the amount of energy emitted in each state, where the statistically significant difference is determined, at least in part, by the components of the ER intramolecular folding sensors or systems as well as the detection system) between when the first split protein fragment and the second protein fragment "are able to partially complement" and when the first split protein fragment and the second protein fragment "are able to substantially complement". The measurable difference can be used to distinguish between instances where an agonist interacts with the ER ligand binding domain and when an antagonist interacts with the ER ligand binding domain. Standards can be used to determine the relative amount of energy that is emitted by an agonist and an antagonist. Additional details are described in the Example.

In an embodiment, the phrase "are able to substantially complement" means that the first split protein and the second split protein complement about 80 to 100% of the expected emission of the fully complemented bioluminescent protein. In an embodiment, a 2 to 3 fold difference in the signal between antagonists (e.g., about 80 to 100% of the expected emission of the fully complemented bioluminescent protein) and agonists (e.g., about 30 to 40% of the expected emission of the fully complemented bioluminescent protein) exists, thus distinguishing between "able to partially complement" and "are able to substantially complement".

The ER intramolecular folding system or sensor can be used in methods of detecting an agonist and an antagonist using an ER intramolecular folding system having a ER ligand binding domain designed to distinguish between ER agonists and ER antagonists. The ER intramolecular folding system or sensor is introduced to a cell or host or part of a cell or a host. A ligand is introduced to the ER intramolecular folding system. The ER ligand (agonist or antagonist) may interact with the ER ligand binding domain and may cause a conformational change. A bioluminescence initiating compound is introduced to the system (prior to and/or after the agonist or antagonist). If a bioluminescent signal is detected, a conformational change occurred. If no bioluminescent signal is detected, a conformational change did not occur. The intensity and/or strength of the bioluminescent signal can be used to determine if the ligand is an agonist or an antagonist. As mentioned above, standards can be used to assist in determining the relative strength between energy emitted as a result of an agonist and an antagonist. Additional details are described in the Example.

The agonists can include, but are not limited to, estradiol, diethylstilbestrol, diarylpropionitrile, and tetrahydrocannabinol. The antagonists can include, but are not limited to, methylpiperidinopyrazole and ICI 182780. The SERM can include, but is not limited to, hydroxytamoxifen, raloxifene, and tamoxifene. It should be noted that SERMs tend to have a mixed action (agonist and antagonist), but tend to be more similar to how an antagonist affects embodiments of the present disclosure. Distinguishing a SERM from agonist and/or antagonist can be conducted in a similar manner as described above for agonist and antagonist.

The method can be conducted in vitro or in vivo. The ER intramolecular folding system or sensor can be introduced, incorporated into, or expressed in a part of a cell or a host, as well as a transgenic animal or transgenic plant.

In another embodiment, the ER ligand binding domain can be designed to reduce interaction between the ER ligand binding domain and endogenous ER ligands. This mutation enhances the ability to use the ER intramolecular folding system in living hosts.

In an embodiment, the ER ligand binding domain is designed to reduce the interaction between the ER ligand binding domain and 17β-estradiol. In an embodiment, the sequence of the ER ligand binding domain can be modified by changing the amino acid a position 521 from glycine to threonine (SEQ ID Nos. 3, 11 and 12), which reduced interaction of the ER ligand binding domain with 17β-estradiol by about 90%, while only reducing the interaction of the ER ligand binding domain with other ER ligands slightly. Additional details are described in the Example. It should also be noted that the amino acid at position 521 could be changed from glycine to any one of the other amino acids (e.g., the other 19 amino acids (e.g., SEQ ID Nos. 11, 12, 13, and 14)).

It should be noted that the amount effective to result in uptake of each of the embodiments of the ER intramolecular folding system or sensor (e.g., for detecting ER ligand, ER agonists, ER antagonists, and/or SERMs) into the cells or tissue of interest will depend upon a variety of factors, including for example, the age, body weight, general health, sex, and diet of the host; the time of administration; the route of administration; the rate of excretion of the specific compound employed; the duration of the treatment; the existence of other drugs used in combination or coincidental with the specific composition employed; and like factors well known in the medical arts.

Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications.

Split Protein Fragments

The terms "split protein fragments" and "the bioluminescent protein" are often used in an interchangeable manner, but the spit protein fragments refer to two protein fragments that can complement to form the bioluminescent protein. Each of the protein fragment sequences is obtained from the bioluminescent protein. The combination of the protein fragment sequences may not include the entire bioluminescent protein sequence, and/or portions of the protein fragments sequences may overlap one another. The complementation of the split protein fragments forms an active bioluminescent protein or a fragment of an active bioluminescent protein. Thus, one skilled in the art would understand how these are used in the context of the entire disclosure.

The split protein can include, but is not limited to, non-self complementing split protein fragments and self complementing split protein fragments. In particular, the split protein can be obtained from bioluminscent proteins such as, but not limited to, Luciferases or photoproteins. In an embodiment, each of the split proteins can be obtained from bioluminscent proteins such as, but not limited to, *Renilla* Luciferase (the nucleotide sequences are described below and the amino acid sequence is SEQ ID: No 7 as well as other sequences described below), portions thereof, mutants thereof, variants thereof; *Coleoptera* Luciferase (the nucleotide sequence is SEQ ID: No 28, and the amino acid sequence is SEQ ID: No 29), portions thereof, mutants thereof, variants thereof; Firefly Luciferase (the nucleotide sequence is SEQ ID: No 10 and the amino acid sequence is SEQ ID: No 17), portions thereof, mutants thereof, variants thereof; *Gaussia* Luciferase (the nucleotide sequence is SEQ ID: No 30 and the amino acid sequence is SEQ ID: No 31), portions thereof, mutants thereof, variants thereof; aqeuorin photoproteinm Luciferase (the nucleotide sequence is SEQ ID: No 32, and the amino acid sequence is SEQ ID: No 33), portions thereof, mutants thereof, variants thereof; and bacterial luciferase (the nucleotide sequence is SEQ ID: No 34, and the amino acid sequence is SEQ ID: No 35), portions thereof, mutants thereof, variants thereof; and the like.

In an embodiment, the bioluminescent protein can include, but is not limited to, a *Renilla* Luciferase protein (SEQ ID: No 7, or split sequences corresponding to SEQ ID No. 37 and 38), double mutant (C124A/M185V) *Renilla* Luciferase proteins (e.g., SEQ ID: No 8), mutated *Renilla* Luciferase proteins (e.g., SEQ ID: No 9), variants of each, conservatively modified variants of each, and combinations thereof. Each of the double mutant (C124A/M185V) *Renilla* Luciferase (SEQ ID: No 8) and the mutated *Renilla* Luciferase proteins (SEQ ID: No 9) have the split to form the split protein fragments at the same amino acid as *Renilla* Luciferase protein (SEQ ID: No 7, or split sequences corresponding to SEQ ID No. 37 and 38). In other words, the split sequences of each of the double mutant (C124A/M185V) *Renilla* Luciferase and the mutated *Renilla* Luciferase protein are the same as the *Renilla* Luciferase protein (SEQ ID: No 7, or split sequences corresponding to SEQ ID No. 37 and 38) except for the mutations.

The term "mutant" is employed broadly to refer to a protein that differs in some way from a reference wild-type protein, where the protein may retain biological properties of the reference wild-type (e.g., naturally occurring) protein, or may have biological properties that differ from the reference wild-type protein. The term "biological property" of the subject proteins includes, but is not limited to, spectral properties, such as emission maximum, quantum yield, and brightness, and the like; in vivo and/or in vitro stability (e.g., half-life); and the like. Mutants can include single amino acid changes (point mutations), deletions of one or more amino acids (point-deletions), N-terminal truncations, C-terminal truncations, insertions, and the like. Mutants can be generated using standard techniques of molecular biology.

In an embodiment, the Luciferase mutants retain Luciferase activity (e.g., catalyze the conversion of a coelenterazine substrate into a luminescent product in the presence of molecular oxygen). In an embodiment, the Luciferase mutants have at least one of the following properties relative to their corresponding reference wild-type protein: modulated stability; enhanced light output; and/or modulated emission wavelength maximum, and modulated substrate utilization. In certain embodiments, the subject mutants include two or more of the above properties (e.g., modulated stability and enhanced brightness, enhanced light output and modulated emission maximum, modulated stability and modulated emission maximum, and the like.), or the mutants may include three or more of the above properties (e.g., modulated stability, enhanced light output and modulated emission maximum).

In an embodiment, the split protein fragments are self complementing fragments (e.g., inherent self affinity between the N- and C-terminal fragments of a split protein (e.g., a monomeric Firefly Luciferase protein) brings the fragments close to each other and generates an event called complementation) and do not bioluminesce when separated. The split protein, self complementing fragments are able to spontaneously self complement upon coming into close enough proximity to recover the substrate binding property or upon coming in contact with one another to form a bioluminescent protein. An example of the self complementing fragments include the bioluminescent Firefly Luciferase protein, which can spontaneously self complement and then bioluminescence upon interaction with a bioluminescence initiating compound.

In an embodiment of the split protein self complementing fragments, the fragments are obtained from the Firefly Luciferase protein and conservatively modified variants thereof. The split protein, self complementing fragments include portions, or conservatively modified variants thereof, of the Firefly Luciferase protein (the nucleotide sequence is SEQ ID: No 10 and the amino acid sequence is SEQ. ID: 17). The protein and/or genetic sequences are described in the Example and figures. The split protein, self complementing fragments may include, but are not limited to, a N fragment (e.g., amino acid sequence SEQ. ID No. 19 and nucleotide sequence SEQ. ID No. 18 (corresponding to amino acids residues 1 to 475)) and a C fragment (e.g., amino acids residue 245 to 550 or 300 to 550 of SEQ ID: No 17 and portion of the nucleotide sequence SEQ. ID No. 10 (corresponding to amino acids 245 to 550 or 398 to 550)) of the Firefly Luciferase protein. In particular, split protein self complementing fragments may include, but are not limited to, a Nfluc fragment (amino acids 1-398 of SEQ ID: No 23), a Nfluc fragment (amino acid sequence (amino acids 1-474) SEQ. ID No. 19 and nucleotide sequence SEQ. ID No. 18), a Nfluc fragment (amino acid sequence (amino acids 1-455) of SEQ ID: No 17 and nucleotide sequence SEQ. ID No. 10 (corresponding to amino acids residue 1 to 455)), a Nfluc fragment (amino acid sequence (amino acids 1-450) of SEQ ID: No 17 and nucleotide sequence SEQ. ID No. 10 (corresponding to amino acids residue 1 to 450)), a Nfluc fragment (amino acid sequence (amino acids 1-398) of SEQ ID: No 23 and nucleotide sequence SEQ. ID No. 22), a Cfluc fragment (amino acids 245-550 of SEQ ID: No 17 and nucleotide sequence SEQ. ID No. 10 corresponding to amino acids 245 to 550), a Cfluc fragment (SEQ ID: No 21 and nucleotide sequence SEQ. ID No. 20 corresponding to amino acids 265 to 550), a Cfluc fragment (amino acids 300-550 of SEQ ID: No 17 and nucleotide sequence SEQ. ID No. 10 corresponding to amino acids 300 to 550), a Cfluc fragment (amino acids 310-550 of SEQ ID: No 17 and nucleotide sequence SEQ. ID No. 10 corresponding to amino acids 310 to 550), a Cfluc fragment (amino acids 325-550 of SEQ ID: No 17 and nucleotide sequence SEQ. ID No. 10 corresponding to amino acids 325 to 550), a Cfluc fragment (amino acids 398-550 of SEQ ID: No 25 and nucleotide sequence SEQ. ID No. 24), and a Cfluc fragment (amino acids 394-550 of SEQ ID: No. 27 nucleotide sequence SEQ. ID No.26).

The Firefly Luciferase protein or the split protein, self complementing fragments can include conservativley modified variants as long as the conservativley modified variant retains certain characteristics (e.g., the ability to luminesce upon complementation) of the Firefly Luciferase protein or the split protein self complementing fragments. It should be noted that polynucleotides encoding the conservativley modified variants are intended to be disclosed by and included in this disclosure.

The split protein, self complementing fragments can be included in a fusion protein. For example, the fusion protein can include the split proteins of the self complementing fragments and the ER ligand binding domain while also including linkers, and/or other components consistent with the teachings of this disclosure. The split protein, self complementing fragments or a fusion protein including the split protein, self complementing fragment can be expressed in a system (e.g., a cell) using a vector, for example by methods known to those of skill in the art.

ER Folding System Vector

Embodiments of the present disclosure include, but are not limited to, polynucleotides that encode the ER intramolecular folding systems as described above and degenerate nucleotide sequences thereof, as well as fusion proteins of the ER intramolecular folding systems and degenerate nucleotide sequences thereof. Methods of producing vectors, other expression systems, (e.g., viral and non-viral) and polynucleotides are well known in the art. It should be noted that the fusion protein can be expressed using other expression systems, and the vector is merely an illustrative embodiment.

Bioluminescence Initiating Compound

As mentioned above, the bioluminscent protein is used in conjunction with a bioluminescence initiating compound to produce a radiation emission that is absorbed by the quantum dot. The bioluminescence initiating compound can include, but is not limited to, coelenterazine, analogs, and functional derivatives thereof, and D-luciferin analogs, and functional derivatives thereof. Derivatives of coelenterazine include, but are not limited to, coelenterazine 400a, coelenterazine cp, coelenterazine f, coelenterazine fcp, coelenterazine h, coelenterazine hcp, coelenterazine ip, coelenterazine n, coelenterazine O, coelenterazine c, coelenterazine c, coelenterazine i, coelenterazine icp, coelenterazine 2-methyl, and deep blue coelenterazine (DBC) (described in more detail in U.S. Pat. Nos. 6,020,192; 5,968,750 and 5,874,304). In an embodiment, the bioluminescence initiating compound can be D-luciferin when the bioluminescence compound is Firefly Luciferase.

In general, coelenterazines are known to luminesce when acted upon by a wide variety of bioluminescent proteins, specifically luciferases. Useful, but non-limiting, coelenterazines are disclosed in U.S. patent application Ser. No. 10/053,482, filed Nov. 2, 2001, the disclosure which is hereby incorporated by reference in its entirety. Coelenterazines are available from Promega Corporation, Madison, Wis. and from Molecular Probes, Inc., Eugene, Oreg. Coelenterazines may also be synthesized as described for example in Shimomura et al., Biochem. J. 261: 913-20, 1989; Inouye et al., Biochem. Biophys. Res. Comm. 233: 349-53, 1997; and Teranishi et al., Anal. Biochem. 249: 37-43, 1997.

Additional Methods of Use

In an embodiment, the ER intramolecular folding systems and methods described herein can be used to monitor and assess biological interactions by modifying vector constructs (e.g., ER interactions) in a transgenic animal or a transgenic plant.

In another embodiment, a cell line or transgenic animal is marked with vector sets described herein that are developed utilizing coding regions of sequences for the ER folding system, for example, followed by optical imaging to image and/or quantitate ER related events in the presence and absence of molecules (e.g., pharmaceuticals) designed to modulate the interaction. As will be appreciated by the skilled practitioner, this technique will significantly accelerate drug validation by allowing testing in vivo.

In this regard, the present disclosure also includes transgenic animals comprising exogenous DNA incorporated into the animal's cells to effect a permanent or transient genetic change, preferably a permanent genetic change. Permanent genetic change is generally achieved by introduction of the DNA into the genome of the cell. Vectors for stable integration include plasmids, retroviruses and other animal viruses, YACS, and the like. Generally, transgenic animals are mammals, most typically mice.

The exogenous nucleic acid sequence may be present as an extrachromosomal element or stably integrated in all or a portion of the animal's cells, especially in germ cells.

Unless otherwise indicated, a transgenic animal includes stable changes to the GERMLINE sequence. During the initial construction of the animal, chimeric animals (chimeras) are generated, in which only a subset of cells have the altered genome. Chimeras may then be bred to generate offspring heterozygous for the transgene. Male and female heterozygotes may then be bred to generate homozygous transgenic animals.

Typically, transgenic animals are generated using transgenes from a different species or transgenes with an altered nucleic acid sequence. For example, a human gene may be introduced as a transgene into the genome of a mouse or other animal. The introduced gene may be a wild-type gene, naturally occurring polymorphism, or a genetically manipulated sequence, for example having deletions, substitutions or insertions in the coding or non-coding regions.

For example, an introduced transgene may include genes corresponding to the ER folding system, which may become functional via complementation or reconstitution when exposed to appropriate test proteins or, alternatively, which may become non-functional when exposed to a particular test protein that blocks complementation. Such a transgene, when introduced into a transgenic animal or cells in culture, is useful for testing potential therapeutic agents known or believed to interact with a particular target protein implicated in a disease or disorder. Where the introduced gene is a coding sequence, it is usually operably linked to a promoter, which may be constitutive or inducible, and other regulatory sequences required for expression in the host animal.

Transgenic animals can be produced by any suitable method known in the art, such as manipulation of embryos, embryonic stem cells, etc. Transgenic animals may be made through homologous recombination, where the endogenous locus is altered. Alternatively, a nucleic acid construct is randomly integrated into the genome. Vectors for stable integration include plasmids, retroviruses and other animal viruses, YACS, and the like.

Numerous methods for preparing transgenic animals are now known and others will likely be developed. See, e.g., U.S. Pats. Nos. 6,252,131, 6,455,757, 6,028,245, and 5,766,879, all incorporated herein by reference. Any method that produces a transgenic animal expressing a reporter gene following complementation or reconstitution is suitable for use in the practice of the present invention. The microinjection technique is particularly useful for incorporating transgenes into the genome without the accompanying removal of other genes.

Kits

This disclosure encompasses kits that include, but are not limited to, a ER intramolecular folding system or vectors thereof; a bioluminescence initiating compound; and directions (written instructions for their use). The components listed above can be tailored to the particular biological event (e.g., ER related events) to be monitored as described herein. The kit can further include appropriate buffers and reagents known in the art for administering various combinations of the components listed above to the host cell or host organism. The components of the present disclosure and carrier may be provided in solution or in lyophilized form. When the components of the kit are in lyophilized form, the kit may optionally contain a sterile and physiologically acceptable reconstitution medium such as water, saline, buffered saline, and the like.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include $\pm 1\%$, $\pm 2\%$, $\pm 3\%$, $\pm 4\%$, $\pm 5\%$, $\pm 6\%$, $\pm 7\%$, $\pm 8\%$, $\pm 9\%$, or $\pm 10\%$, or more of the numerical value(s) being modified. In addition, the phrase "about 'x' to 'y'" includes "about 'x' to about 'y'".

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

EXAMPLE

Now having described the embodiments of the disclosure, in general, the example describes some additional embodiments. While embodiments of present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Introduction

Strategies for high-throughput analysis of interactions of various hormones and drugs with the estrogen receptor would be highly beneficial. Through a careful analysis of the crystal structure of the human estrogen receptor ligand-binding domain (hER-LBD) in complex with different ligands, it is believed that the hER-LBD intramolecular folding pattern could be used to distinguish agonists from antagonists. Therefore, intramolecular folding sensors encoding for various hER-LBD fusion proteins were constructed and validated that could lead to split *Renilla* Luciferase reporter complementation in the presence of the appropriate ligands. A novel mutant hER with low affinity for circulating estradiol was also identified for use in imaging living subjects. This is the first sensor suited for high-throughput quantitative analysis of drugs using cell lysates, intact cells, and molecular imaging of small living subjects.

Is should be noted that even with the existence of other assays, there are no assays that allow for quantitative screening of ER agonists, antagonists, and selective estrogen receptor modulators (SERMs) in cell lysates or intact cells in a high-throughput fashion. In addition, no assays exist that allow for evaluation of ER and its ligands in the context of a living subject through noninvasive molecular imaging.

In this example it is shown that the chemical agonists and antagonists of ER lead to a specific pattern of intramolecular folding conformational changes in the ER-LBD that can be exploited to yield an intramolecular folding sensor with specific split reporter complementation patterns (FIG. 1). A split synthetic *Renilla* Luciferase (RLUC, SEQ. ID No. 7) complementation system was used in this example to assay complemented luciferase activity in cells and also for noninvasive bioluminescence optical imaging in living mice. The constructed ER folding sensors that successfully identify ER ligands and also distinguish agonists and antagonists were studied in different cell lines and as cell implants in living animals while utilizing various drugs. Moreover, a novel mutant hER was identified that shows low affinity to 17β-estradiol and was shown to be useful for extending this sensor for characterization of ER ligands in living subjects without significant interference from endogenous estrogens.

Results

Figure 2:
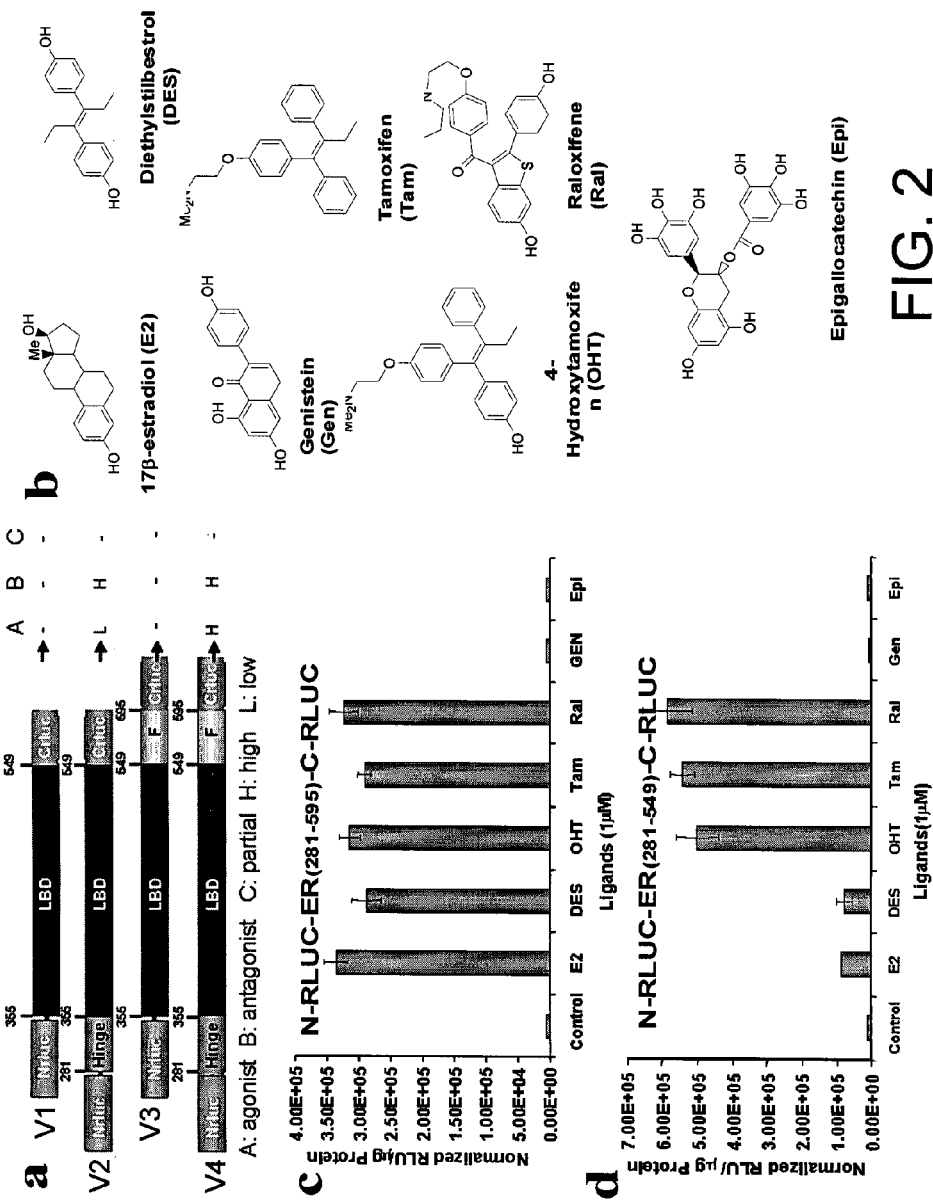
FIG. 2A illustrates a schematic of different vectors with split RLUC fragments and the human estrogen receptor LBD with different flanking sequences on either side, constructed to identify a vector that gives ligand-induced, intramolecular folding-based, RLUC complementation that distinguishes agonists from antagonists.
FIG. 2B illustrates chemical structures of different ligands used in the examples below.
FIG. 2C illustrates 293T cells transfected with vector constructs expressing the fusion protein N-RLUC-hER$_{281-595(Seq.\ ID\ No.\ 2)}$-C-RLUC, showing efficient intramolecular folding assisted complementation by both agonists and antagonists.
FIG. 2D illustrates 293T cells transfected with the vector construct expressing the fusion protein N-RLUC-hER$_{281-549(Seq\ ID\ No.\ 1)}$-C-RLUC, showing efficient intramolecular folding assisted complementation that is able to distinguish antagonists (relatively high signal) from agonists (relatively low signal). The results are the average of triplicate samples, and the error bars represent SEM of triplicate determinations.
Figure 7:
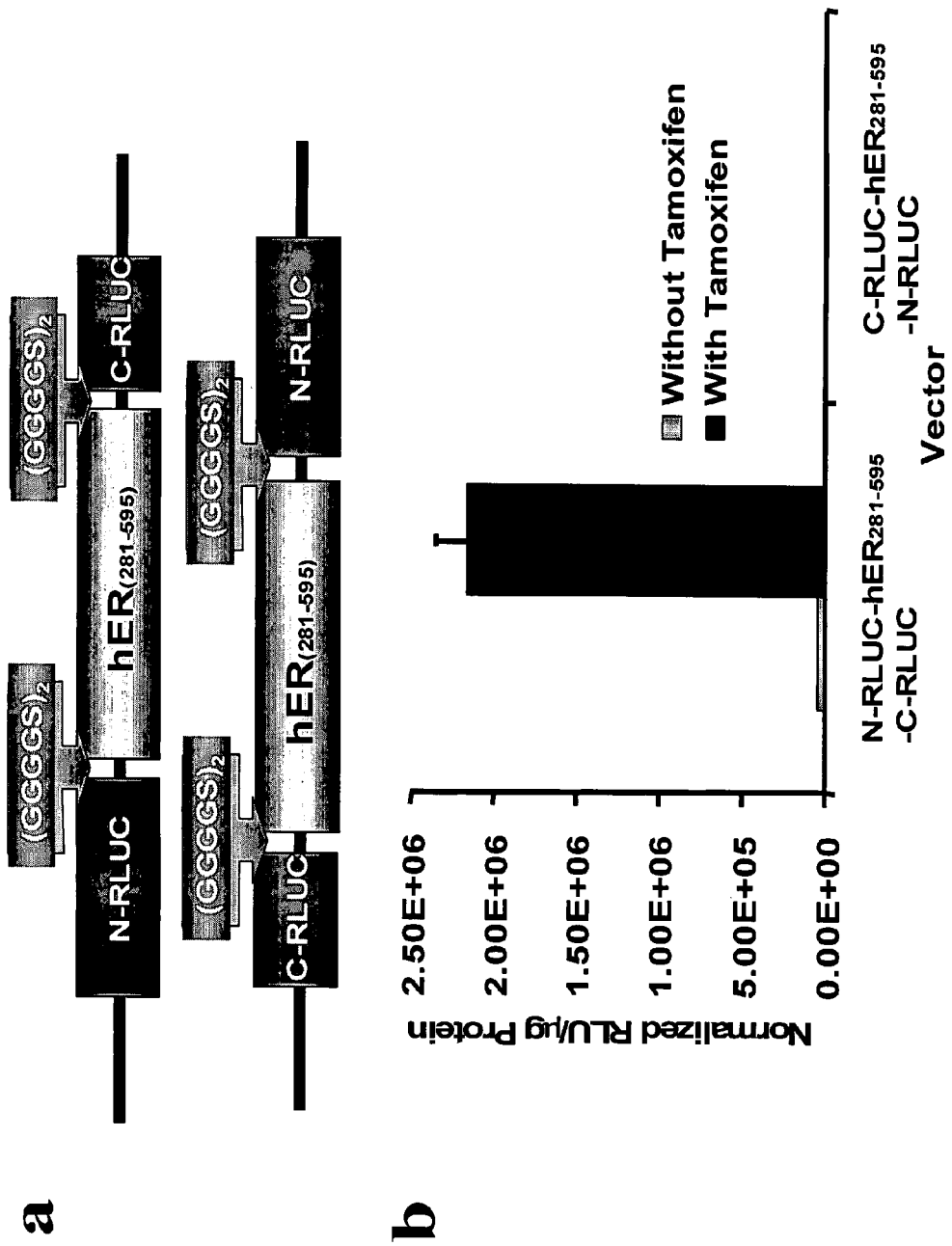
FIG. 7A shows schematic illustrations of vectors constructed to identify the orientation of N- and C-split RLUC fragments that generate efficient estrogen receptor ligand-induced complementation.
FIG. 7B illustrates that the 293T cells transiently expressing fusion protein N-RLUC-hER$_{281-595(Seq\ ID\ No.\ 2)}$-C-RLUC showed significant ligand Tamoxifen-induced RLUC complementation as compared to the cells expressing C-RLUC-hER$_{281-595(Seq\ ID\ No\ 2)}$-N-RLUC.

ER ligand-induced, intramolecular folding-based, split RLUC complementation sensors were developed by constructing vectors to express fusion protein chimera containing RLUC fragments (SEQ ID Nos. 36-39) with varying lengths of hER. The ligand-binding domain (LBD) of hER with a protein length of around 200 amino acids (355-549) (SEQ ID No: 3, amino acids 355-549) is enough for efficient binding of estrogen and other estrogen analogs. The LBD of ER is flanked on the amino terminal end with a DNA binding domain and/or the carboxy terminal end with domain F. The C-terminus of LBD helix12 and the domain F are differentially positioned when ligand agonists and antagonists binds with it. Hence, to achieve efficient ligand induced split RLUC complementation, and also a ligand induced complementation that distinguishes agonists from antagonists; several factors were considered. These factors include: (1) the distance between the complementing N- and C-RLUC fragments (SEQ. ID No. 37 and 39 respectively) in the fusion system before and after the binding of ligands, (2) the orientation of N- and C-RLUC fragments after binding of different ER ligands, (3) the position of RLUC fragments after ligand binding. By carefully considering all of these factors along with the crystal structure of different ER-ligand complexes, a series of vectors were constructed that expresses fusion protein chimeras with split RLUC fragments and hER of different lengths (FIG. 2a). In addition, the orientation of split RLUC fragments needed for efficient complementation (FIG. 7a-7b) was confirmed.

Figure 8:
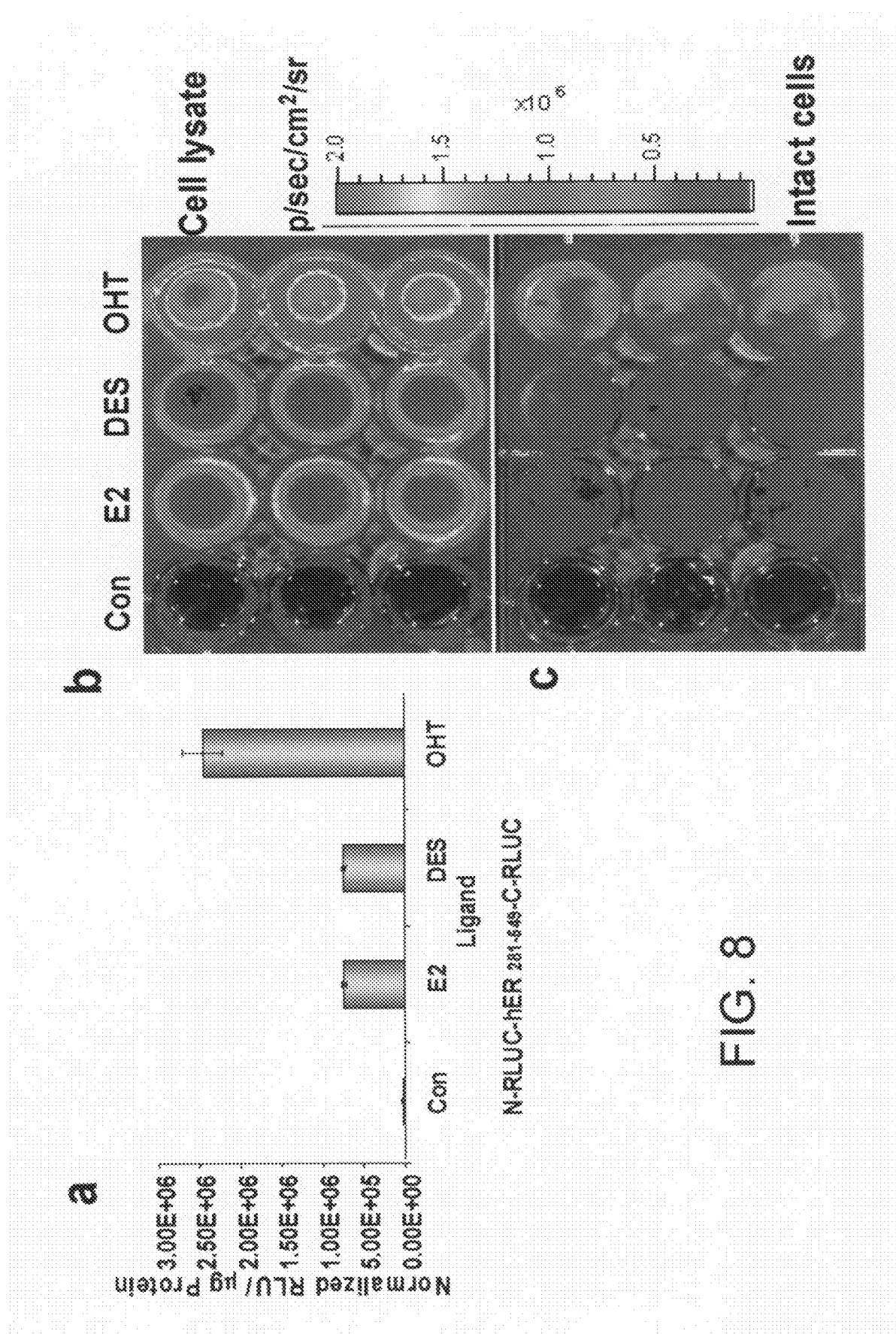
FIG. 8 illustrates the 293T cells expressing fusion protein N-RLUC-ER$_{281-549(Seq\ ID\ No.\ 1)}$-C-RLUC assayed for luciferase activity after exposure to ligands 17β-estradiol (E2), Diethylstilbestrol (DES) and 4-hydroxytamoxifen (OHT) by luminometry of the cell lysates (FIG. 8A) and bioluminescence imaging by optical CCD camera in cell lysates (FIG. 8B) and intact cells (FIG. 8C) after the addition 1 μg/well substrate coelenterazine. The results show no relation with multi-drug resistance and the substrate coelenterazine mediated luciferase signal.

All these vectors were studied in transiently transfected 293T cells by treating with several ER ligands including, 17β-estradiol, Tamoxifen, Raloxifene, Genistein, Diethylstilbestrol and 4-hydroxytamoxifen (FIG. 2b). Among the different vectors studied, the vector expressing the fusion protein containing hER of amino acids 281 to 595 [hER$_{281-595}$ (SEQ. ID No: 2): partial hinge (domain D), LBD (domain E) and domain F] showed significant levels of ligand-induced RLUC complementation for both agonists and antagonists. The level of complementation achieved by this vector was 80±15 times greater than in cells not exposed to any ligands. The cells exposed to a partial agonist (Genistein) showed no complementation (FIG. 2c). Similarly the cells transfected with the vector constructed to express a fusion protein containing hER of amino acids 355 to 549 (hER$_{355-549}$: domain E) (SEQ. ID No: 3, amino acids 355-549) and 355 to 595 (hER$_{355-595}$: domains E and F) showed no significant level of complementation with all the different ligands used for this study. At the same time, the cells transfected with the vector expressing the fusion protein-containing hER of amino acids 281 to 549 (hER$_{281}$ 549: domains D and E) (SEQ. ID No: 1) showed complementation that clearly distinguished agonists from antagonists. The complementation achieved by the proteins encoded by this vector when treated with antagonist and agonists were 80±15 fold and 15±5 fold (P<0.05) more, respectively, than the controls. Partial agonist showed no significant complementation (FIG. 2d). To confirm the multi-drug resistant system of cells has no confounding role in the assay (since coelenterazine is a substrate for p-glycoprotein), cells were exposed to different ER ligands and the subsequent *Renilla* Luciferase signal measured. 293T cells transfected to express N-RLUC-ER$_{281-549(Seq\ ID\ No:\ 1)}$-C-RLUC were exposed to different ER ligands and the cell lysates assayed by luminometry. CCD imaging of the cell lysates and the intact cells was also performed. The results show no significant changes in the signal from both cell lysates and intact cells supporting that changes are not due to coelenterazine availability (FIG. 8a-8c).

Western Blot Analysis of Endogenous ERα in MCF7 Cells and the Sensor Protein Level in Transiently Transfected 293T Cells Show No Significant Change in Response to Treatment With Different ER Ligands.

Figure 3:
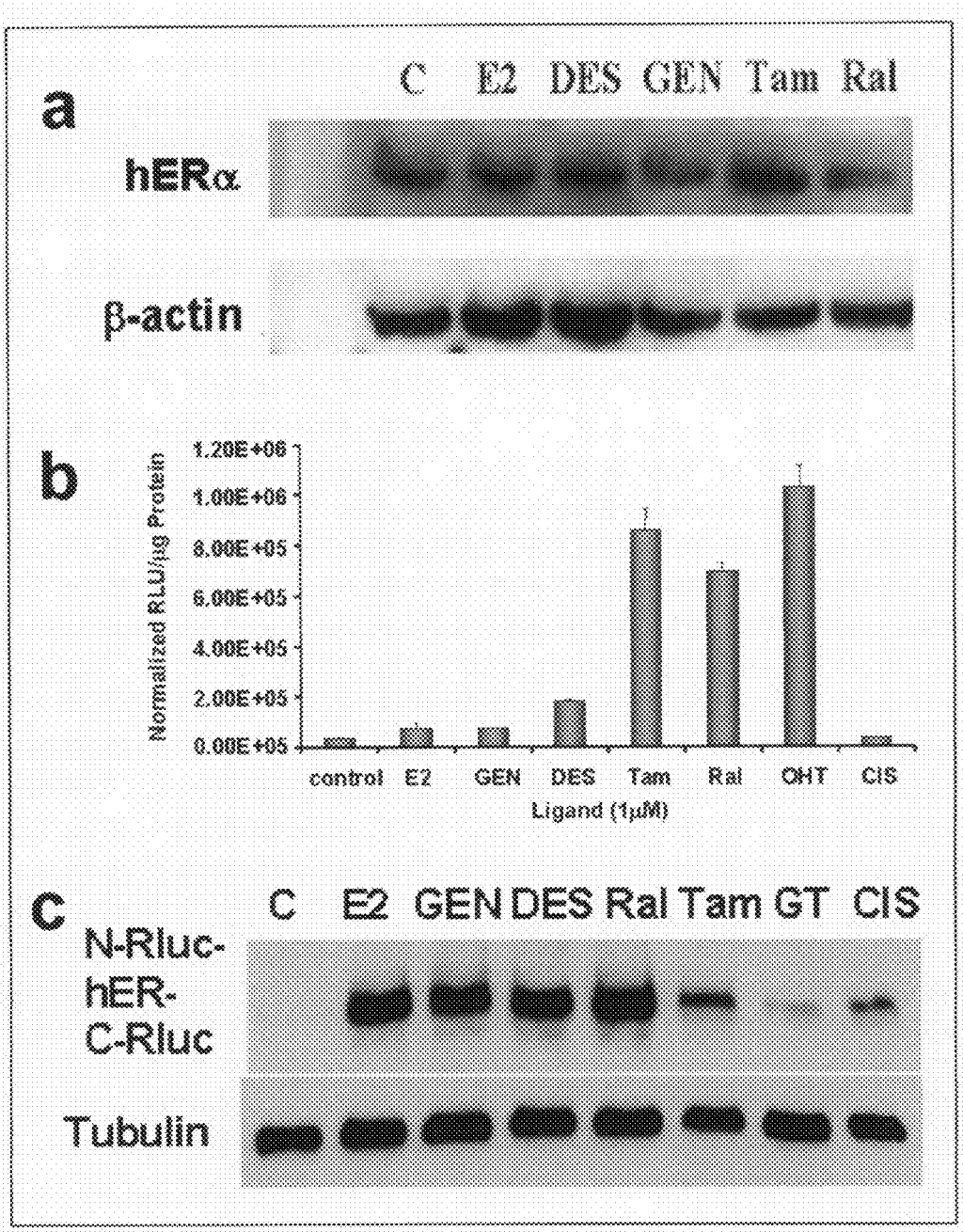
FIG. 3A is a western blot analysis using an anti-ERα antibody of MCF7 cells before (control) and after treatment with different ER ligands. There is no significant difference in the endogenous ER protein level before and after treatment with the ligands 17β-estradiol (E2), Diethylstilbestrol (DES), Genistein (GEN), Tamoxifen (Tam) and Raloxifene (Ral). The cells were also assayed for β-actin as an internal loading control.
FIG. 3B illustrates the estrogen receptor ligand antagonist and agonist specific intramolecular folding-assisted RLUC complementation that was studied in 293T cells transiently transfected to express the fusion protein N-RLUC-hER$_{281-549(Seq\ ID\ No.\ 1)}$-C-RLUC.
FIG. 3C illustrates Western blot analysis of the same sample for estimating the fusion protein level by using anti-RLUC antibody.

To study the significance of expressed intracellular ER protein levels in the intramolecular folding assisted RLUC complementation system, Western blot analysis was performed. The ER protein level was estimated before and after treating the cells with different ER ligands. The results show no significant difference in the intracellular ER protein levels in MCF7 cells before and after treatment (FIG. 3a). Similarly, to confirm the ligand-induced hER intramolecular folding assisted RLUC complementation is not due to excessive expression of the folding sensor that leads to an increase in the amount of protein level, Western blot analysis of 293T cells transfected to express the fusion protein RLUC-hER$_{281-549(Seq\ ID\ No:\ 1)}$-C-RLUC using the RLUC antibody before and after treating with different ER ligands were also studied. The result shows no significant difference in the protein level after being treated with different ligands. The luciferase signal estimated for the ligand induced RLUC complementation for corresponding samples showed significant levels of signal only with the antagonists (FIG. 3b). Although the cells treated with the antagonist tamoxifen showed a low level of sensor protein, the RLUC signal produced was significantly greater than the cells treated with the agonist 17β-estradiol. The protein level of samples treated with antagonist tamoxifen and two anticancer drugs, Epigallocatechin gallate and Cisplatinum, showed significant reduction in the expressed fusion protein levels; still tamoxifen showed significant level of complemented RLUC signal (FIG. 3c). These results confirm that the variations in the RLUC signal achieved from the cells treated with different ligands are not due to the changes in the protein level, but instead are from the complementation pattern induced by the ligands.

Ligand-induced Intramolecular Folding of hER Studied by RLUC Complementation at Different Time Points Shows Significant Level of Induction After 18 Hrs of Exposure to Ligands.

Figure 4:
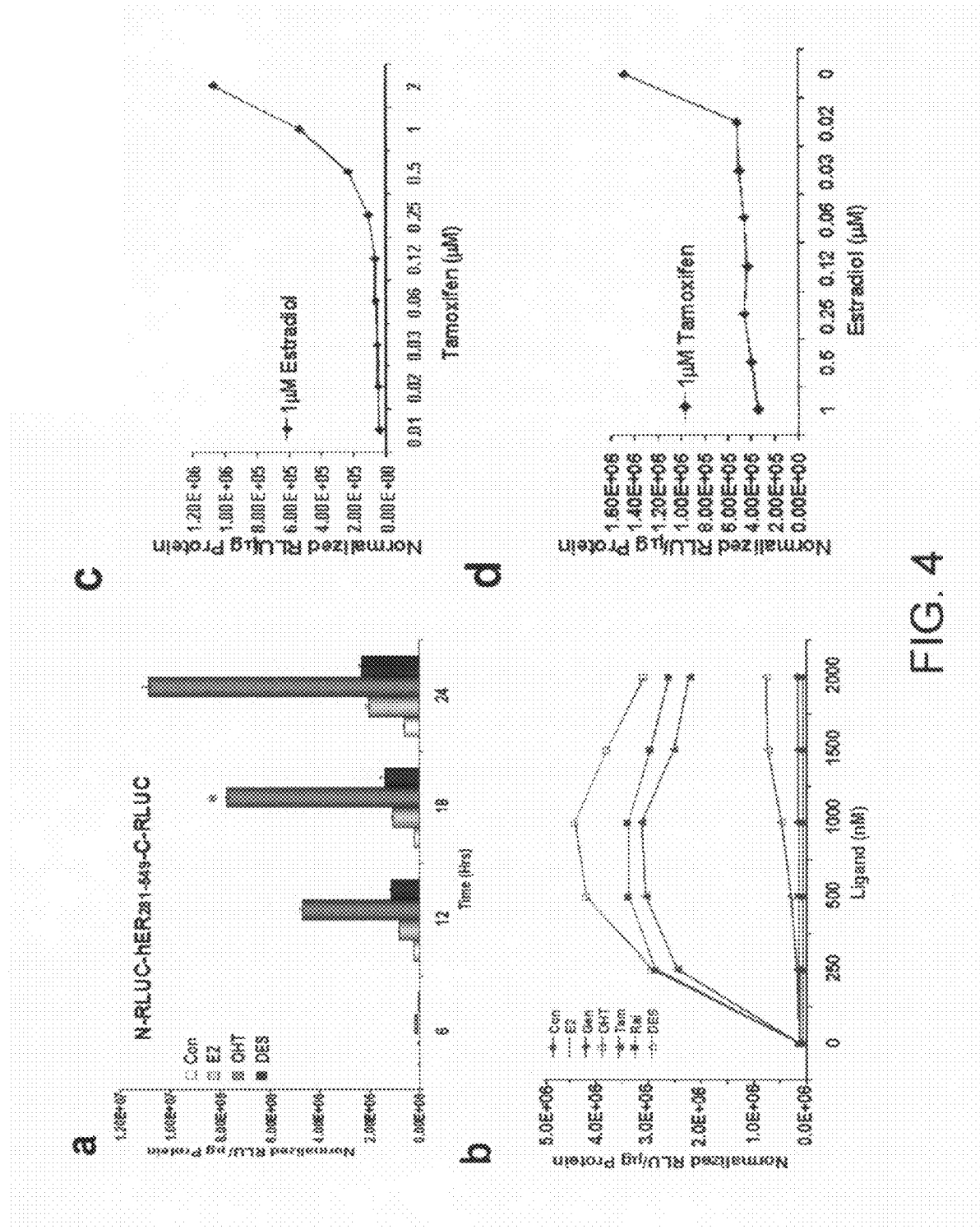
FIG. 4A illustrates the transiently transfected 293T cells expressing fusion protein N-RLUC-hER$_{281-549(Seq\ ID\ No.\ 1)}$-C-RLUC that were assayed for ligand induced intramolecular folding at different time points after exposure to different ligands, including 17β-estradiol (E2), 4-hydroxytamoxifen (OHT) and Diethylstilbestrol (DES). The maximum ratio of ligand induced RLUC complementation in comparison with the control was achieved at 18 hours (*).
FIG. 4B illustrates the concentration-dependent activation of ligand-induced RLUC complementation in transiently transfected 293T cells expressing fusion protein N-RLUC-hER$_{281-549(Seq\ ID\ No.\ 1)}$-C-RLUC by the ligands 17β-estradiol (E2), Genistein (Gen), 4-hydroxytamoxifen (OHT), Tamoxifen (Tam), Raloxifene (Ral) and Diethylstilbestrol (DES). The cells exposed to increasing concentrations of ligands show increased RLUC activity by the ligands 4-hydroxytamoxifen (□), Tamoxifen (▲) and Raloxifene (■). The ligand Diethylstilbestrol (Δ) shows maximum activity at 1 μM concentration. All ligands showed significant correlation between the concentration of ligands used and the RLUC signal produced.
FIG. 4C illustrates a fixed concentration of agonist 17β-estradiol (1 μM) competitive binding with the estrogen receptor in the presence of varying concentrations of the antagonist Tamoxifen, studied in transiently transfected 293T cells expressing fusion protein N-RLUC-hER$_{281-549(Seq\ ID\ No.\ 1)}$-C-RLUC by estimating the complemented RLUC activity.
FIG. 4D illustrates a fixed concentration of antagonist Tamoxifen (1 μM), studied in the presence of varying concentrations of agonist 17β-estradiol. The samples were normalized for transfection efficiency by co-transfecting with Firefly Luciferase.

To find the time point at which ligand induced RLUC complementation achieves maximum activity, 293T cells transiently transfected to express the fusion protein N-RLUC-hER$_{281-549(Seq\ ID\ No:1)}$-C-RLUC were exposed to 1 μM concentrations of three representative ligands, including the agonists 17β-estradiol and Diethylstilbestrol, and antagonist 4-hydroxytamoxifen. The cells were assayed for complemented RLUC activity at 6, 12, 18 and 24 hours. The result shows significant ($P<0.0015$) level of RLUC complementation from cells exposed to the antagonist 4-hydroxytamoxifen at all time points studied. The agonists 17β-estradiol and Diethylstilbestrol showed complementation that was significantly less ($P<0.001$) when compared to 4-hydroxytamoxifen at all time points studied. The maximum level of ligand induced RLUC complementation was achieved after 18 hours of exposure to ligands (FIG. 4a).

Ligand-induced Intramolecular Folding of hER in Response to Varying Concentrations of Different Ligands Shows Significant Correlation With the Achieved RLUC Complementation.

To study the efficiency of hER ligand-induced RLUC complementation in response to varying concentrations of ligands, different ligands were studied in transiently transfected 293T cells expressing the fusion protein N-RLUC-hER$_{281-549}$-C-RLUC with six different concentrations (0-2 μM). The result shows significant linear correlation between the complemented RLUC activity and the concentrations of ligands with maximum ligand concentrations of up to 1 μM (FIG. 4b).

Competitive Binding of ER Agonists and Antagonists in Inducing RLUC Complementation in a Stably Transfected 293T Cells Shows Minimum Levels of the Agonist 17β-Estradiol is Enough to Block Complementation Induced by the Antagonist Tamoxifen.

To study the imaging of ER intramolecular folding sensor in living mice, the 293T cells were transfected to stably express the fusion proteins containing both wild and mutant-hER$_{281-549}$ (SEQ ID No: 1) with split RLUC fragments. The stable cells were analyzed for ligand-induced RLUC complementation with all the ligands used for transient expression studies. The result showed no significant difference between the stable and transiently transfected cells (data not shown). The stable cells were used for studying the competitive binding of ligand agonists and antagonists in inducing RLUC complementation. The cells were assayed for complemented RLUC activity 18 hours after simultaneously exposed to a fixed concentration of agonist (17β-estradiol: 1 μM) with varying concentrations of antagonist (Tamoxifen: from 1 μM to 0.0078 μM). Similarly, another experiment was set with a fixed concentration of antagonist (Tamoxifen: 1 μM) and varying concentrations of agonist (17β-estradiol: ranged from 1 to 0.0078 μM). The result shows complemented RLUC activity that is less when the cells simultaneously exposed to Tamoxifen and 17β-estradiol. But it is significantly higher than the cells exposed to 17β-estradiol alone. Even a very low concentration (8 nM) of 17β-estradiol is able to significantly block Tamoxifen-induced RLUC complementation (FIGS. 4c & 4d).

A Single Amino Acid Change at Position 521 (SEQ. ID No. 2) with 20 Different Amino Acids of Choice Identified the Amino Acid Threonine as an Efficient Choice for Selectively Abolishing 17β-Estradiol Affinity for ER Without Significantly Affecting the Affinity for Other Ligands.

Figure 9:
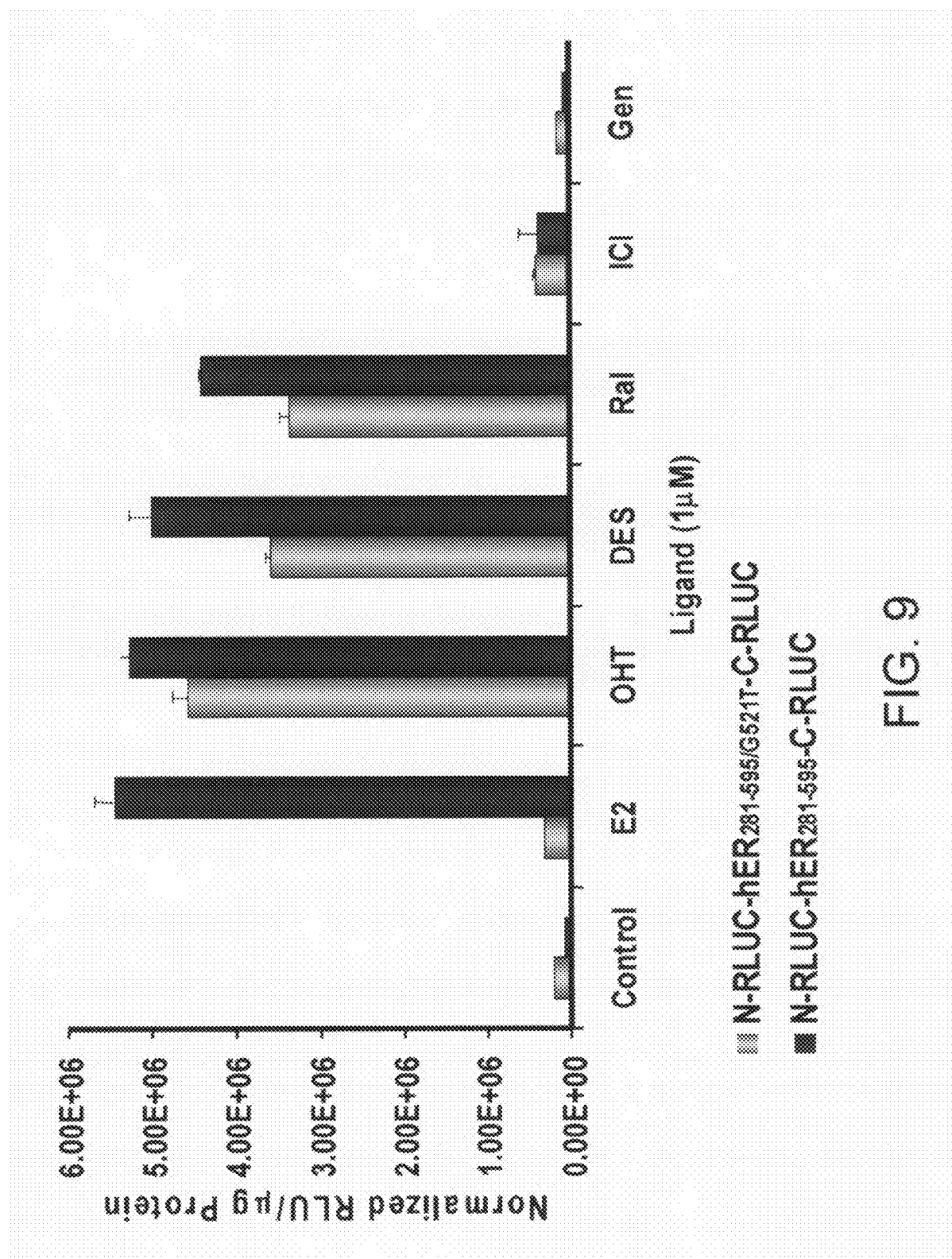
FIG. 9 illustrates the comparison of ligand-induced RLUC complementation generated by 293T cells expressing the fusion protein N-RLUC-hER$_{281-595/G521T(Seq\ ID\ No.\ 12)}$-C-RLUC (mutant hER) with the 293T cells expressing fusion protein N-RLUC-hER$_{281-595(Seq\ ID\ No.\ 2)}$-C-RLUC (wild type hER). The results show the selective reduction of RLUC activity by the fusion protein containing the mutant hER for the ligand 17β-estradiol.
Figure 10:
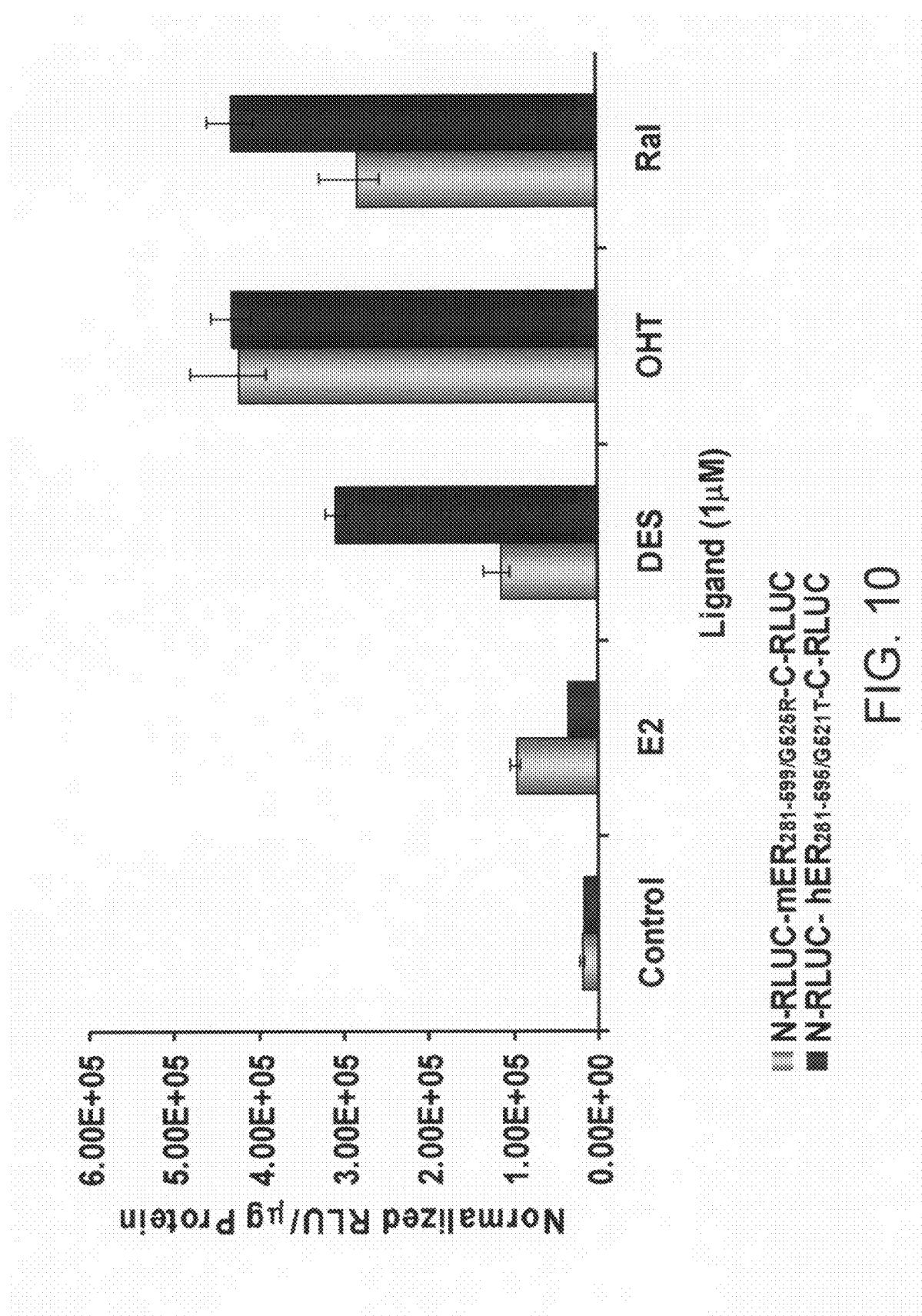
FIG. 10 illustrates the comparison of 293T cells expressing fusion protein N-RLUC-ER-C-RLUC containing the mutant form of human ER$_{281-595/G521T}$ with the mutant form of mouse ER$_{281-599/G525R}$ (Seq. ID No. 13) for RLUC complementation induced by different ligands.

The use of an intramolecular folding sensor in living animals in either a tumor model or a transgenic model will face the inherent problem of binding with endogenous 17β-estradiol. Hence, to overcome this issue, mutations (at amino acid position 521) analogous to the mutation generated in mouse estrogen receptor at amino acid position 525 that has been reported to reduce affinity to 17β-estradiol were generated. Twenty different mutants were constructed. To generate point mutations vector constructs were used that express fusion protein N-RLUC-hER$_{281-595(Seq\ ID\ No:\ 2)}$-C-RLUC and usually generate RLUC complementation for both agonists and antagonists. The mutant with glycine to threonine (G521T) transition showed 90% reduction in the receptor mediated RLUC complementation to agonist 17β-estradiol, and only 10-20% reduction for all other ligands used in the study (FIG. 9). This novel mutant was used for constructing the intramolecular folding sensor that distinguishes agonists and antagonists, and studied in transiently transfected 293T cells by exposing to different ligands. The mutants in Table 1 were constructed for the sensor N-RLUC-hER$_{281-549/G521T(Seq\ ID\ No.\ 12)}$-C-RLUC that distinguishes ER ligands for all the animal studies. The results of all 20 mutants screened for 7 different ER ligands are presented as Table 1 in FIG. 11. The human ER mutant generated from this study was compared with the sensor constructed with the mouse mutant ER. The result showed mutant human ER with G521T with lower RLUC complementation (5-6%) than mutant mouse ER (22-25%) to 17β-estradiol. In addition, the mutant mouse ER also showed significant reduction in the activity for the other ligand agonist, Diethylstilbestrol, used in this study, but this was not observed with the sensor with the mutant hER (FIG. 10).

Imaging of the ER Intramolecular Folding Sensor in Living Mice Shows Significant Signal From the Site Implanted With Cells Expressing the Fusion Protein N-RLUC-hER$_{281-549/G521T(Seq\ ID\ No.\ 12)}$-C-RLUC Upon Intraperitoneal Injection of the Antagonist Raloxifene.

To study the ER intramolecular folding sensors in living mice, the sensors expressing wild and mutant type ER with the length that distinguishes agonists from antagonists (amino acids 281-549, SEQ. ID No: 1) were used. The 293T cells stably expressing fusion proteins containing RLUC fragments with wild and mutant forms of hER (N-RLUC-hER$_{281-549(Seq\ ID\ No.\ 1)}$-C-RLUC and N-RLUC-hER$_{281-549/G521T(Seq\ ID\ No.\ 12)}$-C-RLUC) were imaged. The animals (n=3 for each group-Female) were implanted with 2 million cells on either side in the back of the thigh region. The animals were imaged immediately after implanting the cells and 24 hours after i.p. injection of 0.5 mg of ligand antagonist Raloxifene. The result shows significant signal ($P<0.001$)

from the site implanted with the cells expressing the fusion protein containing the mutant form of human ER [wild ER: $1\pm0.3\times10^3$ p/sec/cm$^2$/sr; mutant ER: $7\pm1.3\times10^3$ p/sec/cm$^2$/sr] (FIGS. 5a & 5b). The lower level of signal produced from the site implanted with the cells expressing the sensor with the wild type ER (N-RLUC-hER$_{281-549(Seq\,ID\,No.\,1)}$-C-RLUC)) is believed to be due to its higher affinity towards the endogenous ligand that occupies the expressed sensor protein before the availability of Raloxifene used for injection.

The Antiestrogen ICI182,780 Shows RLUC Complementation Signal That is Neither Like an Agonist nor Like an Antagonist.

Figure 6:
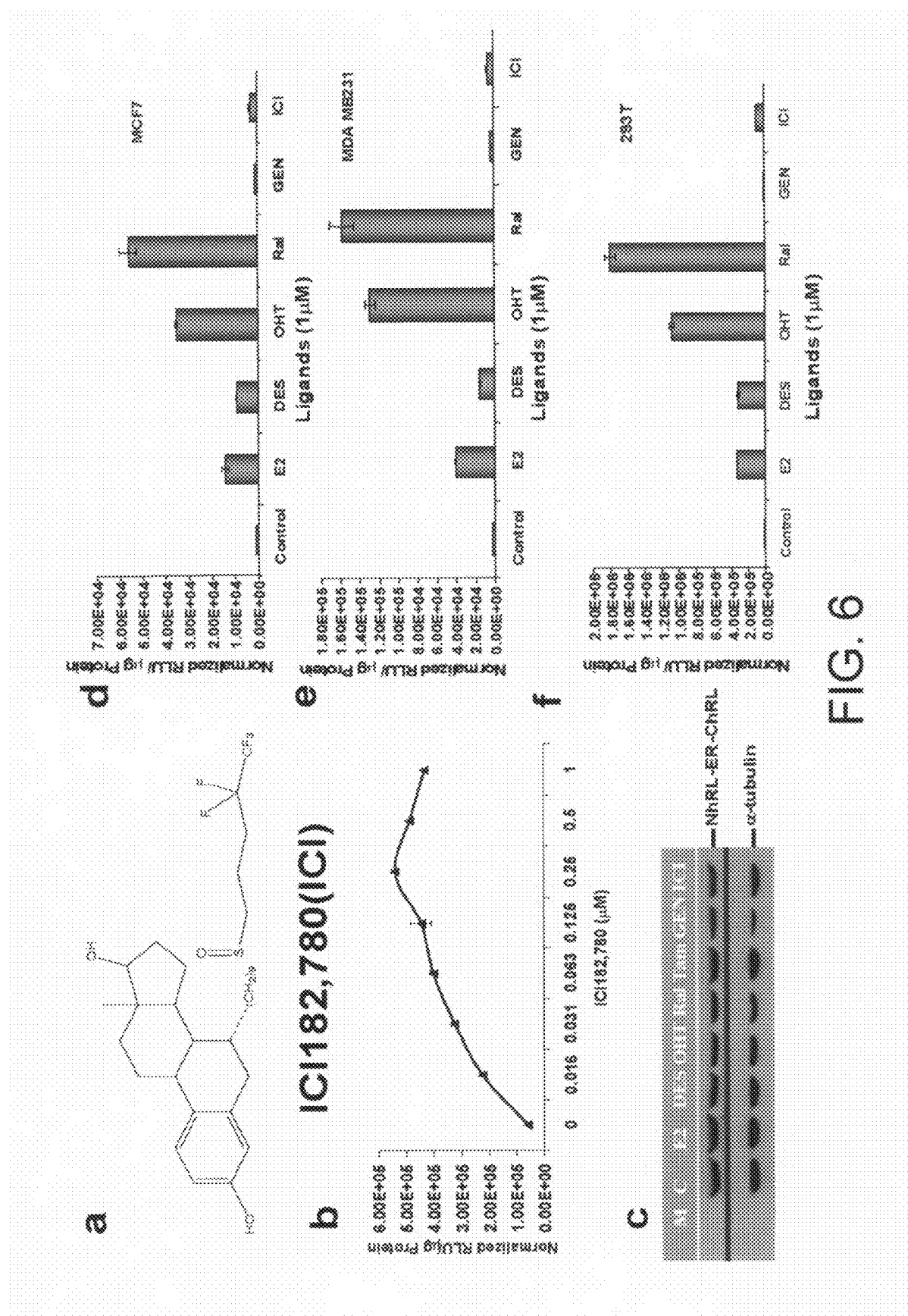
FIG. 6A illustrates the structure of ligand ICI182,780 used for the study.
FIG. 6B illustrates the ICI182,780 concentration-dependent RLUC complementation studied in 293T cells transiently transfected to express fusion protein N-RLUC-hER$_{281-549(Seq\ ID\ No.\ 1)}$-C-RLUC.
FIG. 6C illustrates the western blot analysis of cells transfected to express N-RLUC-hER$_{281-549(Seq\ ID\ No.\ 1)}$-C-RLUC treated with different ligands along with ICI182,780.
FIGS. 6D through 6F illustrate the ligand-induced intramolecular folding by different ligands in comparison with ICI182,780 studied in transiently transfected ER positive MCF7, ER negative MDA MB231 breast cancer cells, and in 293T human embryonic kidney cancer cells. The error bars are the SEM of triplicate determinations.

The drug ICI182,780 is a pure antiestrogen that is currently in clinical use for the treatment of both estrogen positive and negative breast cancer tumor progression. Even though many studies have been reported on the efficiency of this drug against cancer progression and its action on different tissues, no reports have been published on the pattern of structural folding induced by this drug on the ER-LBD. Hence the system described in this example was used for analyzing the complementation pattern induced by this drug. 293T cells transfected to express fusion protein chimera containing RLUC fragments with ER of amino acids 281-549 (SEQ. ID No: 1) (FIG. 6) and 281-595 (SEQ. ID No: 2) (data not shown) were used for this example. The result shows that the RLUC signal through intramolecular folding induced by this drug is not similar to either antagonists or agonists (FIG. 6d-6f). Even though the reported literature shows the induction of ER-1 protein degradation by the drug ICI 182,780 with long exposure times, the fusion sensor protein expressed in 293T cells in this study shows no significant level of degradation by Western blot analysis (FIG. 6c).

Ligand Induced Intramolecular Folding of Estrogen Receptor Studied in Different ER Positive and ER Negative Cell Lines Shows No Significant Relation With the Intracellular ER Level.

To study the agonist and antagonist specific intramolecular folding of estrogen receptor, the cells transfected with the vector construct to express fusion protein N-RLUC-hER$_{281-549(Seq\,ID\,No.\,1)}$-C-RLUC were studied in 293T, MCF7 and MDA-MB231 cells. The complemented RLUC activities were assayed before and after exposing to 1 µM concentrations of different ER ligands. The result shows significant (p<0.001) level of complemented *Renilla* Luciferase activity from the cells exposed to ligand antagonists 4-hydroxytamoxifen (80±15), Tamoxifen (60±5) and Raloxifene (80±10). The cells transfected and treated with agonist 17β-estradiol showed activity that is only 15±5 times more than cells before exposed to ligand. The cells transfected and induced with non-estrogen binding anticancer drugs Cisplatinum, Epigallocatechin gallate and Doxirubicin shows signal that is not significantly different from cells transfected and not exposed to any ligands (FIGS. 4a, 6d-6f).

Discussion hER intramolecular folding sensors were validated that can be efficiently used to screen ER ligands, and also a separate sensor that can distinguish agonists from antagonists of ER-ligands was developed. These sensors have the advantage that they can be directly translated from cell assays to molecular imaging of small living subjects. This study was designed to exploit the property of helix H12 rotation in achieving an intramolecular folding sensor in which a split reporter complementation strategy is employed to detect changes in the structural folding. This system specifically leads to split RLUC complementation if the ligand binding with the ER is an antagonist and at the same time it leads to low and no complementation for ligands that are agonists and partial agonists, respectively. Intramolecular folding sensors with various ligands in transiently and stably transfected cells were validated. To overcome the issue of extending the sensor system to living animals by specifically avoiding endogenous estrogen (17β-estradiol) binding to the receptor, a mutant form of hER was identified. This mutant G521T sensor well preserves the ability to distinguish antagonists from agonists, while not being limited by endogenous circulating ligand.

There is currently no non-transcriptional assay available that can easily distinguish between agonists and antagonists of ER. The existing strategies can only provide information about the binding of a ligand to ER, but not determine if the ligand is an agonist or antagonist. A non-transcriptional assay containing fusion chimeras of either Flp recombinase or Cre recombinase with a truncated mouse ER has been used for regulating the recombination of reporter genes in cells and living animals. This system has shown to be activated by both agonists and antagonists. Unfortunately, the activity generated by this system is significantly high even before the addition of ligand. Moreover, a small amount of recombinase enzyme is enough to produce a significant level of recombination through enzymatic amplification both in cells and in vivo in living animals. From the present study, a complement fusion chimera generated by fusing a truncated version of hER (amino acids 281-595, SEQ. ID No: 2) with Firefly Luciferase enzyme generated luciferase activity that is $10^4$ fold greater than background even before the addition of ligands. The addition of a ligand (both agonists and antagonists) generated activity that is only five to six-fold more than without drug (unpublished data).

To our knowledge, only one study has reported the construction of a mutant version of hER (hER$_{251-595/G521R}$ (SEQ. ID No: 13) and hER$_{251-595/G521V}$ (SEQ. ID No: 14)) for selective ligand binding by a fusion chimera containing hER$_{251-595}$ (SEQ. ID No: 3, amino acids 251-595) with Flp recombinase enzyme. The same mutants generated from the current study using the RLUC complementation system showed near-complete abolishment (hERG$_{521R}$) and significant reduction of all agonists activities (hERG$_{521V}$). Unlike the mouse ER, this mutation for the human ER showed only 3-5% receptor mediated RLUC complementation for the antagonist 4-hydroxytamoxifen. Even though the system does not behave like the mouse ER-LBD, this result clearly demonstrates the site at amino acid position 521 of hER is important for maintaining the ligand binding properties. Hence, mutants at position 521 with all possible 20 different amino acids were constructed. It was found that the replacement of amino acid glycine at 521 with threonine (T) showed nearly complete abolishment of the 17β-estradiol binding property of hER with only 10 to 20% reduction for all other ligands. Therefore, cells transfected with the vector constructed to express fusion chimera containing N-RLUC-hER$_{281-549/G521T(Seq\,ID\,No.\,12)}$-C-RLUC of hER were used for our small animal imaging studies.

The advantages of the intramolecular folding sensor assay developed in this study over all other previously reported systems are, at least: (1) it is real-time and quantitative, (2) it generates signal that can distinguish agonists from antagonists, (3) it is useful to study and image ligand binding to human ER in living animal models, (4) it is rapid and therefore allows for a high throughput strategy for screening/comparing different drugs in many cell lines, (5) it allows transition from cell culture to living subjects using the same assay because it is based on a bioluminescence split reporter that is compatible for both, and (6) it allows applications using transgenic models incorporating the sensor. In addition, the availability of other split reporters with different properties and substrate specificity will make this strategy useful in multiplexing with other reporter assays. It appears that this is the first time a system has been developed to image the signal generated during the direct binding of ligands to hER in living small animals excluding through downstream activations.

Materials and Methods

Chemicals, Enzymes and Reagents.

Restriction and modification enzymes and ligase were from New England Biolabs (Beverly, Mass.). TripleMaster Taq DNA polymerase from Brinkmann Eppendorf (Hamburg, Germany) was used for the PCR amplification of different fragments of the reporter gene *Renilla* Luciferase (rluc) and the genes for estrogen receptor alpha of human (hERα/HE0). The plasmid pCMV-hRL from Promega (Madison, Wis.) was used as template for the amplification of reporter fragments used in this study. Different estrogen receptor antagonists and agonists include Tamoxifen, 4-hydroxytamoxifen, Raloxifene, Diethylstilbestrol, 17β-estradiol, Genistein, anticancer cancer drugs Cisplatinum and Epigallocatechin gallate (green tea), and antibiotics for bacterial cultures were purchased from Sigma (St. Louis, Mo.). Lipofectamine transfection reagent was from Invitrogen (Carlsbad, Calif. 92008). The plasmid and DNA gel extraction kits were purchased from Qiagen (Valencia, Calif.). Coelenterazine was from Nanolight (Pinetop, Ariz.). Bacterial culture media were from BD Diagnostic Systems (Sparks, Md.). All cell culture media, fetal bovine serum, the antibiotics streptomycin, and penicillin, were from Invitrogen (Carlsbad, Calif.). The anti-estrogen drug ICI 182, 780 was from Tocris Cookson Inc., (Ballwin, Mo.). The custom oligonucleotides synthesized from Stanford Protein and Nucleic acid facility were used as primers for the amplification of receptors, reporters and for making different peptide linkers. The site directed mutagenesis kit from Stratagene (La Jolla, Calif.) was used for constructing the mutant ligand-binding domain of human estrogen receptor. The sequences all the constructs were verified by sequencing at Stanford PAN facility.

Construction of Different Plasmid Vectors.

The plasmid vector pcDNA-N-rluc-FRB was used as the starting vector. The C-rluc fragment was amplified using forward primer designed with Bam HI restriction enzyme site and the reverse primer with stop codon and Xho I restriction enzyme site. The amplified fragment was digested with respective enzymes and inserted into the same enzyme digested pcDNA-N-rluc-FRB that releases the FRB fragment, and constructed pcDNA-N-rluc-C-rluc. Different length fragments of human estrogen receptor were PCR amplified using the forward and reverse primers designed with Bam HI restriction enzyme site on either side. The amplified fragments were inserted into the same enzyme-digested, dephosphorylated pcDNA-N-rluc-C-rluc backbone and constructed pcDNA-N-rluc-ER-C-rluc. The Stratagene site directed mutagenesis kit was used to construct the vector containing the mutant form of human ER (FIGS. 2*a*, 5*a* & *b*, and 7*a*).

Cell Cultures.

Human 293T embryonic kidney cancer cells (ATCC, Manassas, Va.) were grown in MEM supplemented with 10% FBS and 1% penicillin/streptomycin solution. The MCF7 human breast cancer cells were grown in DMEM high glucose supplemented with 10% FBS and 1% penicillin/streptomycin. Estrogen receptor negative MDA-MB231 cells were maintained in DMEM high glucose medium supplemented with 10% FBS and 1% penicillin/streptomycin.

Cell Transfection and Luciferase Assay.

Transfections were performed in 80% confluent 24-hour old cultures of 293T, MCF7 and MDA-MB 231 cells. For transfection, 200 ng DNA/well were used in 12 well culture plates. Volumes of Lipofectamine were as recommended by the manufacturer. The co-transfection of 10 ng/well Fluc DNA served as control for normalizing transfection. The cells were assayed after 18 hours of incubation at 37° C. with 5% $CO_2$. The luminometry assay for *Renilla* Luciferase activity was performed as per protocol published previously. In brief, the cells were lysed in 200 μl of 1× passive lysis buffer (Promega, Madison, Wis.) by shaking for 15 min at room temperature. The cell lysates were centrifuged for 5 min at 10,000 rpm at 4° C. Twenty μl of supernatants were assayed by adding 1 μg of substrate coelenterazine in 100 μl of 0.05M sodium phosphate buffer (pH 7.0) followed by photon counting in the luminometer (Turner Designs, model T 20/20, Sunnyvale, Calif.) for 10 s. The readings were normalized by measuring the protein concentration in the cell lysates and also by measuring the FLUC activity. Activity of RLUC was represented as normalized relative light units (RLU) per microgram of protein.

The Ligands Concentration Dependent Intramolecular Folding Study.

To study the concentration of different agonists and antagonists of estrogen receptor that is needed for inducing efficient intramolecular folding, 293T cells transiently transfected with pcDNA-N-rluc-hER$_{281-549(Seq\ ID\ No.\ 1)}$-C-rluc were exposed to four different ligands, including 17β-estradiol, Raloxifene, Tamoxifen, Diethylstilbestrol, 4-hydroxytamoxifen and Genistein, at six different concentrations (0, 250, 500, 750, 1000, and 1500 μM). The cells were assayed for RLUC activity after 18 hours of incubation. The results were normalized as mentioned in the previous experiments.

Western Blot Analysis Using Anti-ER and Anti-RLUC Antibodies.

To study the impact of different ligands in the expression of cellular estrogen receptor levels, the MCF7 cells exposed to 1 μM concentration of different ligands (17β-estradiol, Diethylstilbestrol, Genistein, Tamoxifen and Raloxifene) with control exposed to solvent DMSO were blotted using the antibody raised against estrogen receptor alpha. For that 10 μg protein resolved in 4-12% gradient SDS-PAGE was transferred to nitrocellulose membrane. The membrane was blocked with TBST buffer containing 5% non-fat milk powder for 3 hours. The membrane was further incubated in the same buffer containing anti-ERα antibody over night at 4° C. with constant shaking. The membrane was washed and incubated with secondary anti-mouse antibody conjugated with HRP enzyme for 2 hours. The washed membrane was incubated with chemiluminescent HRP substrate and exposed to X-ray film for 2 minutes and developed. The same membrane was stripped and probed for β-actin as internal control. Similarly, to study the impact of different ligands in the expression level of transgene and its associated RLUC complementation, the 293T cells transiently transfected with pcDNA-N-rluc-hER$_{281-549}$-C-rluc were exposed to 1 μM concentration of ligands 17β-estradiol, Diethylstilbestrol, Genistein, Tamoxifen, and Raloxifene for 18 hours, and the protein isolated from the lysed cells was used for Western blot analysis using anti-RLUC antibody by performing steps described above.

Ligand-induced Intramolecular Folding of hER$_{281-549}$ (SEQ. ID No: 1) and its Associated RLUC Complementation at Different Time Points Studied.

To study the time point at which various ligands can induce maximum-fold, ligand-induced RLUC complementation, 293T cells were transiently transfected with pcDNA-N-rluc-hER$_{281-549(Seq\ ID\ No.\ 1)}$-C-rluc and exposed to 1 μM concentration of three different ligands, including 17β-estradiol, 4-hydroxytamoxifen and Diethylstilbestrol. The cells were assayed at four different time points after exposure to ligands (6, 12, 18 and 24 hours). The results were normalized as mentioned in the previous experiments.

Studying the Competitive Binding of Estrogen Receptor Agonists and Antagonists in Generating the Intramolecular Folding Assisted RLUC Complementation.

The 293T cells transiently transfected to express the fusion protein N-RLUC-hER$_{281-549(Seq\ ID\ No.\ 1)}$-C-RLUC were used for this study. The agonist 17β-estradiol and the antagonist Tamoxifen were used for this study. In one experiment cells were exposed to 1 μM fixed concentration of agonist 17β-estradiol with different concentrations of antagonist Tamoxifen (0.008 to 2 μM). The cells were assayed for complementing RLUC activity after 18 hours of incubation at 37° C. Similarly, the cells were exposed to a fixed concentration of antagonist Tamoxifen (1 μM) with different concentrations of agonist 17β-estradiol (0 to 1 μM) and assayed for RLUC activity.

The Ligand Agonists and Antagonists Specific Intramolecular Folding Studies in ER Positive and Negative Cells Lines.

The ligand agonists and antagonists specific intramolecular folding were studied in ER positive and negative cell lines. For this study, 1 μM final concentration of different drugs dissolved in DMSO were added immediately after transfection with pcDNA-N-rluc-hER$_{281-549(Seq\ ID\ No.\ 1)}$-C-rluc, and assayed for complemented RLUC activity after 18 hours. The cells exposed to solvent DMSO served as control. The same samples were analysed by Western blot for the detection of the transfected protein level using anti-RLUC antibody using the method mentioned above.

Stable 293T Cells Expressing N-RLUC-hER$_{281-549(Seq\ ID\ No.\ 1)}$-C-RLUC, N-RLUC-mutant hER$_{281-549(Seq\ ID\ No.\ 1)}$-C-RLUC (for in Vivo Imaging Studies).

To make 293T cells stably expressing the fusion protein containing N- and C-rluc fragments with mutant and wild type mouse ER, the cells were transfected with respective vectors and selected using puromycin antibiotic markers for repeated passages until getting stable clone. The selected resistant cells were propagated and studied for the RLUC complementation using different ligands used in the transient studies. The stable clones were further used for imaging studies in living mice.

Optical CCD Imaging of Estrogen Receptor Ligand-induced Intramolecular Folding in Living Mice.

All animal handling was performed in accordance with Stanford University Animal Research Committee guidelines. For imaging in living nude mice (nu/nu) stable 293T cells expressing fusion proteins N-RLUC-hER$_{281-549(Seq\ ID\ No.\ 1)}$-C-RLUC and N-RLUC-mutant-hER$_{281-549(Seq\ ID\ No.\ 1)}$-C-RLUC were used. Mice were anesthetized by i.p. injection of ≈40 μl of a ketamine and xylazine (4:1) solution and two million and five millions cells respectively of each were implanted on either side of the animals' hind limbs. The animals were imaged immediately and 18 hours after injecting antagonist Raloxifene (0.5 mg/animal). To image *Renilla* Luciferase activity, 100 μl of coelenterazine (50 μg) was injected via tail vein 5 sec before imaging. All mice (N=6) were imaged using a cooled charge coupled device (CCD) camera (Xenogen IVIS; Xenogen Corp. Alameda, Calif.) and photons emitted from the mice were collected and integrated for a period of 5 min. Images were obtained using Living Image software (Xenogen) and Igor image analysis software (Wavemetric, Oreg.). To quantify the measured light, regions of interest were drawn over the area of the implanted cells and the maximum photons/sec/cm$^2$/steradian (sr) were obtained as validated previously.

```
Sequences
SEQ ID No. 1, Human estrogen receptor-alpha ligand binding domain amino acids
281-549 (e.g., to distinguish ER-ligands)
GSAGDMRAANLWPSPLMIKRSKKNSLALSLTADQMVSALLDAEPPILYSEYDPTRPFSEASMMGLLTNLADRELVHM

INWAKRVPGFVDLTLHDQVHLLECAWLEILMIGLVWRSMEHPVKLLFAPNLLLDRNQGKCVEGMVEIFDMLLATSSR

FRMMNLQGEEFVCLKSIILLNSGVYTFLSSTLKSLEEKDHIHRVLDKITDTLIHLMAKAGLTLQQQHQRLAQLLLIL

SHIRHMSNKGMEHLYSMKCKNVVPLYDLLLEMLDAHRL

SEQ ID No. 2, Human estrogen receptor-alpha ligand binding domain amino acids
281-595 (e.g., to identify ER-ligands)
GSAGDMRAANLWPSPLMIKRSKKNSLALSLTADQMVSALLDAEPPILYSEYDPTRPFSEASMMGLLTNLADRELVHM

INWAKRVPGFVDLTLHDQVHLLECAWLEILMIGLVWRSMEHPVKLLFAPNLLLDRNQGKCVEGMVEIFDMLLATSSR

FRMMNLQGEEFVCLKSIILLNSGVYTFLSSTLKSLEEKDHIHRVLDKITDTLIHLMAKAGLTLQQQHQRLAQLLLIL

SHIRHMSNKGMEHLYSMKCKNVVPLYDLLLEMLDAHRLHAPTSRGGASVEETDQSHLATAGSTSSHSLQKYYITGEA

EGFPATV

SEQ ID No. 3, Human estrogen receptor-alpha amino acids 1-595 (e.g., to study
ER-homodimerization)
MTMTLHTKASGMALLHQIQGNELEPLNRPQLKIPLERPLGEVYLDSSKPAVYNYPEGAAYEFNAAAAANAQVYGQTG

LPYGPGSEAAAFGSNGLGGFPPLNSVSPSPLMLLHPPPQLSPFLQPHGQQVPYYLENEPSGYTVREAGPPAFYRPNS

DNRRQGGRERLASTNDKGSMAMESAKETRYCAVCNDYASGYHYGVWSCEGCKAFFKRSIQGHNDYMCPATNQCTIDK

NRRKSCQACRLRKCYEVGMMKGGIRKDRRGGRMLKHKRQRDDGEGRGEVGSAGDMRAANLWPSPLMIKRSKKNSLAL

SLTADQMVSALLDAEPPILYSEYDPTRPFSEASMMGLLTNLADRELVHMINWAKRVPGFVDLTLHDQVHLLECAWLE

ILMIGLVWRSMEHPVKLLFAPNLLLDRNQGKCVEGMVEIFDMLLATSSRFRMMNLQGEEFVCLKSIILLNSGVYTFL
```

-continued

SSTLKSLEEKDHIHRVLDKITDTLIHLMAKAGLTLQQQHQRLAQLLLILSHIRHMSNKGMEHLYSMKCKNVVPLYDL

LLEMLDAHRLHAPTSRGGASVEETDQSHLATAGSTSSHSLQKYYITGEAEGFPATV

SEQ ID No. 4, Mouse estrogen receptor ligands binding amino acids 281-549
(e.g., to distinguish ER-ligands)
RNEMGASGDMRAANLWPSPLVIKHTKKNSPALSLTADQMVSALLDAEPPMIYSEYDPSRPFSEASMMGLLTNLADRE

LVHMINWAKRVPGFGDLNLHDQVHLLECAWLEILMIGLVWRSMEHPGKLLFAPNLLLDRNQGKCVEGMVEIFDMLLA

TSSRFRMMNLQGEEFVCLKSIILLNSGVYTFLSSTLKSLEEKDHIHRVLDKITDTLIHLMAKAGLTLQQQHRRLAQL

LLILSHIRHMSNKG MEHLY NMKCKNVVPL YDLLLEMLD

SEQ ID No. 5, Mouse estrogen receptor ligands binding amino acids 281-599
(e.g., to identify ER-ligands)
RNEMGASGDMRAANLWPSPLVIKHTKKNSPALSLTADQMVSALLDAEPPMIYSEYDPSRPFSEASMMGLLTNLADRE

LVHMINWAKRVPGFGDLNLHDQVHLLECAWLEILMIGLVWRSMEHPGKLLFAPNLLLDRNQGKCVEGMVEIFDMLLA

TSSRFRMMNLQGEEFVCLKSIILLNSGVYTFLSSTLKSLEEKDHIHRVLDKITDTLIHLMAKAGLTLQQQHRRLAQL

LLILSHIRHMSNKG MEHLY NMKCKNVVPL YDLLLEMLDA HRLHAPASRM GVPPEEPSQT QLATTSSTSA

HSLQTYYIPP EAEGFPNTI

SEQ ID No. 6, Mouse estrogen receptor amino acids 1-599 (e.g., to study
homodimerization)
MTMTLHTKASGMALLHQIQGNELEPLNRPQLKMPMERALGEVYVDNSKPTVFNYPEGAAYEFNAAAAAAAASAPVY

GQSGIAYGPGSEAAAFSANSLGAFPQLNSVSPSPLMLLHPPPQLSPFLHPHGQQVPYYLENEPSAYAVRDTGPPAFY

RSNSDNRRQNGRERLSSSNEKGNMIMESAKETRYCAVCNDYASGYHYGVWSCEGCKAFFKRSIQGHNDYMCPATNQC

TIDKNRRKSCQACRLRKCYEVGMMKGGIRKDRRGGRMLKHKRQRDDLEGRNEMGASGDMRAANLWPSPLVIKHTKKN

SPALSLTADQMVSALLDAEPPMIYSEYDPSRPFSEASMMGLLTNLADRELVHMINWAKRVPGFGDLNLHDQVHLLEC

AWLEILMIGLVWRSMEHPGKLLFAPNLLLDRNQGKCVEGMVEIFDMLLATSSRFRMMNLQGEEFVCLKSIILLNSGV

YTFLSSTLKSLEEKDHIHRVLDKITDTLIHLMAKAGLTLQQQHRRLAQLLLILSHIRHMSNKG MEHLY

NMKCKNVVPL YDLLLEMLDA HRLHAPASRM GVPPEEPSQT QLATTSSTSA HSLQTYYIPP EAEGFPNTI

SEQ ID No. 7, Renilla Luciferase protein:
MASKVYDPEQ RKRMITGPQW WARCKQMNVL DSFINYYDSE KHAENAVIFL HGNAASSYLWRHVVPHIEPV

ARCIIPDLIG MGKSGKSGNG SYRLLDHYKY LTAWFELLNL PKKIIFVGHD WGACLAFHYS YEHQDKIKAI

VHAESVVDVI ESWDEWPDIE EDIALIKSEE GEKMVLENNFFVETMLPSKI MRKLEPEEFA AYLEPFKEKG

EVRRPTLSWP REIPLVKGGK PDVVQIVRNY NAYLRASDDL PKMFIESDPG FFSNAIVEGA KKFPNTEFVK

VKGLHFSQEDAPDEMGKYIKSFVERVLKNEQ

SEQ ID No. 8, Double mutant (C124A/M185V) Renilla Luciferase protein:
MASKVYDPEQ RKRMITGPQW WARCKQMNVL DSFINYYDSE KHAENAVIFL HGNAASSYLWRHVVPHIEPV

ARCIIPDLIG MGKSGKSGNG SYRLLDHYKY LTAWFELLNL PKKIIFVGHDWGAALAFHYS YEHQDKIKAI

VHAESVVDVI ESWDEWPDIE EDIALIKSEE GEKMVLENNF FVETVLPSKI MRKLEPEEFA AYLEPFKEKG

EVRRPTLSWP REIPLVKGGK PDVVQIVRNYNAYLRASDDL PKMFIESDPG FFSNAIVEGA KKFPNTEFVK

VKGLHFSQED APDEMGKYIKSFVERVLKNE Q

SEQ ID No. 9, Mutated (8) Renilla Luciferase protein:
MASKVYDPEQ RKRMITGPQW WARCKQMNVL DSFINYYDSE KHAENAVIFL HGNATSSYLW RHVVPHIEPV

ARCIIPDLIG MGKSGKSGNG SYRLLDHYKY LTAWFELLNL PKKIIFVGHD WGAALAFHYA YEHQDRIKAI

VHMESVVDVI ESWDEWPDIE EDIALIKSEE GEKMVLENNF FVETVLPSKI MRKLEPEEFA AYLEPFKEKG

EVRRPTLSWP REIPLVKGGK PDVVQIVRNY NAYLRASDDL PKLFIESDPG FFSNAIVEGA KKFPNTEFVK

VKGLHFLQED APDEMGKYIK SFVERVLKNE Q

-continued

SEQ. ID No. 10, Nucleotide sequence of full length Firefly Luciferase
(corresponding to amino acids 1-550)
atggaagacgccaaaaacataaagaaaggcccggcgccattctatccgctggaagatggaaccgctggagagcaact gcataaggctatgaagagatacgccctggttcctggaacaattgcttttacagatgcacatatcgaggtggacatca cttacgctgagtacttcgaaatgtccgttcggttggcagaagctatgaaacgatatgggctgaatacaaatcacaga atcgtcgtatgcagtgaaaactctcttcaattctttatgccggtgttgggcgcgttatttatcggagttgcagttgc gcccgcgaacgacatttataatgaacgtgaattgctcaacagtatgggcatttcgcagcctaccgtggtgttcgttt ccaaaaaggggttgcaaaaaattttgaacgtgcaaaaaaagctcccaatcatccaaaaaattattatcatggattct aaaacggattaccagggatttcagtcgatgtacacgttcgtcacatctcatctacctcccggttttaatgaatacga ttttgtgccagagtccttcgatagggacaagacaattgcactgatcatgaactcctctggatctactggtctgccta aaggtgtcgctctgcctcatagaactgcctgcgtgagattctcgcatgccagagatcctattttttggcaatcaaatc attccggatactgcgattttaagtgttgttccattccatcacggttttggaatgtttactacactcggatatttgat atgtggatttcgagtcgtcttaatgtatagatttgaagaagagctgtttctgaggagccttcaggattacaagattc aaagtgcgctgctggtgccaaccctattctccttcttcgccaaaagcactctgattgacaaatacgatttatctaat ttacacgaaattgcttctggtggcgctcccctctctaaggaagtcggggaagcggttgccaagaggttccatctgcc aggtatcaggcaaggatatgggctcactgagactacatcagctattctgattacacccgaggggatgataaaccgg gcgcggtcggtaaagttgttccatttttttgaagcgaaggttgtggatctggataccgggaaaacgctgggcgttaat caaagaggcgaactgtgtgtgagaggtcctatgattatgtccggttatgtaaacaatccggaagcgaccaacgcctt gattgacaaggatggatggctacattctggagacatagcttactgggacgaagacgaacacttcttcatcgttgacc gcctgaagtctctgattaagtacaaaggctatcaggtggctcccgctgaattggaatccatcttgctccaacacccc aacatcttcgacgcaggtgtcgcaggtcttcccgacgatgacgccggtgaacttcccgccgccgttgttgttttgga gcacggaaagacgatgacggaaaaagagatcgtggattacgtcgccagtcaagtaacaaccgcgaaaaagttgcgcg gaggagttgtgtttgtggacgaagtaccgaaaggtcttaccggaaaactcgacgcaagaaaaatcagagagatcctc ataaaggccaagaagggcggaaagatcgccgtgtaa SEQ ID No. 11, Mutant human estrogen receptor amino acids 1-595 (G521T)
MTMTLHTKASGMALLHQIQGNELEPLNRPQLKIPLERPLGEVYLDSSKPAVYNYPEGAAYEFNAAAAANAQVYGQTG

LPYGPGSEAAAFGSNGLGGFPPLNSVSPSPLMLLHPPPQLSPFLQPHGQQVPYYLENEPSGYTVREAGPPAFYRPNS

DNRRQGGRERLASTNDKGSMAMESAKETRYCAVCNDYASGYHYGVWSCEGCKAFFKRSIQGHNDYMCPATNQCTIDK

NRRKSCQACRLRKCYEVGMMKGGIRKDRRGGRMLKHKRQRDDGEGRGEVGSAGDMRAANLWPSPLMIKRSKKNSLAL

SLTADQMVSALLDAEPPILYSEYDPTRPFSEASMMGLLTNLADRELVHMINWAKRVPGFVDLTLHDQVHLLECAWLE

ILMIGLVWRSMEHPVKLLFAPNLLLDRNQGKCVEGMVEIFDMLLATSSRFRMMNLQGEEFVCLKSIILLNSGVYTFL

SSTLKSLEEKDHIHRVLDKITDTLIHLMAKAGLTLQQQHQRLAQLLLILSHIRHMSNKTMEHLYSMKCKNVVPLYDL

LLEMLDAHRLHAPTSRGGASVEETDQSHLATAGSTSSHSLQKYYITGEAEGFPATV

SEQ ID No. 12, Mutant human estrogen receptor ligand binding domain amino
acids 281-595 (G521T)
GSAGDMRAANLWPSPLMIKRSKKNSLALSLTADQMVSALLDAEPPILYSEYDPTRPFSEASMMGLLTNLADRELVHM

INWAKRVPGFVDLTLHDQVHLLECAWLEILMIGLVWRSMEHPVKLLFAPNLLLDRNQGKCVEGMVEIFDMLLATSSR

FRMMNLQGEEFVCLKSIILLNSGVYTFLSSTLKSLEEKDHIHRVLDKITDTLIHLMAKAGLTLQQQHQRLAQLLLIL

SHIRHMSNKTMEHLYSMKCKNVVPLYDLLLEMLDAHRLHAPTSRGGASVEETDQSHLATAGSTSSHSLQKYYITGEA

EGFPATV

SEQ ID No. 13, Mutant human estrogen receptor ligand binding domain amino
acids 281-595 (G521R)
GSAGDMRAANLWPSPLMIKRSKKNSLALSLTADQMVSALLDAEPPILYSEYDPTRPFSEASMMGLLTNLADRELVHM

INWAKRVPGFVDLTLHDQVHLLECAWLEILMIGLVWRSMEHPVKLLFAPNLLLDRNQGKCVEGMVEIFDMLLATSSR

-continued

FRMMNLQGEEFVCLKSIILLNSGVYTFLSSTLKSLEEKDHIHRVLDKITDTLIHLMAKAGLTLQQQHQRLAQLLLIL

SHIRHMSNKRMEHLYSMKCKNVVPLYDLLLEMLDAHRLHAPTSRGGASVEETDQSHLATAGSTSSHSLQKYYITGEA

EGFPATV

SEQ ID No. 14, Mutant human estrogen receptor ligand binding domain amino
acids 281-595 (G521V)
GSAGDMRAANLWPSPLMIKRSKKNSLALSLTADQMVSALLDAEPPILYSEYDPTRPFSEASMMGLLTNLADRELVHM

INWAKRVPGFVDLTLHDQVHLLECAWLEILMIGLVWRSMEHPVKLLFAPNLLLDRNQGKCVEGMVEIFDMLLATSSR

FRMMNLQGEEFVCLKSIILLNSGVYTFLSSTLKSLEEKDHIHRVLDKITDTLIHLMAKAGLTLQQQHQRLAQLLLIL

SHIRHMSNKVMEHLYSMKCKNVVPLYDLLLEMLDAHRLHAPTSRGGASVEETDQSHLATAGSTSSHSLQKYYITGEA

EGFPATV

SEQ ID No. 15, linker
GGGGSGGGGS

SEQ ID No. 16, linker
GGGGSGGGGSGGGGS

SEQ ID No. 17, full length Firefly Luciferase amino acid sequence
MEDAKNIKKGPAPFYPLEDGTAGEQLHKAMKRYALVPGTIAFTDAHIEVDITYAEYFEMSVRLAEAMKRYGLNTNHR

IVVCSENSLQFFMPVLGALFIGVAVAPANDIYNERELLNSMGISQPTVVFVSKKGLQKILNVQKKLPIIQKIIIMDS

KTDYQGFQSMYTFVTSHLPPGFNEYDFVPESFDRDKTIALIMNSSGSTGLPKGVALPHRTACVRFSHARDPIFGNQI

IPDTAILSVVPFHHGFGMFTTLGYLICGFRVVLMYRFEEELFLRSLQDYKIQSALLVPTLFSFFAKSTLIDKYDLSN

LHEIASGGAPLSKEVGEAVAKRFHLPGIRQGYGLTETTSAILITPEGDDKPGAVGKVVPFFEAKVVDLDTGKTLGVN

QRGELCVRGPMIMSGYVNNPEATNALIDKDGWLHSGDIAYWDEDEHFFIVDRLKSLIKYKGYQVAPAELESILLQHP

NIFDAGVAGLPDDDAGELPAAVVVLEHGKTMTEKEIVDYVASQVTTAKKLRGGVVFVDEVPKGLTGKLDARKIREIL

IKAKKGGKIAV

SEQ ID No. 18, Nucleotide sequence corresponding to NLUC-1-475 fragment
atggaagacgccaaaaacataaagaaaggcccggcgccattctatcctctagaggatggaaccgctggagagcaact gcataaggctatgaagagatacgcccggttcctggaacaattgcttttacagatgcacatatcgaggtgaacatca cgtacgcggaatacttcgaaatgtccgttcggttggcagaagctatgaaacgatatgggctgaatacaaatcacaga atcgtcgtatgcagtgaaaactctcttcaattctttatgccggtgttgggcgcgttatttatcggagttgcagttgc gcccgcgaacgacatttataatgaacgtgaattgctcaacagtatgaacatttcgcagcctaccgtagtgtttgttt ccaaaaaggggttgcaaaaaattttgaacgtgcaaaaaaaattaccaataatccagaaaattattatcatgattct aaaacggattaccagggatttcagtcgatgtacacgttcgtcacatctcatctacctcccggttttaatgaatacga ttttgtaccagagtcctttgatcgtgacaaaacaattgcactgataatgaattcctctggatctactgggttaccta agggtgtggcccttccgtcatagagctgcctgcgtcagattctcgcatgccagagatcctatttttggcaatcaaat cgctccggatactgcgattttaagtgttgttccattccatcacggttttggaatgtttactacactcggatatttga tatgtggatttcgagtcgtcttaatgtatagatttgaagaagagctgtttttacgatcccttcaggattacaaaatt caaagtgcgttgctagtaccaacccctatttttcattcctggccaaaagcactctgattgacaaatacgatttatctaa tttacacgaaattgcttctgggggcgcacctctttcgaaagaagtcggggaagcggttgcaaaacgcttccatcttc cagggatacgacaaggatatgggctcactgagactacatcagctattctgattacacccaaggggatgataaaccg ggcgcggtcggtaaagttgttccatttttttgaagcgaaggttgtggatctggataccgggaaaacgctgggcgttaa tcagagaggcgaattatgtgtcagaggacctatgattatgtccggttatgtaaacaatccggaagcgaccaacgcct tgattgacaaggatggatggctacattctggagacatagcttactgggacgaagacgaacacttcttcatagttgac cgcttgaagtctttaattaaatacaaaggatatcaggtggcccccgctgaattggaatcgatattgttacaacaccc caacatcttcgacgcgggcgtggcaggtcttcccgacgattaa -continued SEQ ID No. 19, Amino Acid sequence corresponding to NLUC-1-475 fragment
MEDAKNIKKGPAPFYPLEDGTAGEQLHKAMKRYALVPGTIAFTDAHIEVDITYAEYFEMSVRLAEAMKRYGLNTNHR

IVVCSENSLQFFMPVLGALFIGVAVAPANDIYNERELLNSMGISQPTVVFVSKKGLQKILNVQKKLPIIQKIIIMDS

KTDYQGFQSMYTFVTSHLPPGFNEYDFVPESFDRDKTIALIMNSSGSTGLPKGVALPHRTACVRFSHARDPIFGNQI

IPDTAILSVVPFHHGFGMFTTLGYLICGFRVVLMYRFEEELFLRSLQDYKIQSALLVPTLFSFFAKSTLIDKYDLSN

LHEIASGGAPLSKEVGEAVAKRFHLPGIRQGYGLTETTSAILITPEGDDKPGAVGKVVPFFEAKVVDLDTGKTLGVN

QRGELCVRGPMIMSGYVNNPEATNALIDKDGWLHSGDIAYWDEDEHFFIVDRLKSLIKYKGYQVAPAELESILLQHP

NIFDAGVAGLPDD

SEQ ID No. 20, Nucleotide sequence corresponding to CLUC-265-550 fragment
atgtatagatttgaagaagagctgtttctgaggagccttcaggattacaagattcaaagtgcgctgctggtgccaac cctattctccttcttcgccaaaagcactctgattgacaaatacgatttatctaatttacacgaaattgcttctggtg gcgctcccctctctaaggaagtcggggaagcggttgccaagaggttccatctgccaggtatcaggcaaggatatggg ctcactgagactacatcagctattctgattacacccgaggggatgataaaccgggcgcggtcggtaaagttgttcc attttttgaagcgaaggttgtggatctggataccgggaaaacgctgggcgttaatcaaagaggcgaactgtgtgtga gaggtcctatgattatgtccggttatgtaaacaatccggaagcgaccaacgccttgattgacaaggatggatggcta cattctggagacatagcttactgggacgaagacgaacacttcttcatcgttgaccgcctgaagtctctgattaagta caaaggctatcaggtggctcccgctgaattggaatccatcttgctccaacaccccaacatcttcgacgcaggtgtcg caggtcttcccgacgatgacgccggtgaacttcccgccgccgttgttgttttggagcacggaaagacgatgacggaa aaagagatcgtggattacgtcgccagtcaagtaacaaccgcgaaaaagttgcgcggaggagttgtgtttgtggacga agtaccgaaaggtcttaccggaaaactcgacgcaagaaaatcagagagatcctcataaaggccaagaagggcggaa agatcgccgtgtaa SEQ ID No. 21, Amino Acid sequence corresponding to CLUC-265-550 fragment
MYRFEEELFLRSLQDYKIQSALLVPTLFSFFAKSTLIDKYDLSNLHEIASGGAPLSKEVGEAVAKRFHLPGIRQGYG

LTETTSAILITPEGDDKPGAVGKVVPFFEAKVVDLDTGKTLGVNQRGELCVRGPMIMSGYVNNPEATNALIDKDGWL

HSGDIAYWDEDEHFFIVDRLKSLIKYKGYQVAPAELESILLQHPNIFDAGVAGLPDDDAGELPAAVVVLEHGKTMTE

KEIVDYVASQVTTAKKLRGGVVFVDEVPKGLTGKLDARKIREILIKAKKGGKIAV

SEQ ID No. 22, Nucleotide sequence corresponding to NLUC-1-398
atggaagacgccaaaaacataaagaaaggcccggcgccattctatccgctggaagatggaaccgctggagagcaact gcataaggctatgaagagatacgccctggttcctggaacaattgcttttacagatgcacatatcgaggtggacatca cttacgctgagtacttcgaaatgtccgttcggttggcagaagctatgaaacgatatgggctgaatacaaatcacaga atcgtcgtatgcagtgaaaactctcttcaattcttttatgccggtgttgggcgcgttatttatcggagttgcagttgc gcccgcgaacgacatttataatgaacgtgaattgctcaacagtatgggcatttcgcagcctaccgtggtgttcgttt ccaaaaaggggttgcaaaaaattttgaacgtgcaaaaaaagctcccaatcatccaaaaaattattatcatggattct aaaacggattaccagggatttcagtcgatgtacacgttcgtcacatctcatctacctcccggttttaatgaatacga ttttgtgccagagtccttcgatagggacaagacaattgcactgatcatgaactcctctggatctactggtctgccta aaggtgtcgctctgcctcatagaactgcctgcgtgagattctcgcatgccagagatcctatttttggcaatcaaatc attccggatactgcgattttaagtgttgttccattccatcacggttttggaatgtttactacactcggatatttgat atgtggatttcgagtcgtcttaatgtatagatttgaagaagagctgtttctgaggagccttcaggattacaagattc aaagtgcgctgctggtgccaacccctattctccttcttcgccaaaagcactctgattgacaaatacgatttatctaat ttacacgaaattgcttctggtggcgctcccctctctaaggaagtcggggaagcggttgccaagaggttccatctgcc aggtatcaggcaaggatatgggctcactgagactacatcagctattctgattacacccgaggggatgataaaccgg gcgcggtcggtaaagttgttccattttttgaagcgaaggttgtggatctggataccgggaaaacgctgggcgttaat caaagaggcgaactgtgtgtgagaggtcctatgattatg SEQ ID No. 23, amino acid sequence corresponding to NLUC-1-398
MEDAKNIKKGPAPFYPLEDGTAGEQLHKAMKRYALVPGTIAFTDAHIEVDITYAEYFEMSVRLAEAMKRYGLNTNHR

IVVCSENSLQFFMPVLGALFIGVAVAPANDIYNERELLNSMGISQPTVVFVSKKGLQKILNVQKKLPIIQKIIIMDS

KTDYQGFQSMYTFVTSHLPPGFNEYDFVPESFDRDKTIALIMNSSGSTGLPKGVALPHRTACVRFSHARDPIFGNQI

IPDTAILSVVPFHHGFGMFTTLGYLICGFRVVLMYRFEEELFLRSLQDYKIQSALLVPTLFSFFAKSTLIDKYDLSN

LHEIASGGAPLSKEVGEAVAKRFHLPGIRQGYGLTETTSAILITPEGDDKPGAVGKVVPFFEAKVVDLDTGKTLGVN

QRGELCVRGPMIM

SEQ ID No. 24, Nucleotide sequence corresponding to CLUC-398-550
tccggttatgtaaacaatccggaagcgaccaacgccttgattgacaaggatggatggctacattctggagacatagc ttactgggacgaagacgaacacttcttcatcgttgaccgcctgaagtctctgattaagtacaaaggctatcaggtgg ctcccgctgaattggaatccatcttgctccaacaccccaacatcttcgacgcaggtgtcgcaggtcttcccgacgat gacgccggtgaacttcccgccgccgttgttgttttggagcacggaaagacgatgacggaaaaagagatcgtggatta cgtcgccagtcaagtaacaaccgcgaaaaagttgcgcggaggagttgtgtttgtggacgaagtaccgaaaggtctta ccggaaaactcgacgcaagaaaaatcagagagatcctcataaaggccaagaagggcggaaagatcgccgtgtaa SEQ ID No. 25, amino acid sequence corresponding to CLUC-398-550
MSGYVNNPEATNALIDKDGWLHSGDIAYWDEDEHFFIVDRLKSLIKYKGYQVAPAELESILLQHPNIFDAGVAGLPD

DDAGELPAAVVVLEHGKTMTEKEIVDYVASQVTTAKKLRGGVVFVDEVPKGLTGKLDARKIREILIKAKKGGKIAV

SEQ ID No. 26, Nucleotide sequence corresponding to CLUC-394-550
cctatgattatgtccggttatgtaaacaatccggaagcgaccaacgccttgattgacaaggatggatggctacattc tggagacatagcttactgggacgaagacgaacacttcttcatcgttgaccgcctgaagtctctgattaagtacaaag gctatcaggtggctcccgctgaattggaatccatcttgctccaacaccccaacatcttcgacgcaggtgtcgcaggt cttcccgacgatgacgccggtgaacttcccgccgccgttgttgttttggagcacggaaagacgatgacggaaaaaga gatcgtggattacgtcgccagtcaagtaacaaccgcgaaaaagttgcgcggaggagttgtgtttgtggacgaagtac cgaaaggtcttaccggaaaactcgacgcaagaaaaatcagagagatcctcataaaggccaagaagggcggaaagatc gccgtgtaa SEQ ID No. 27, amino acid sequence corresponding to CLUC-394-550
GPMIMSGYVNNPEATNALIDKDGWLHSGDIAYWDEDEHFFIVDRLKSLIKYKGYQVAPAELESILLQHPNIFDAGVA

GLPDDDAGELPAAVVVLEHGKTMTEKEIVDYVASQVTTAKKLRGGVVFVDEVPKGLTGKLDARKIREILIKAKKGGK

IAV

SEQ ID No. 28, nucleotide sequence of Coleoptera Lucferase
ATG GTAAAGCGTGAGAAAAATGT CATCTATGGC CCTGAGCCTC TCCATCCTTT

GGAGGATTTGACTGCCGGCG AAATGCTGTT TCGTGCTCTC CGCAAGCACT

CTCATTTGCCTCAAGCCTTG GTCGATGTGG TCGGCGATGA ATCTTTGAGC

TACAAGGAGTTTTTTGAGGC AACCGTCTTG CTGGCTCAGT CCCTCCACAA

TTGTGGCTACAAGATGAACG ACGTCGTTAG TATCTGTGCT GAAAACAATA

CCCGTTTCTTCATTCCAGTC ATCGCCGCAT GGTATATCGG TATGATCGTG

GCTCCAGTCAACGAGAGCTA CATTCCCGAC GAACTGTGTA AAGTCATGGG

TATCTCTAAGCCACAGATTG TCTTCACCAC TAAGAATATT CTGAACAAAG

TCCTGGAAGTCCAAAGCCGC ACCAACTTTA TTAAGCGTAT CATCATCTTG

GACACTGTGGAGAATATTCA CGGTTGCGAA TCTTTGCCTA ATTTCATCTC

TCGCTATTCAGACGGCAACA TCGCAAACTT TAAACCACTC CACTTCGACC

CTGTGGAACAAGTTGCAGCC ATTCTGTGTA GCAGCGGTAC TACTGGACTC

CCAAAGGGAGTCATGCAGAC CCATCAAAAC ATTTGCGTGC GTCTGATCCA

```
TGCTCTCGATCCACGCTACG GCACTCAGCT GATTCCTGGT GTCACCGTCT

TGGTCTACTTGCCTTTCTTC CATGCTTTCG GCTTTCATAT TACTTTGGGT

TACTTTATGGTCGGTCTCCG CGTGATTATG TTCCGCCGTT TTGATCAGGA

GGCTTTCTTGAAAGCCATCC AAGATTATGA AGTCCGCAGT GTCATCAACG

TGCCTAGCGTGATCCTGTTT TTGTCTAAGA GCCCACTCGT GGACAAGTAC

GACTTGTCTTCACTGCGTGA ATTGTGTTGC GGTGCCGCTC CACTGGCTAA

GGAGGTCGCTGAAGTGGCCG CCAAACGCTT GAATCTTCCA GGGATTCGTT

GTGGCTTCGGCCTCACCGAA TCTACCAGTG CGATTATCCA GACTCTCGGG

GATGAGTTTAAGAGCGGCTC TTTGGGCCGT GTCACTCCAC TCATGGCTGC

TAAGATCGCTGATCGCGAAA CTGGTAAGGC TTTGGGCCCG AACCAAGTGG

GCGAGCTGTGTATCAAAGGC CCTATGGTGA GCAAGGGTTA TGTCAATAAC

GTTGAAGCTACCAAGGAGGC CATCGACGAC GACGGCTGGT TGCATTCTGG

TGATTTTGGATATTACGACG AAGATGAGCA TTTTTACGTC GTGGATCGTT

ACAAGGAGCTGATCAAATAC AAGGGTAGCC AGGTTGCTCC AGCTGAGTTG

GAGGAGATTCTGTTGAAAAA TCCATGCATT CGCGATGTCG CTGTGGTCGG

CATTCCTGATCTGGAGGCCG GCGAACTGCC TTCTGCTTTC GTTGTCAAGC

AGCCTGGTACAGAAATTACC GCCAAGAAG TGTATGATTA CCTGGCTGAA

CGTGTGAGCCATACTAAGTA CTTGCGTGGC GGCGTGCGTT TTGTTGACTC

CATCCCTCGTAACGTAACAG GCAAAATTAC CCGCAAGGAG CTGTTGAAAC

AATTGTTGGTGAAGGCCGGC GGTTAG

SEQ ID No. 29, amino acid sequence of Coleoptera Lucferase
MVKREKNVIYGPEPLHPLEDLTAGEMLFRALRKHSHLPQALVDVVGDESLSYKEFFEATVLLAQSLHNCGYKMNDVV

SICAENNTRFFIPVIAAWYIGMIVAPVNESYIPDELCKVMGISKPQIVFTTKNILNKVLEVQSRTNFIKRIIILDTV

ENIHGCESLPNFISRYSDGNIANFKPLHFDPVEQVAAILCSSGTTGLPKGVMQTHQNICVRLIHALDPRYGTQLIPG

VTVLVYLPFFHAFGFHITLGYFMVGLRVIMFRRFDQEAFLKAIQDYEVRSVINVPSVILFLSKSPLVDKYDLSSLRE

LCCGAAPLAKEVAEVAAKRLNLPGIRCGFGLTESTSAIIQTLGDEFKSGSLGRVTPLMAAKIADRETGKALGPNQVG

ELCIKGPMVSKGYVNNVEATKEAIDDDGWLHSGDFGYYDEDEHFYVVDRYKELIKYKGSQVAPAELEEILLKNPCIR

DVAVVGIPDLEAGELPSAFVVKQPGTEITAKEVYDYLAERVSHTKYLRGGVRFVDSIPRNVTGKITRKELLKQLLVK

AGG

SEQ ID No. 30, nucleotide sequence of Goussia Luciferase
atgggagtgaa agttctttt gcccttattt gtattgctgt ggccgaggcc aaaccaactg aaaacaatga agatttcaac attgtagctg tagctagcaa ctttgctaca acggatctcg atgctgaccg tggtaaattg cccggaaaaa aattaccact tgaggtactc aaagaaatgg aagccaatgc taggaaagct ggctgcacta ggggatgtct gatatgcctg tcacacatca agtgtacacc caaatgaag aagtttatcc caggaagatg ccacacctat gaaggagaca agaaagtgc acagggagga ataggagagg ctattgttga cattcctgaa attcctgggt ttaaggattt ggaacccatg gaacaattca ttgcacaagt tgacctatgt gtagactgca caactggatg cctcaaaggt cttgccaatg tgcaatgttc tgatttactc aagaaatggc tgccacaaag atgtgcaact tttgctagca aaattcaagg ccaagtggac aaaataaagg gtgccggtgg tgattaa SEQ ID No. 31, amino acid sequence of Goussia Luciferase
MGVKVLFALICIAVAEAKPTENNEDFNIVAVASNFATTDLDADRGKLPGKKLPLEVLKEMEANARKAGCTRGCLICL

SHIKCTPKMKKFIPGRCHTYEGDKESAQGGIGEAIVDIPEIPGFKDLEPMEQFIAQVDLCVDCTTGCLKGLANVQCS

DLLKKWLPQRCATFASKIQGQVDKIKGAGGD
```

-continued

SEQ ID No. 32, nucleotide sequence of Aqueorin Photoprotein luciferase
ATG CTT ACA TCA GAC TTC GAC AAC CCA AGA TGG ATT GGA CGA CAC AAG CAT ATG TTC

AAT TTC CTT GAT GTC AAC CAC AAT GGA AAA ATC TCT CTT GAC GAG ATG GTC TAC AAG

GCA TCT GAT ATT GTC ATC AAT AAC CTT GGA GCA ACA CCT GAG CAA GCC AAA CGA CAC

AAA GAT GCT GTA GAA GCC TTC TTC GGA GGA GCT GGA ATG AAA TAT GGT GTG GAA ACT

GAT TGG CCT GCA TAT ATT GAA GGA TGG AAA AAA TTG GCT ACT GAT GAA TTG GAG AAA

TAC GCC AAA AAC GAA CCA ACG CTC ATC CGT ATA TGG GGT GAT GCT TTG TTT GAT ATC

GTT GAC AAA GAT CAA AAT GGA GCC ATT ACA CTG GAT GAA TGG AAA GCA TAC ACC AAA

GCT GCT GGT ATC ATC CAA TCA TCA GAA GAT TGC GAG GAA ACA TTC AGA GTG TGC GAT

ATT GAT GAA AGT GGA CAA CTC GAT GTT GAT GAG ATG ACA AGA CAA CAT TTA GGA TTT

TGG TAC ACC ATG GAT CCT GCT TGC GAA AAG CTC TAC GGT GGA GCT GTC CCC TAA

SEQ ID No. 33, amino acid sequence of Aqueorin Photoprotein luciferase
MLTSDFDNPRWIGRHKHMFNFLDVNHNGKISLDEMVYKASDIVINNLGATPEQAKRHKDAVEAFFGGAGMKYGVETD

WPAYIEGWKKLATDELEKYAKNEPTLIRIWGDALFDIVDKDQNGAITLDEWKAYTKAAGIIQSSEDCEETFRVCDID

ESGQLDVDEMTRQHLGFWYTMDPACEKLYGGAVP

SEQ ID No. 34, nucleotide sequence of Bacterial luciferase
atgaataa atggaattac ggagtcttct tcgttaactt ttataataaa ggccaacaag agccatcaaa acgatgaat aatgcattag aaacattacg tattattgat gaagatacat ctatttatga tgtgattaat attgatgacc actatcttgt aaagaaagac agtgaagata aaaagctagc gtcttttatt acactaggag aaaaactata tgtgcttgct accagtgaaa acacagttga tattgcagcg aaatatgcat taccgttagt tttcaaatgg gatgatataa atgaggaacg acttaaattg ttgagttttt ataatgcatc cgcaagtaaa tataacaaga atatagattt ggttcgacac cagcttatgt tacatgtcaa tgttaatgag gcagaaactg tagcaaaaga agaactcaaa ttatatattg aaaactatgt agcatgtaca cagcctagta attttaatgg ctcgattgat agtattattc agagtaacgt gacagggagt tataaagact gttttgtcata tgtagcgaat cttgctggta aatttgataa tactgtggac ttcttacttt gttttgagtc aatgcaagat caaaataaga aaaaatcagt aatgatagat cttaataatc aagttattaa gttccgccaa gataataatc taa SEQ ID No. 35, amino acid sequence of Bacterial luciferase
MNKWNYGVFFVNFYNKGQQEPSKTMNNALETLRIIDEDTSIYDVINIDDHYLVKKDSEDKKLASFITLGEKLYVLAT

SENTVDIAAKYALPLVFKWDDINEERLKLLSFYNASASKYNKNIDLVRHQLMLHVNVNEAETVAKEELKLYIENYVA

CTQPSNFNGSIDSIIQSNVTGSYKDCLSYVANLAGKFDNTVDFLLCFESMQDQNKKKSVMIDLNNQVIKFRQDNNLX

SEQ ID No. 36, nucleotide sequence of NRLUC (N-fragment of Renilla
Luciferase)
ATG GCT TCC AAG GTG TAC GAC CCC GAG CAA CGC AAA CGC ATG ATC ACT GGG CCT CAG

TGG TGG GCT CGC TGC AAG CAA ATG AAC GTG CTG GAC TCC TTC ATC AAC TAC TAT GAT

TCC GAG AAG CAC GCC GAG AAC GCC GTG ATT TTT CTG CAT GGT AAC GCT GCC TCC AGC

TAC CTG TGG AGG CAC GTC GTG CCT CAC ATC GAG CCC GTG GCT AGA TGC ATC ATC CCT

GAT CTG ATC GGA ATG GGT AAG TCC GGC AAG AGC GGG AAT GGC TCA TAT CGC CTC CTG

GAT CAC TAC AAG TAC CTC ACC GCT TGG TTC GAG CTG CTG AAC CTT CCA AAG AAA ATC

ATC TTT GTG GGC CAC GAC TGG GGG GCT TGT CTG GCC TTT CAC TAC TCC TAC GAG CAC

CAA GAC AAG ATC AAG GCC ATC GTC CAT GCT GAG AGT GTC GTG GAC GTG ATC GAG TCC

TGG GAC GAG TGG CCT GAC ATC GAG GAG GAT ATC GCC CTG ATC AAG AGC GAA GAG GGC

GAG AAA ATG GTG CTT GAG AAT AAC TTC TTC GTC GAG ACC ATG CTC CCA AGC AAG ATC

```
ATG CGG AAA CTG GAG CCT GAG GAG TTC GCT GCC TAC CTG GAG CCA TTC AAG GAG AAG

GGC GAG GTT AGA CGG CCT ACC CTC TCC TGG CCT CGC GAG ATC CCT CTC GTT AAG GGA

GGC
```

SEQ ID No. 37, amino acid sequence of NRLUC (N-fragment of Renilla Luciferase)
ASMASKVYDPEQRKRMITGPQWWARCKQMNVLDSFINYYDSEKHAENAVIFLHGNAASSYLWRHVVPHIEPVARCII

PDLIGMGKSGKSGNGSYRLLDHYKYLTAWFELLNLPKKIIFVGHDWGACLAFHYSYEHQDKIKAIVHAESVVDVIES

WDEWPDIEEDIALIKSEEGEKMVLENNFFVETMLPSKIMRKLEPEEFAAYLEPFKEKGEVRRPTLSWPREIPLVK

SEQ ID No. 38, nucleotide sequence of CRLUC (C-fragment of Renilla Luciferase)
AAGCCCGACGTCGTCCAGATTGTCCGCAACTACAACGCCTACCTTCGGGCCAGCGACGATCTGCCTAAGATGTTCAT

CGAGTCCGACCCTGGGTTCTTTTCCAACGCTATTGTCGAGGGAGCTAAGAAGTTCCCTAACACCGAGTTCGTGAAGG

TGAAGGGCCTCCACTTCAGCCAGGAGGACGCTCCAGATGAAATGGGTAAGTACATCAAGAGCTTCGTGGAGCGCGTG

CTGAAGAACGAGCAGTAA

SEQ ID No. 39, amino acid sequence of CRLUC (C-fragment of Renilla Luciferase)
KPDVVQIVRNYNAYLRASDDLPKMFIESDPGFFSNAIVEGAKKFPNTEFVKVKGLHFSQEDAPDEMGKYIKSFVERV

LKNEQ

SEQ ID No. 40, Human Estrogen receptor beta
MEDAKNIKKGPAPFYPLEDGTAGEQLHKAMKRYALVPGTIAFTDAHIEVDITYAEYFEMSVRLAEAMKRYGLNTNHR

IVVCSENSLQFFMPVLGALFIGVAVAPANDIYNERELLNSMGISQPTVVFVSKKGLQKILNVQKKLPIIQKIIIMDS

KTDYQGFQSMYTFVTSHLPPGFNEYDFVPESFDRDKTIALIMNSSGSTGLPKGVALPHRTACVRFSHARDPIFGNQI

IPDTAILSVVPFHHGFGMFTTLGYLICGFRVVLMYRFEEELFLRSLQDYKIQSALLVPTLFSFFAKSTLIDKYDLSN

LHEIASGGAPLSKEVGEAVAKRFHLPGIRQGYGLTETTSAILITPEGDDKPGAVGKVVPFFEAKVVDLDTGKTLGVN

QRGELCVRGPMIMSGYVNNPEATNALIDKDGWLHSGDIAYWDEDEHFFIVDRLKSLIKYKGYQVAPAELESILLQHP

NIFDAGVAGLPDDDAGELPAAVVVLEHGKTMTEKEIVDYVASQVTTAKKLRGGVVFVDEVPKGLTGKLDARKIREIL

IKAKKGGKIAV

---

We claim the following:

1. An estrogen receptor (ER) intramolecular folding system, comprising: a first split protein fragment, an ER ligand binding domain, and a second split protein fragment;

wherein the first split protein fragment is attached to a first portion of the ER ligand binding domain, wherein the ER ligand binding domain has amino acid sequence comprising SEQ ID NO: 12, and wherein the second split protein fragment is attached to a second portion of the ER ligand binding domain; and wherein the first split protein fragment and the second split protein fragment are not bioluminescent, and wherein the first split protein fragment and the second split protein fragment are adapted to substantially complement to form a bioluminescent protein.

2. The ER intramolecular folding system of claim 1, wherein the ER ligand binding domain is adapted to change from a first conformational position to a second conformational position upon interaction with an ER ligand, wherein in the first conformational position, the first split protein fragment and the second protein fragment are proximally separated so that the first split protein fragment and the second protein fragment do not substantially complement, and wherein in the second conformational position, the first split protein fragment and the second protein fragment are proximally closer so that the first split protein fragment and the second protein fragment are able to substantially complement.

3. The ER intramolecular folding system of claim 1, wherein the ER ligand binding domain is adapted to change from a first conformational position to a second conformational position upon interaction with an ER agonist, wherein the ER ligand binding domain is adapted to change from a first conformational position to a third conformational position upon interaction with an ER antagonist;

wherein in the first conformational position the first split protein fragment and the second protein fragment are proximally separated so that the first split protein fragment and the second protein fragment do not substantially complement, wherein in the second conformational position the first split protein fragment and the second protein fragment are proximally separated after binding with ligand agonist so that the first split protein fragment and the second protein fragment are able to partially complement, wherein in the third conformational position the first split protein fragment and the second protein fragment are proximally separated after binding with ligand antagonist so that the first split protein fragment and the second protein fragment are able to substantially complement; and wherein when the first split protein fragment and the second protein fragment partially complement in the presence of a bioluminescence initiating compound, a first amount of bioluminescent energy is produced; wherein when the first split protein fragment and the second protein fragment substantially complement in the presence of a bioluminescence initiating compound, a second amount of bioluminescent energy is produced; and wherein the first amount of bioluminescent energy and the second amount of bioluminescent energy are distinguishable.

4. A fusion protein, comprising:
a first split protein fragment, an ER ligand binding domain, and a second split protein fragment; wherein the first split protein fragment is attached to a first portion of the ER ligand binding domain, and wherein the second split protein fragment is attached to a second portion of the ER ligand binding domain; wherein the ER ligand binding domain has amino acid sequence comprising SEQ ID NO: 12; wherein the first split protein fragment and the second split protein fragment are not bioluminescent; and wherein the first split protein fragment and the second split protein fragment are adapted to substantially complement to form a bioluminescent protein.

5. The ER intramolecular folding system of claim 1, wherein the first split protein has an amino acid sequence comprising SEQ ID NO: 37.

6. The ER intramolecular folding system of claim 1, wherein the second split protein has an amino acid sequence comprising SEQ ID NO: 39.

7. The ER intramolecular folding system of claim 6, wherein the first split protein has an amino acid sequence comprising SEQ ID NO: 37.

8. The fusion protein of claim 4, wherein the first split protein has an amino acid sequence SEQ ID NO: 37.

9. The fusion protein of claim 4, wherein the second split protein has an amino acid sequence comprising SEQ ID NO: 39.

10. The fusion protein of claim 9, wherein the first split protein has an amino acid sequence comprising SEQ ID NO: 37.

11. An estrogen receptor (ER) intramolecular folding system, comprising: a first split protein fragment, an ER ligand binding domain, and a second split protein fragment;

wherein the first split protein fragment is attached to a first portion of the ER ligand binding domain, wherein the first split protein fragment has amino acid sequence comprising SEQ ID NO: 37, and wherein the second split protein fragment is attached to a second portion of the ER ligand binding domain; and wherein the first split protein fragment and the second split protein fragment are not bioluminescent, and wherein the first split protein fragment and the second split protein fragment are adapted to substantially complement to form a bioluminescent protein.

12. The ER intramolecular folding system of claim 11, wherein the ER ligand binding domain is adapted to change from a first conformational position to a second conformational position upon interaction with an ER ligand, wherein in the first conformational position, the first split protein fragment and the second protein fragment are proximally separated so that the first split protein fragment and the second protein fragment do not substantially complement, and wherein in the second conformational position, the first split protein fragment and the second protein fragment are proximally closer so that the first split protein fragment and the second protein fragment are able to substantially complement.

13. The ER intramolecular folding system of claim 11, wherein the ER ligand binding domain is adapted to change from a first conformational position to a second conformational position upon interaction with an ER agonist, wherein the ER ligand binding domain is adapted to change from a first conformational position to a third conformational position upon interaction with an ER antagonist;

wherein in the first conformational position the first split protein fragment and the second protein fragment are proximally separated so that the first split protein fragment and the second protein fragment do not substantially complement, wherein in the second conformational position the first split protein fragment and the second protein fragment are proximally separated after binding with ligand agonist so that the first split protein fragment and the second protein fragment are able to partially complement, wherein in the third conformational position the first split protein fragment and the second protein fragment are proximally separated after binding with ligand antagonist so that the first split protein fragment and the second protein fragment are able to substantially complement; and wherein when the first split protein fragment and the second protein fragment partially complement in the presence of a bioluminescence initiating compound, a first amount of bioluminescent energy is produced; wherein when the first split protein fragment and the second protein fragment substantially complement in the presence of a bioluminescence initiating compound, a second amount of bioluminescent energy is produced; and wherein the first amount of bioluminescent energy and the second amount of bioluminescent energy are distinguishable.

14. The ER intramolecular folding system of claim 11, wherein the second split protein has an amino acid sequence comprising SEQ ID NO: 39.

15. A fusion protein, comprising:
a first split protein fragment, an ER ligand binding domain, and a second split protein fragment; wherein the first split protein fragment is attached to a first portion of the ER ligand binding domain, and wherein the second split protein fragment is attached to a second portion of the ER ligand binding domain; wherein the first split protein fragment has amino acid sequence comprising SEQ ID NO: 37; wherein the first split protein fragment and the second split protein fragment are not bioluminescent; and wherein the first split protein fragment and the second split protein fragment are adapted to substantially complement to form a bioluminescent protein.

16. The fusion protein of claim 15, wherein the second split protein has an amino acid sequence comprising SEQ ID NO: 39.

17. An estrogen receptor (ER) intramolecular folding system, comprising: a first split protein fragment, an ER ligand binding domain, and a second split protein fragment;
wherein the first split protein fragment is attached to a first portion of the ER ligand binding domain, wherein the second split protein has an amino acid sequence comprising SEQ ID NO: 39, and wherein the second split protein fragment is attached to a second portion of the ER ligand binding domain; and
wherein the first split protein fragment and the second split protein fragment are not bioluminescent, and wherein the first split protein fragment and the second split protein fragment are adapted to substantially complement to form a bioluminescent protein.

18. The ER intramolecular folding system of claim 17, wherein the ER ligand binding domain is adapted to change from a first conformational position to a second conformational position upon interaction with an ER ligand, wherein in the first conformational position, the first split protein fragment and the second protein fragment are proximally separated so that the first split protein fragment and the second protein fragment do not substantially complement, and wherein in the second conformational position, the first split protein fragment and the second protein fragment are proximally closer so that the first split protein fragment and the second protein fragment are able to substantially complement.

19. The ER intramolecular folding system of claim 17, wherein the ER ligand binding domain is adapted to change from a first conformational position to a second conformational position upon interaction with an ER agonist, wherein the ER ligand binding domain is adapted to change from a first conformational position to a third conformational position upon interaction with an ER antagonist;
wherein in the first conformational position the first split protein fragment and the second protein fragment are proximally separated so that the first split protein fragment and the second protein fragment do not substantially complement, wherein in the second conformational position the first split protein fragment and the second protein fragment are proximally separated after binding with ligand agonist so that the first split protein fragment and the second protein fragment are able to partially complement, wherein in the third conformational position the first split protein fragment and the second protein fragment are proximally separated after binding with ligand antagonist so that the first split protein fragment and the second protein fragment are able to substantially complement; and
wherein when the first split protein fragment and the second protein fragment partially complement in the presence of a bioluminescence initiating compound, a first amount of bioluminescent energy is produced; wherein when the first split protein fragment and the second protein fragment substantially complement in the presence of a bioluminescence initiating compound, a second amount of bioluminescent energy is produced; and wherein the first amount of bioluminescent energy and the second amount of bioluminescent energy are distinguishable.

20. A fusion protein, comprising:
a first split protein fragment, an ER ligand binding domain, and a second split protein fragment; wherein the first split protein fragment is attached to a first portion of the ER ligand binding domain, and wherein the second split protein fragment is attached to a second portion of the ER ligand binding domain; wherein the second split protein has an amino acid sequence comprising SEQ ID NO: 39; wherein the first split protein fragment and the second split protein fragment are not bioluminescent; and wherein the first split protein fragment and the second split protein fragment are adapted to substantially complement to form a bioluminescent protein.

* * * * *

SEQUENCE LISTING

<160> NUMBER OF SEQ ID NOS: 40

<210> SEQ ID NO 1
<211> LENGTH: 269
<212> TYPE: PRT
<213> ORGANISM: Homo sapiens

<400> SEQUENCE: 1

```
Gly Ser Ala Gly Asp Met Arg Ala Ala Asn Leu Trp Pro Ser Pro Leu
1               5                   10                  15

Met Ile Lys Arg Ser Lys Lys Asn Ser Leu Ala Leu Ser Leu Thr Ala
            20                  25                  30

Asp Gln Met Val Ser Ala Leu Leu Asp Ala Glu Pro Pro Ile Leu Tyr
        35                  40                  45

Ser Glu Tyr Asp Pro Thr Arg Pro Phe Ser Glu Ala Ser Met Met Gly
    50                  55                  60

Leu Leu Thr Asn Leu Ala Asp Arg Glu Leu Val His Met Ile Asn Trp
65                  70                  75                  80

Ala Lys Arg Val Pro Gly Phe Val Asp Leu Thr Leu His Asp Gln Val
                85                  90                  95
```

-continued

His Leu Leu Glu Cys Ala Trp Leu Glu Ile Leu Met Ile Gly Leu Val
            100                 105                 110

Trp Arg Ser Met Glu His Pro Val Lys Leu Leu Phe Ala Pro Asn Leu
            115                 120                 125

Leu Leu Asp Arg Asn Gln Gly Lys Cys Val Glu Gly Met Val Glu Ile
        130                 135                 140

Phe Asp Met Leu Leu Ala Thr Ser Ser Arg Phe Arg Met Met Asn Leu
145                 150                 155                 160

Gln Gly Glu Glu Phe Val Cys Leu Lys Ser Ile Ile Leu Leu Asn Ser
                165                 170                 175

Gly Val Tyr Thr Phe Leu Ser Ser Thr Leu Lys Ser Leu Glu Glu Lys
            180                 185                 190

Asp His Ile His Arg Val Leu Asp Lys Ile Thr Asp Thr Leu Ile His
        195                 200                 205

Leu Met Ala Lys Ala Gly Leu Thr Leu Gln Gln Gln His Gln Arg Leu
    210                 215                 220

Ala Gln Leu Leu Leu Ile Leu Ser His Ile Arg His Met Ser Asn Lys
225                 230                 235                 240

Gly Met Glu His Leu Tyr Ser Met Lys Cys Lys Asn Val Val Pro Leu
                245                 250                 255

Tyr Asp Leu Leu Leu Glu Met Leu Asp Ala His Arg Leu
                260                 265

<210> SEQ ID NO 2
<211> LENGTH: 315
<212> TYPE: PRT
<213> ORGANISM: Homo sapiens

<400> SEQUENCE: 2

Gly Ser Ala Gly Asp Met Arg Ala Ala Asn Leu Trp Pro Ser Pro Leu
1               5                   10                  15

Met Ile Lys Arg Ser Lys Lys Asn Ser Leu Ala Leu Ser Leu Thr Ala
            20                  25                  30

Asp Gln Met Val Ser Ala Leu Leu Asp Ala Glu Pro Pro Ile Leu Tyr
        35                  40                  45

Ser Glu Tyr Asp Pro Thr Arg Pro Phe Ser Glu Ala Ser Met Met Gly
50                  55                  60

Leu Leu Thr Asn Leu Ala Asp Arg Glu Leu Val His Met Ile Asn Trp
65                  70                  75                  80

Ala Lys Arg Val Pro Gly Phe Val Asp Leu Thr Leu His Asp Gln Val
                85                  90                  95

His Leu Leu Glu Cys Ala Trp Leu Glu Ile Leu Met Ile Gly Leu Val
            100                 105                 110

Trp Arg Ser Met Glu His Pro Val Lys Leu Leu Phe Ala Pro Asn Leu
            115                 120                 125

Leu Leu Asp Arg Asn Gln Gly Lys Cys Val Glu Gly Met Val Glu Ile
        130                 135                 140

Phe Asp Met Leu Leu Ala Thr Ser Ser Arg Phe Arg Met Met Asn Leu
145                 150                 155                 160

Gln Gly Glu Glu Phe Val Cys Leu Lys Ser Ile Ile Leu Leu Asn Ser
                165                 170                 175

Gly Val Tyr Thr Phe Leu Ser Ser Thr Leu Lys Ser Leu Glu Glu Lys
            180                 185                 190

Asp His Ile His Arg Val Leu Asp Lys Ile Thr Asp Thr Leu Ile His
        195                 200                 205

```
Leu Met Ala Lys Ala Gly Leu Thr Leu Gln Gln Gln His Gln Arg Leu
    210                 215                 220

Ala Gln Leu Leu Leu Ile Leu Ser His Ile Arg His Met Ser Asn Lys
225                 230                 235                 240

Gly Met Glu His Leu Tyr Ser Met Lys Cys Lys Asn Val Val Pro Leu
                245                 250                 255

Tyr Asp Leu Leu Leu Glu Met Leu Asp Ala His Arg Leu His Ala Pro
                260                 265                 270

Thr Ser Arg Gly Gly Ala Ser Val Glu Glu Thr Asp Gln Ser His Leu
            275                 280                 285

Ala Thr Ala Gly Ser Thr Ser Ser His Ser Leu Gln Lys Tyr Tyr Ile
    290                 295                 300

Thr Gly Glu Ala Glu Gly Phe Pro Ala Thr Val
305                 310                 315

<210> SEQ ID NO 3
<211> LENGTH: 595
<212> TYPE: PRT
<213> ORGANISM: Homo sapiens

<400> SEQUENCE: 3

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270
```

```
Asp Gly Glu Gly Arg Gly Glu Val Gly Ser Ala Gly Asp Met Arg Ala
            275                 280                 285
Ala Asn Leu Trp Pro Ser Pro Leu Met Ile Lys Arg Ser Lys Lys Asn
        290                 295                 300
Ser Leu Ala Leu Ser Leu Thr Ala Asp Gln Met Val Ser Ala Leu Leu
305                 310                 315                 320
Asp Ala Glu Pro Pro Ile Leu Tyr Ser Glu Tyr Asp Pro Thr Arg Pro
                325                 330                 335
Phe Ser Glu Ala Ser Met Met Gly Leu Leu Thr Asn Leu Ala Asp Arg
            340                 345                 350
Glu Leu Val His Met Ile Asn Trp Ala Lys Arg Val Pro Gly Phe Val
            355                 360                 365
Asp Leu Thr Leu His Asp Gln Val His Leu Leu Glu Cys Ala Trp Leu
        370                 375                 380
Glu Ile Leu Met Ile Gly Leu Val Trp Arg Ser Met Glu His Pro Val
385                 390                 395                 400
Lys Leu Leu Phe Ala Pro Asn Leu Leu Leu Asp Arg Asn Gln Gly Lys
                405                 410                 415
Cys Val Glu Gly Met Val Glu Ile Phe Asp Met Leu Leu Ala Thr Ser
            420                 425                 430
Ser Arg Phe Arg Met Met Asn Leu Gln Gly Glu Glu Phe Val Cys Leu
            435                 440                 445
Lys Ser Ile Ile Leu Leu Asn Ser Gly Val Tyr Thr Phe Leu Ser Ser
        450                 455                 460
Thr Leu Lys Ser Leu Glu Glu Lys Asp His Ile His Arg Val Leu Asp
465                 470                 475                 480
Lys Ile Thr Asp Thr Leu Ile His Leu Met Ala Lys Ala Gly Leu Thr
                485                 490                 495
Leu Gln Gln Gln His Gln Arg Leu Ala Gln Leu Leu Leu Ile Leu Ser
            500                 505                 510
His Ile Arg His Met Ser Asn Lys Gly Met Glu His Leu Tyr Ser Met
        515                 520                 525
Lys Cys Lys Asn Val Val Pro Leu Tyr Asp Leu Leu Leu Glu Met Leu
530                 535                 540
Asp Ala His Arg Leu His Ala Pro Thr Ser Arg Gly Gly Ala Ser Val
545                 550                 555                 560
Glu Glu Thr Asp Gln Ser His Leu Ala Thr Ala Gly Ser Thr Ser Ser
                565                 570                 575
His Ser Leu Gln Lys Tyr Tyr Ile Thr Gly Glu Ala Glu Gly Phe Pro
            580                 585                 590
Ala Thr Val
        595

<210> SEQ ID NO 4
<211> LENGTH: 269
<212> TYPE: PRT
<213> ORGANISM: Mus musculus

<400> SEQUENCE: 4

Arg Asn Glu Met Gly Ala Ser Gly Asp Met Arg Ala Ala Asn Leu Trp
1               5                   10                  15
Pro Ser Pro Leu Val Ile Lys His Thr Lys Lys Asn Ser Pro Ala Leu
            20                  25                  30
Ser Leu Thr Ala Asp Gln Met Val Ser Ala Leu Leu Asp Ala Glu Pro
        35                  40                  45
```

```
Pro Met Ile Tyr Ser Glu Tyr Asp Pro Ser Arg Pro Phe Ser Glu Ala
        50                  55                  60

Ser Met Met Gly Leu Leu Thr Asn Leu Ala Asp Arg Glu Leu Val His
65                  70                  75                  80

Met Ile Asn Trp Ala Lys Arg Val Pro Gly Phe Gly Asp Leu Asn Leu
                    85                  90                  95

His Asp Gln Val His Leu Leu Glu Cys Ala Trp Leu Glu Ile Leu Met
                100                 105                 110

Ile Gly Leu Val Trp Arg Ser Met Glu His Pro Gly Lys Leu Leu Phe
            115                 120                 125

Ala Pro Asn Leu Leu Asp Arg Asn Gln Gly Lys Cys Val Glu Gly
        130                 135                 140

Met Val Glu Ile Phe Asp Met Leu Leu Ala Thr Ser Ser Arg Phe Arg
145                 150                 155                 160

Met Met Asn Leu Gln Gly Glu Glu Phe Val Cys Leu Lys Ser Ile Ile
                165                 170                 175

Leu Leu Asn Ser Gly Val Tyr Thr Phe Leu Ser Ser Thr Leu Lys Ser
            180                 185                 190

Leu Glu Glu Lys Asp His Ile His Arg Val Leu Asp Lys Ile Thr Asp
        195                 200                 205

Thr Leu Ile His Leu Met Ala Lys Ala Gly Leu Thr Leu Gln Gln Gln
210                 215                 220

His Arg Arg Leu Ala Gln Leu Leu Leu Ile Leu Ser His Ile Arg His
225                 230                 235                 240

Met Ser Asn Lys Gly Met Glu His Leu Tyr Asn Met Lys Cys Lys Asn
                245                 250                 255

Val Val Pro Leu Tyr Asp Leu Leu Leu Glu Met Leu Asp
            260                 265

<210> SEQ ID NO 5
<211> LENGTH: 319
<212> TYPE: PRT
<213> ORGANISM: Mus musculus

<400> SEQUENCE: 5

Arg Asn Glu Met Gly Ala Ser Gly Asp Met Arg Ala Ala Asn Leu Trp
1               5                   10                  15

Pro Ser Pro Leu Val Ile Lys His Thr Lys Lys Asn Ser Pro Ala Leu
                20                  25                  30

Ser Leu Thr Ala Asp Gln Met Val Ser Ala Leu Leu Asp Ala Glu Pro
            35                  40                  45

Pro Met Ile Tyr Ser Glu Tyr Asp Pro Ser Arg Pro Phe Ser Glu Ala
        50                  55                  60

Ser Met Met Gly Leu Leu Thr Asn Leu Ala Asp Arg Glu Leu Val His
65                  70                  75                  80

Met Ile Asn Trp Ala Lys Arg Val Pro Gly Phe Gly Asp Leu Asn Leu
                    85                  90                  95

His Asp Gln Val His Leu Leu Glu Cys Ala Trp Leu Glu Ile Leu Met
                100                 105                 110

Ile Gly Leu Val Trp Arg Ser Met Glu His Pro Gly Lys Leu Leu Phe
            115                 120                 125

Ala Pro Asn Leu Leu Asp Arg Asn Gln Gly Lys Cys Val Glu Gly
        130                 135                 140

Met Val Glu Ile Phe Asp Met Leu Leu Ala Thr Ser Ser Arg Phe Arg
145                 150                 155                 160
```

```
Met Met Asn Leu Gln Gly Glu Glu Phe Val Cys Leu Lys Ser Ile Ile
            165                 170                 175

Leu Leu Asn Ser Gly Val Tyr Thr Phe Leu Ser Ser Thr Leu Lys Ser
        180                 185                 190

Leu Glu Glu Lys Asp His Ile His Arg Val Leu Asp Lys Ile Thr Asp
    195                 200                 205

Thr Leu Ile His Leu Met Ala Lys Ala Gly Leu Thr Leu Gln Gln Gln
210                 215                 220

His Arg Arg Leu Ala Gln Leu Leu Ile Leu Ser His Ile Arg His
225                 230                 235                 240

Met Ser Asn Lys Gly Met Glu His Leu Tyr Asn Met Lys Cys Lys Asn
                245                 250                 255

Val Val Pro Leu Tyr Asp Leu Leu Leu Glu Met Leu Asp Ala His Arg
            260                 265                 270

Leu His Ala Pro Ala Ser Arg Met Gly Val Pro Pro Glu Glu Pro Ser
        275                 280                 285

Gln Thr Gln Leu Ala Thr Thr Ser Ser Thr Ser Ala His Ser Leu Gln
    290                 295                 300

Thr Tyr Tyr Ile Pro Pro Glu Ala Glu Gly Phe Pro Asn Thr Ile
305                 310                 315

<210> SEQ ID NO 6
<211> LENGTH: 599
<212> TYPE: PRT
<213> ORGANISM: Mus musculus

<400> SEQUENCE: 6

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Met Pro Met Glu Arg Ala Leu Gly Glu Val Tyr Val Asp Asn Ser Lys
        35                  40                  45

Pro Thr Val Phe Asn Tyr Pro Glu Gly Ala Ala Tyr Glu Phe Asn Ala
    50                  55                  60

Ala Ala Ala Ala Ala Ala Ala Ser Ala Pro Val Tyr Gly Gln Ser
65                  70                  75                  80

Gly Ile Ala Tyr Gly Pro Gly Ser Glu Ala Ala Ala Phe Ser Ala Asn
                85                  90                  95

Ser Leu Gly Ala Phe Pro Gln Leu Asn Ser Val Ser Pro Ser Pro Leu
            100                 105                 110

Met Leu Leu His Pro Pro Pro Gln Leu Ser Pro Phe Leu His Pro His
        115                 120                 125

Gly Gln Gln Val Pro Tyr Tyr Leu Glu Asn Glu Pro Ser Ala Tyr Ala
    130                 135                 140

Val Arg Asp Thr Gly Pro Pro Ala Phe Tyr Arg Ser Asn Ser Asp Asn
145                 150                 155                 160

Arg Arg Gln Asn Gly Arg Glu Arg Leu Ser Ser Ser Asn Glu Lys Gly
                165                 170                 175

Asn Met Ile Met Glu Ser Ala Lys Glu Thr Arg Tyr Cys Ala Val Cys
            180                 185                 190

Asn Asp Tyr Ala Ser Gly Tyr His Tyr Gly Val Trp Ser Cys Glu Gly
        195                 200                 205

Cys Lys Ala Phe Phe Lys Arg Ser Ile Gln Gly His Asn Asp Tyr Met
    210                 215                 220
```

Cys Pro Ala Thr Asn Gln Cys Thr Ile Asp Lys Asn Arg Arg Lys Ser
225                 230                 235                 240

Cys Gln Ala Cys Arg Leu Arg Lys Cys Tyr Glu Val Gly Met Met Lys
            245                 250                 255

Gly Gly Ile Arg Lys Asp Arg Arg Gly Gly Arg Met Leu Lys His Lys
        260                 265                 270

Arg Gln Arg Asp Asp Leu Glu Gly Arg Asn Glu Met Gly Ala Ser Gly
    275                 280                 285

Asp Met Arg Ala Ala Asn Leu Trp Pro Ser Pro Leu Val Ile Lys His
290                 295                 300

Thr Lys Lys Asn Ser Pro Ala Leu Ser Leu Thr Ala Asp Gln Met Val
305                 310                 315                 320

Ser Ala Leu Leu Asp Ala Glu Pro Pro Met Ile Tyr Ser Glu Tyr Asp
            325                 330                 335

Pro Ser Arg Pro Phe Ser Glu Ala Ser Met Met Gly Leu Leu Thr Asn
        340                 345                 350

Leu Ala Asp Arg Glu Leu Val His Met Ile Asn Trp Ala Lys Arg Val
    355                 360                 365

Pro Gly Phe Gly Asp Leu Asn Leu His Asp Gln Val His Leu Leu Glu
370                 375                 380

Cys Ala Trp Leu Glu Ile Leu Met Ile Gly Leu Val Trp Arg Ser Met
385                 390                 395                 400

Glu His Pro Gly Lys Leu Leu Phe Ala Pro Asn Leu Leu Asp Arg
            405                 410                 415

Asn Gln Gly Lys Cys Val Glu Gly Met Val Glu Ile Phe Asp Met Leu
        420                 425                 430

Leu Ala Thr Ser Ser Arg Phe Arg Met Met Asn Leu Gln Gly Glu Glu
    435                 440                 445

Phe Val Cys Leu Lys Ser Ile Ile Leu Leu Asn Ser Gly Val Tyr Thr
450                 455                 460

Phe Leu Ser Ser Thr Leu Lys Ser Leu Glu Glu Lys Asp His Ile His
465                 470                 475                 480

Arg Val Leu Asp Lys Ile Thr Asp Thr Leu Ile His Leu Met Ala Lys
            485                 490                 495

Ala Gly Leu Thr Leu Gln Gln Gln His Arg Arg Leu Ala Gln Leu Leu
        500                 505                 510

Leu Ile Leu Ser His Ile Arg His Met Ser Asn Lys Gly Met Glu His
    515                 520                 525

Leu Tyr Asn Met Lys Cys Lys Asn Val Val Pro Leu Tyr Asp Leu Leu
530                 535                 540

Leu Glu Met Leu Asp Ala His Arg Leu His Ala Pro Ala Ser Arg Met
545                 550                 555                 560

Gly Val Pro Pro Glu Glu Pro Ser Gln Thr Gln Leu Ala Thr Thr Ser
            565                 570                 575

Ser Thr Ser Ala His Ser Leu Gln Thr Tyr Tyr Ile Pro Pro Glu Ala
        580                 585                 590

Glu Gly Phe Pro Asn Thr Ile
        595

<210> SEQ ID NO 7
<211> LENGTH: 311
<212> TYPE: PRT
<213> ORGANISM: Renilla reniformis

<400> SEQUENCE: 7

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310

<210> SEQ ID NO 8
<211> LENGTH: 311
<212> TYPE: PRT
<213> ORGANISM: Renilla reniformis

<400> SEQUENCE: 8

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

```
Pro His Ile Glu Pro Val Ala Arg Cys Ile Ile Pro Asp Leu Ile Gly
 65                  70                  75                  80

Met Gly Lys Ser Gly Lys Ser Gly Asn Gly Ser Tyr Arg Leu Leu Asp
             85                  90                  95

His Tyr Lys Tyr Leu Thr Ala Trp Phe Glu Leu Leu Asn Leu Pro Lys
        100                 105                 110

Lys Ile Ile Phe Val Gly His Asp Trp Gly Ala Ala Leu Ala Phe His
    115                 120                 125

Tyr Ser Tyr Glu His Gln Asp Lys Ile Lys Ala Ile Val His Ala Glu
130                 135                 140

Ser Val Val Asp Val Ile Glu Ser Trp Asp Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310

<210> SEQ ID NO 9
<211> LENGTH: 311
<212> TYPE: PRT
<213> ORGANISM: Renilla reniformis

<400> SEQUENCE: 9

Met Ala Ser Lys Val Tyr Asp Pro Glu Gln Arg Lys Arg Met Ile Thr
  1               5                  10                  15

Gly Pro Gln Trp Trp Ala Arg Cys Lys Gln Met Asn Val Leu Asp Ser
             20                  25                  30

Phe Ile Asn Tyr Tyr Asp Ser Glu Lys His Ala Glu Asn Ala Val Ile
         35                  40                  45

Phe Leu His Gly Asn Ala Thr Ser Ser Tyr Leu Trp Arg His Val Val
     50                  55                  60

Pro His Ile Glu Pro Val Ala Arg Cys Ile Ile Pro Asp Leu Ile Gly
 65                  70                  75                  80

Met Gly Lys Ser Gly Lys Ser Gly Asn Gly Ser Tyr Arg Leu Leu Asp
             85                  90                  95

His Tyr Lys Tyr Leu Thr Ala Trp Phe Glu Leu Leu Asn Leu Pro Lys
        100                 105                 110

Lys Ile Ile Phe Val Gly His Asp Trp Gly Ala Ala Leu Ala Phe His
    115                 120                 125
```

```
Tyr Ala Tyr Glu His Gln Asp Arg Ile Lys Ala Ile Val His Met Glu
        130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Leu Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Leu Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310
```

<210> SEQ ID NO 10
<211> LENGTH: 1564
<212> TYPE: DNA
<213> ORGANISM: Photinus pyralis

<400> SEQUENCE: 10

```
gaagagatac gccctggttc ctggaacaat tgcttttaca gatgcacata tcgaggtgga     60
catcacttac gctgagtact tcgaaatgtc cgttcggttg gcagaagcta tgaaacgata    120
tgggctgaat acaaatcaca gaatcgtcgt atgcagtgaa aactctcttc aattctttat    180
gccggtgttg ggcgcgttat ttatcggagt tgcagttgcg cccgcgaacg acatttataa    240
tgaacgtgaa ttgctcaaca gtatgggcat ttcgcagcct accgtggtgt cgtttccaa     300
aaaggggttg caaaaaattt tgaacgtgca aaaaaagctc ccaatcatcc aaaaaattat    360
tatcatggat tctaaaacgg attaccaggg atttcagtcg atgtacacgt tcgtcacatc    420
tcatctacct cccggtttta atgaatacga ttttgtgcca gagtccttcg atagggacaa    480
gacaattgca ctgatcatga actcctctgg atctactggt ctgcctaaag gtgtcgctct    540
gcctcataga actgcctgcg tgagattctc gcatgccaga gatcctattt ttggcaatca    600
aatcattccg gatactgcga ttttaagtgt tgttccattc catcacggtt ttggaatgtt    660
tactacactc ggatatttga tatgtggatt tcgagtcgtc ttaatgtata gatttgaaga    720
agagctgttt ctgaggagcc ttcaggatta caagattcaa agtgcgctgc tggtgccaac    780
cctattctcc ttcttcgcca aaagcactct gattgacaaa tacgatttat ctaatttaca    840
cgaaattgct tctggtggcg ctcccctctc taaggaagtc ggggaagcgg ttgccaagag    900
gttccatctg ccaggtatca ggcaaggata tgggctcact gagactacat cagctattct    960
gattacaccc gagggggatg ataaaccggg cgcggtcggt aaagttgttc cattttttga   1020
agcgaaggtt gtggatctgg ataccgggaa aacgctgggc gttaatcaaa gaggcgaact   1080
```

```
gtgtgtgaga ggtcctatga ttatgtccgg ttatgtaaac aatccggaag cgaccaacgc   1140
cttgattgac aaggatggat ggctacattc tggagacata gcttactggg acgaagacga   1200
acacttcttc atcgttgacc gcctgaagtc tctgattaag tacaaaggct atcaggtggc   1260
tcccgctgaa ttggaatcca tcttgctcca acacccaac atcttcgacg caggtgtcgc    1320
aggtcttccc gacgatgacg ccggtgaact tcccgccgcc gttgttgttt tggagcacgg   1380
aaagacgatg acgaaaaag agatcgtgga ttacgtcgcc agtcaagtaa caaccgcgaa    1440
aaagttgcgc ggaggagttg tgtttgtgga cgaagtaccg aaaggtctta ccggaaaact   1500
cgacgcaaga aaaatcagag agatcctcat aaaggccaag aagggcggaa agatcgccgt   1560
gtaa                                                               1564
```

<210> SEQ ID NO 11
<211> LENGTH: 595
<212> TYPE: PRT
<213> ORGANISM: Homo sapiens

<400> SEQUENCE: 11

```
Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285
```

```
Ala Asn Leu Trp Pro Ser Pro Leu Met Ile Lys Arg Ser Lys Lys Asn
        290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
                340                 345                 350

Glu Leu Val His Met Ile Asn Trp Ala Lys Arg Val Pro Gly Phe Val
                355                 360                 365

Asp Leu Thr Leu His Asp Gln Val His Leu Leu Glu Cys Ala Trp Leu
        370                 375                 380

Glu Ile Leu Met Ile Gly Leu Val Trp Arg Ser Met Glu His Pro Val
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
                420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
                500                 505                 510

His Ile Arg His Met Ser Asn Lys Thr Met Glu His Leu Tyr Ser Met
        515                 520                 525

Lys Cys Lys Asn Val Val Pro Leu Tyr Asp Leu Leu Leu Glu Met Leu
530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
                580                 585                 590

Ala Thr Val
        595

<210> SEQ ID NO 12
<211> LENGTH: 315
<212> TYPE: PRT
<213> ORGANISM: Homo sapiens

<400> SEQUENCE: 12

Gly Ser Ala Gly Asp Met Arg Ala Ala Asn Leu Trp Pro Ser Pro Leu
1               5                   10                  15

Met Ile Lys Arg Ser Lys Lys Asn Ser Leu Ala Leu Ser Leu Thr Ala
                20                  25                  30

Asp Gln Met Val Ser Ala Leu Leu Asp Ala Glu Pro Pro Ile Leu Tyr
                35                  40                  45

Ser Glu Tyr Asp Pro Thr Arg Pro Phe Ser Glu Ala Ser Met Met Gly
        50                  55                  60
```

Leu Leu Thr Asn Leu Ala Asp Arg Glu Leu Val His Met Ile Asn Trp
 65                  70                  75                  80

Ala Lys Arg Val Pro Gly Phe Val Asp Leu Thr Leu His Asp Gln Val
                 85                  90                  95

His Leu Leu Glu Cys Ala Trp Leu Glu Ile Leu Met Ile Gly Leu Val
            100                 105                 110

Trp Arg Ser Met Glu His Pro Val Lys Leu Leu Phe Ala Pro Asn Leu
        115                 120                 125

Leu Leu Asp Arg Asn Gln Gly Lys Cys Val Glu Gly Met Val Glu Ile
130                 135                 140

Phe Asp Met Leu Leu Ala Thr Ser Ser Arg Phe Arg Met Met Asn Leu
145                 150                 155                 160

Gln Gly Glu Glu Phe Val Cys Leu Lys Ser Ile Ile Leu Leu Asn Ser
                165                 170                 175

Gly Val Tyr Thr Phe Leu Ser Ser Thr Leu Lys Ser Leu Glu Glu Lys
            180                 185                 190

Asp His Ile His Arg Val Leu Asp Lys Ile Thr Asp Thr Leu Ile His
        195                 200                 205

Leu Met Ala Lys Ala Gly Leu Thr Leu Gln Gln Gln His Gln Arg Leu
210                 215                 220

Ala Gln Leu Leu Leu Ile Leu Ser His Ile Arg His Met Ser Asn Lys
225                 230                 235                 240

Thr Met Glu His Leu Tyr Ser Met Lys Cys Lys Asn Val Val Pro Leu
                245                 250                 255

Tyr Asp Leu Leu Leu Glu Met Leu Asp Ala His Arg Leu His Ala Pro
            260                 265                 270

Thr Ser Arg Gly Gly Ala Ser Val Glu Glu Thr Asp Gln Ser His Leu
        275                 280                 285

Ala Thr Ala Gly Ser Thr Ser Ser His Ser Leu Gln Lys Tyr Tyr Ile
290                 295                 300

Thr Gly Glu Ala Glu Gly Phe Pro Ala Thr Val
305                 310                 315

<210> SEQ ID NO 13
<211> LENGTH: 315
<212> TYPE: PRT
<213> ORGANISM: Homo sapiens

<400> SEQUENCE: 13

Gly Ser Ala Gly Asp Met Arg Ala Ala Asn Leu Trp Pro Ser Pro Leu
1               5                   10                  15

Met Ile Lys Arg Ser Lys Lys Asn Ser Leu Ala Leu Ser Leu Thr Ala
            20                  25                  30

Asp Gln Met Val Ser Ala Leu Leu Asp Ala Glu Pro Pro Ile Leu Tyr
        35                  40                  45

Ser Glu Tyr Asp Pro Thr Arg Pro Phe Ser Glu Ala Ser Met Met Gly
    50                  55                  60

Leu Leu Thr Asn Leu Ala Asp Arg Glu Leu Val His Met Ile Asn Trp
 65                 70                  75                  80

Ala Lys Arg Val Pro Gly Phe Val Asp Leu Thr Leu His Asp Gln Val
                85                  90                  95

His Leu Leu Glu Cys Ala Trp Leu Glu Ile Leu Met Ile Gly Leu Val
            100                 105                 110

Trp Arg Ser Met Glu His Pro Val Lys Leu Leu Phe Ala Pro Asn Leu
        115                 120                 125

```
Leu Leu Asp Arg Asn Gln Gly Lys Cys Val Glu Gly Met Val Glu Ile
            130                 135                 140

Phe Asp Met Leu Leu Ala Thr Ser Ser Arg Phe Arg Met Met Asn Leu
145                 150                 155                 160

Gln Gly Glu Glu Phe Val Cys Leu Lys Ser Ile Ile Leu Leu Asn Ser
                165                 170                 175

Gly Val Tyr Thr Phe Leu Ser Ser Thr Leu Lys Ser Leu Glu Glu Lys
                180                 185                 190

Asp His Ile His Arg Val Leu Asp Lys Ile Thr Asp Thr Leu Ile His
                195                 200                 205

Leu Met Ala Lys Ala Gly Leu Thr Leu Gln Gln Gln His Gln Arg Leu
            210                 215                 220

Ala Gln Leu Leu Leu Ile Leu Ser His Ile Arg His Met Ser Asn Lys
225                 230                 235                 240

Arg Met Glu His Leu Tyr Ser Met Lys Cys Lys Asn Val Val Pro Leu
                245                 250                 255

Tyr Asp Leu Leu Leu Glu Met Leu Asp Ala His Arg Leu His Ala Pro
                260                 265                 270

Thr Ser Arg Gly Gly Ala Ser Val Glu Glu Thr Asp Gln Ser His Leu
            275                 280                 285

Ala Thr Ala Gly Ser Thr Ser Ser His Ser Leu Gln Lys Tyr Tyr Ile
290                 295                 300

Thr Gly Glu Ala Glu Gly Phe Pro Ala Thr Val
305                 310                 315

<210> SEQ ID NO 14
<211> LENGTH: 315
<212> TYPE: PRT
<213> ORGANISM: Homo sapiens

<400> SEQUENCE: 14

Gly Ser Ala Gly Asp Met Arg Ala Ala Asn Leu Trp Pro Ser Pro Leu
1               5                   10                  15

Met Ile Lys Arg Ser Lys Lys Asn Ser Leu Ala Leu Ser Leu Thr Ala
            20                  25                  30

Asp Gln Met Val Ser Ala Leu Leu Asp Ala Glu Pro Pro Ile Leu Tyr
        35                  40                  45

Ser Glu Tyr Asp Pro Thr Arg Pro Phe Ser Glu Ala Ser Met Met Gly
    50                  55                  60

Leu Leu Thr Asn Leu Ala Asp Arg Glu Leu Val His Met Ile Asn Trp
65                  70                  75                  80

Ala Lys Arg Val Pro Gly Phe Val Asp Leu Thr Leu His Asp Gln Val
                85                  90                  95

His Leu Leu Glu Cys Ala Trp Leu Glu Ile Leu Met Ile Gly Leu Val
            100                 105                 110

Trp Arg Ser Met Glu His Pro Val Lys Leu Leu Phe Ala Pro Asn Leu
        115                 120                 125

Leu Leu Asp Arg Asn Gln Gly Lys Cys Val Glu Gly Met Val Glu Ile
    130                 135                 140

Phe Asp Met Leu Leu Ala Thr Ser Ser Arg Phe Arg Met Met Asn Leu
145                 150                 155                 160

Gln Gly Glu Glu Phe Val Cys Leu Lys Ser Ile Ile Leu Leu Asn Ser
                165                 170                 175

Gly Val Tyr Thr Phe Leu Ser Ser Thr Leu Lys Ser Leu Glu Glu Lys
                180                 185                 190
```

```
Asp His Ile His Arg Val Leu Asp Lys Ile Thr Asp Thr Leu Ile His
        195                 200                 205

Leu Met Ala Lys Ala Gly Leu Thr Leu Gln Gln His Gln Arg Leu
210                 215                 220

Ala Gln Leu Leu Leu Ile Leu Ser His Ile Arg His Met Ser Asn Lys
225                 230                 235                 240

Val Met Glu His Leu Tyr Ser Met Lys Cys Lys Asn Val Val Pro Leu
                245                 250                 255

Tyr Asp Leu Leu Leu Glu Met Leu Asp Ala His Arg Leu His Ala Pro
            260                 265                 270

Thr Ser Arg Gly Gly Ala Ser Val Glu Thr Asp Gln Ser His Leu
275                 280                 285

Ala Thr Ala Gly Ser Thr Ser Ser His Ser Leu Gln Lys Tyr Tyr Ile
290                 295                 300

Thr Gly Glu Ala Glu Gly Phe Pro Ala Thr Val
305                 310                 315

<210> SEQ ID NO 15
<211> LENGTH: 10
<212> TYPE: PRT
<213> ORGANISM: Artificial Sequence
<220> FEATURE:
<223> OTHER INFORMATION: Chemically synthesized

<400> SEQUENCE: 15

Gly Gly Gly Gly Ser Gly Gly Gly Gly Ser
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Chemically synthesized

<400> SEQUENCE: 16

Gly Gly Gly Gly Ser Gly Gly Gly Gly Ser Gly Gly Gly Gly Ser
1               5                   10                  15

<210> SEQ ID NO 17
<211> LENGTH: 550
<212> TYPE: PRT
<213> ORGANISM: Photinus pyralis

<400> SEQUENCE: 17

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
                20                  25                  30

Tyr Ala Leu Val Pro Gly Thr Ile Ala Phe Thr Asp Ala His Ile Glu
            35                  40                  45

Val Asp Ile Thr Tyr Ala Glu Tyr Phe Glu Met Ser Val Arg Leu Ala
        50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
```

```
            115                 120                 125
Ser Lys Lys Gly Leu Gln Lys Ile Leu Asn Val Gln Lys Lys Leu Pro
            130                 135                 140
Ile Ile Gln Lys Ile Ile Ile Met Asp Ser Lys Thr Asp Tyr Gln Gly
145                 150                 155                 160
Phe Gln Ser Met Tyr Thr Phe Val Thr Ser His Leu Pro Pro Gly Phe
                165                 170                 175
Asn Glu Tyr Asp Phe Val Pro Glu Ser Phe Asp Arg Asp Lys Thr Ile
                180                 185                 190
Ala Leu Ile Met Asn Ser Ser Gly Ser Thr Gly Leu Pro Lys Gly Val
                195                 200                 205
Ala Leu Pro His Arg Thr Ala Cys Val Arg Phe Ser His Ala Arg Asp
            210                 215                 220
Pro Ile Phe Gly Asn Gln Ile Ile Pro Asp Thr Ala Ile Leu Ser Val
225                 230                 235                 240
Val Pro Phe His His Gly Phe Gly Met Phe Thr Thr Leu Gly Tyr Leu
                245                 250                 255
Ile Cys Gly Phe Arg Val Val Leu Met Tyr Arg Phe Glu Glu Glu Leu
                260                 265                 270
Phe Leu Arg Ser Leu Gln Asp Tyr Lys Ile Gln Ser Ala Leu Leu Val
            275                 280                 285
Pro Thr Leu Phe Ser Phe Phe Ala Lys Ser Thr Leu Ile Asp Lys Tyr
            290                 295                 300
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
                340                 345                 350
Pro Glu Gly Asp Asp Lys Pro Gly Ala Val Gly Lys Val Val Pro Phe
            355                 360                 365
Phe Glu Ala Lys Val Val Asp Leu Asp Thr Gly Lys Thr Leu Gly Val
            370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
Trp Leu His Ser Gly Asp Ile Ala Tyr Trp Asp Glu Asp Glu His Phe
                420                 425                 430
Phe Ile Val Asp Arg Leu Lys Ser Leu Ile Lys Tyr Lys Gly Tyr Gln
                435                 440                 445
Val Ala Pro Ala Glu Leu Glu Ser Ile Leu Leu Gln His Pro Asn Ile
            450                 455                 460
Phe Asp Ala Gly Val Ala Gly Leu Pro Asp Asp Ala Gly Glu Leu
465                 470                 475                 480
Pro Ala Ala Val Val Val Leu Glu His Gly Lys Thr Met Thr Glu Lys
                485                 490                 495
Glu Ile Val Asp Tyr Val Ala Ser Gln Val Thr Thr Ala Lys Lys Leu
                500                 505                 510
Arg Gly Gly Val Val Phe Val Asp Glu Val Pro Lys Gly Leu Thr Gly
            515                 520                 525
Lys Leu Asp Ala Arg Lys Ile Arg Glu Ile Leu Ile Lys Ala Lys Lys
            530                 535                 540
```

Gly Gly Lys Ile Ala Val
545             550

<210> SEQ ID NO 18
<211> LENGTH: 1428
<212> TYPE: DNA
<213> ORGANISM: Photinus pyralis

<400> SEQUENCE: 18

| | | | | | |
|---|---|---|---|---|---|
| atggaagacg | ccaaaaacat | aaagaaaggc | ccggcgccat | tctatcctct | agaggatgga | 60 |
| accgctggag | agcaactgca | taaggctatg | aagagatacg | ccctggttcc | tggaacaatt | 120 |
| gcttttacag | atgcacatat | cgaggtgaac | atcacgtacg | cggaatactt | cgaaatgtcc | 180 |
| gttcggttgg | cagaagctat | gaaacgatat | gggctgaata | caaatcacag | aatcgtcgta | 240 |
| tgcagtgaaa | actctcttca | attctttatg | ccggtgttgg | gcgcgttatt | tatcggagtt | 300 |
| gcagttgcgc | ccgcgaacga | catttataat | gaacgtgaat | tgctcaacag | tatgaacatt | 360 |
| tcgcagccta | ccgtagtgtt | tgtttccaaa | aagggggttgc | aaaaaatttt | gaacgtgcaa | 420 |
| aaaaaattac | caataatcca | gaaaattatt | atcatggatt | ctaaaacgga | ttaccaggga | 480 |
| tttcagtcga | tgtacacgtt | cgtcacatct | catctacctc | ccggttttaa | tgaatacgat | 540 |
| tttgtaccag | agtcctttga | tcgtgacaaa | acaattgcac | tgataatgaa | ttcctctgga | 600 |
| tctactgggt | tacctaaggg | tgtggcccctt | ccgcatagaa | ctgcctgcgt | cagattctcg | 660 |
| catgccagag | atcctatttt | tggcaatcaa | atcgctccgg | atactgcgat | tttaagtgtt | 720 |
| gttccattcc | atcacggttt | tggaatgttt | actacactcg | atatttgat | atgtggattt | 780 |
| cgagtcgtct | taatgtatag | atttgaagaa | gagctgtttt | tacgatccct | tcaggattac | 840 |
| aaaattcaaa | gtgcgttgct | agtaccaacc | ctatttttcat | tcctggccaa | aagcactctg | 900 |
| attgacaaat | acgatttatc | taatttacac | gaaattgctt | ctgggggcgc | acctctttcg | 960 |
| aaagaagtcg | gggaagcggt | tgcaaaacgc | ttccatcttc | cagggatacg | acaaggatat | 1020 |
| gggctcactg | agactacatc | agctattctg | attacaccca | agggggatga | taaaccgggc | 1080 |
| gcggtcggta | agttgttcc | atttttttgaa | gcgaaggttg | tggatctgga | taccgggaaa | 1140 |
| acgctgggcg | ttaatcagag | aggcgaatta | tgtgtcagag | gacctatgat | tatgtccggt | 1200 |
| tatgtaaaca | atccggaagc | gaccaacgcc | ttgattgaca | aggatggatg | gctacattct | 1260 |
| ggagacatag | cttactggga | cgaagacgaa | cacttcttca | tagttgaccg | cttgaagtct | 1320 |
| ttaattaaat | acaaaggata | tcaggtggcc | cccgctgaat | tggaatcgat | attgttacaa | 1380 |
| cacccccaaca | tcttcgacgc | gggcgtggca | ggtcttcccg | acgattaa | | 1428 |

<210> SEQ ID NO 19
<211> LENGTH: 475
<212> TYPE: PRT
<213> ORGANISM: Photinus pyralis

<400> SEQUENCE: 19

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val

```
              65                  70                  75                  80
Cys Ser Glu Asn Ser Leu Gln Phe Phe Met Pro Val Leu Gly Ala Leu
                 85                  90                  95
Phe Ile Gly Val Ala Val Ala Pro Ala Asn Asp Ile Tyr Asn Glu Arg
                100                 105                 110
Glu Leu Leu Asn Ser Met Gly Ile Ser Gln Pro Thr Val Val Phe Val
                115                 120                 125
Ser Lys Lys Gly Leu Gln Lys Ile Leu Asn Val Gln Lys Lys Leu Pro
            130                 135                 140
Ile Ile Gln Lys Ile Ile Ile Met Asp Ser Lys Thr Asp Tyr Gln Gly
145                 150                 155                 160
Phe Gln Ser Met Tyr Thr Phe Val Thr Ser His Leu Pro Pro Gly Phe
                165                 170                 175
Asn Glu Tyr Asp Phe Val Pro Glu Ser Phe Asp Arg Asp Lys Thr Ile
                180                 185                 190
Ala Leu Ile Met Asn Ser Ser Gly Ser Thr Gly Leu Pro Lys Gly Val
                195                 200                 205
Ala Leu Pro His Arg Thr Ala Cys Val Arg Phe Ser His Ala Arg Asp
            210                 215                 220
Pro Ile Phe Gly Asn Gln Ile Ile Pro Asp Thr Ala Ile Leu Ser Val
225                 230                 235                 240
Val Pro Phe His His Gly Phe Gly Met Phe Thr Thr Leu Gly Tyr Leu
                245                 250                 255
Ile Cys Gly Phe Arg Val Val Leu Met Tyr Arg Phe Glu Glu Glu Leu
                260                 265                 270
Phe Leu Arg Ser Leu Gln Asp Tyr Lys Ile Gln Ser Ala Leu Leu Val
            275                 280                 285
Pro Thr Leu Phe Ser Phe Phe Ala Lys Ser Thr Leu Ile Asp Lys Tyr
        290                 295                 300
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
                340                 345                 350
Pro Glu Gly Asp Asp Lys Pro Gly Ala Val Gly Lys Val Val Pro Phe
            355                 360                 365
Phe Glu Ala Lys Val Val Asp Leu Asp Thr Gly Lys Thr Leu Gly Val
        370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
Trp Leu His Ser Gly Asp Ile Ala Tyr Trp Asp Glu Asp Glu His Phe
                420                 425                 430
Phe Ile Val Asp Arg Leu Lys Ser Leu Ile Lys Tyr Lys Gly Tyr Gln
            435                 440                 445
Val Ala Pro Ala Glu Leu Glu Ser Ile Leu Leu Gln His Pro Asn Ile
        450                 455                 460
Phe Asp Ala Gly Val Ala Gly Leu Pro Asp Asp
465                 470                 475

<210> SEQ ID NO 20
<211> LENGTH: 861
```

```
<212> TYPE: DNA
<213> ORGANISM: Photinus pyralis

<400> SEQUENCE: 20
atgtatagat tgaagaaga gctgtttctg aggagccttc aggattacaa gattcaaagt      60
gcgctgctgg tgccaaccct attctccttc ttcgccaaaa gcactctgat tgacaaatac    120
gatttatcta atttacacga aattgcttct ggtggcgctc ccctctctaa ggaagtcggg    180
gaagcggttg ccaagaggtt ccatctgcca ggtatcaggc aaggatatgg gctcactgag    240
actacatcag ctattctgat tacacccgag ggggatgata aaccgggcgc ggtcggtaaa    300
gttgttccat tttttgaagc gaaggttgtg gatctggata ccgggaaaac gctgggcgtt    360
aatcaaagag gcgaactgtg tgtgagaggt cctatgatta tgtccggtta tgtaaacaat    420
ccggaagcga ccaacgcctt gattgacaag gatggatggc tacattctgg agacatagct    480
tactgggacg aagacgaaca cttcttcatc gttgaccgcc tgaagtctct gattaagtac    540
aaaggctatc aggtggctcc cgctgaattg gaatccatct tgctccaaca ccccaacatc    600
ttcgacgcag gtgtcgcagg tcttcccgac gatgacgccg gtgaacttcc gccgccgtt     660 gttgttttgg agcacggaaa gacgatgacg gaaaaagaga tcgtggatta cgtcgccagt    720
caagtaacaa ccgcgaaaaa gttgcgcgga ggagttgtgt ttgtggacga agtaccgaaa    780
ggtcttaccg gaaaactcga cgcaagaaaa atcagagaga tcctcataaa ggccaagaag    840
ggcggaaaga tcgccgtgta a                                              861

<210> SEQ ID NO 21
<211> LENGTH: 286
<212> TYPE: PRT
<213> ORGANISM: Photinus pyralis

<400> SEQUENCE: 21

Met Tyr Arg Phe Glu Glu Glu Leu Phe Leu Arg Ser Leu Gln Asp Tyr
1               5                   10                  15

Lys Ile Gln Ser Ala Leu Leu Val Pro Thr Leu Phe Ser Phe Phe Ala
            20                  25                  30

Lys Ser Thr Leu Ile Asp Lys Tyr Asp Leu Ser Asn Leu His Glu Ile
        35                  40                  45

Ala Ser Gly Gly Ala Pro Leu Ser Lys Glu Val Gly Glu Ala Val Ala
    50                  55                  60

Lys Arg Phe His Leu Pro Gly Ile Arg Gln Gly Tyr Gly Leu Thr Glu
65                  70                  75                  80

Thr Thr Ser Ala Ile Leu Ile Thr Pro Glu Gly Asp Asp Lys Pro Gly
                85                  90                  95

Ala Val Gly Lys Val Val Pro Phe Phe Glu Ala Lys Val Val Asp Leu
            100                 105                 110

Asp Thr Gly Lys Thr Leu Gly Val Asn Gln Arg Gly Glu Leu Cys Val
        115                 120                 125

Arg Gly Pro Met Ile Met Ser Gly Tyr Val Asn Asn Pro Glu Ala Thr
    130                 135                 140

Asn Ala Leu Ile Asp Lys Asp Gly Trp Leu His Ser Gly Asp Ile Ala
145                 150                 155                 160

Tyr Trp Asp Glu Asp Glu His Phe Phe Ile Val Asp Arg Leu Lys Ser
                165                 170                 175

Leu Ile Lys Tyr Lys Gly Tyr Gln Val Ala Pro Ala Glu Leu Glu Ser
            180                 185                 190

Ile Leu Leu Gln His Pro Asn Ile Phe Asp Ala Gly Val Ala Gly Leu
```

```
                      195                 200                     205
Pro Asp Asp Ala Gly Glu Leu Pro Ala Ala Val Val Leu Glu
    210                 215                 220

His Gly Lys Thr Met Thr Glu Lys Glu Ile Val Asp Tyr Val Ala Ser
225                 230                 235                 240

Gln Val Thr Thr Ala Lys Lys Leu Arg Gly Val Val Phe Val Asp
                245                 250                 255

Glu Val Pro Lys Gly Leu Thr Gly Lys Leu Asp Ala Arg Lys Ile Arg
            260                 265                 270

Glu Ile Leu Ile Lys Ala Lys Lys Gly Lys Ile Ala Val
            275                 280                 285

<210> SEQ ID NO 22
<211> LENGTH: 1194
<212> TYPE: PRT
<213> ORGANISM: Photinus pyralis

<400> SEQUENCE: 22

Ala Thr Gly Gly Ala Ala Gly Ala Cys Gly Cys Ala Ala Ala
1               5                   10                  15

Ala Cys Ala Thr Ala Ala Ala Gly Ala Ala Ala Gly Gly Cys Cys Cys
                20                  25                  30

Gly Gly Cys Gly Cys Cys Ala Thr Thr Cys Thr Ala Thr Cys Cys Gly
            35                  40                  45

Cys Thr Gly Gly Ala Ala Gly Ala Thr Gly Gly Ala Ala Cys Cys Gly
            50                  55                  60

Cys Thr Gly Gly Ala Gly Ala Gly Cys Ala Ala Cys Thr Gly Cys Ala
65                  70                  75                  80

Thr Ala Ala Gly Gly Cys Thr Ala Thr Gly Ala Ala Gly Ala Gly Ala
                85                  90                  95

Thr Ala Cys Gly Cys Cys Cys Thr Gly Gly Thr Thr Cys Cys Thr Gly
                100                 105                 110

Gly Ala Ala Cys Ala Ala Thr Thr Gly Cys Thr Thr Thr Thr Ala Cys
            115                 120                 125

Ala Gly Ala Thr Gly Cys Ala Cys Ala Thr Ala Thr Cys Gly Ala Gly
            130                 135                 140

Gly Thr Gly Gly Ala Cys Ala Thr Cys Ala Cys Thr Ala Cys Gly Cys
145                 150                 155                 160

Cys Thr Gly Ala Gly Thr Ala Cys Thr Thr Cys Gly Ala Ala Ala Thr
                165                 170                 175

Gly Thr Cys Cys Gly Thr Thr Cys Gly Gly Thr Thr Gly Gly Cys Ala
                180                 185                 190

Gly Ala Ala Gly Cys Thr Ala Thr Gly Ala Ala Ala Cys Gly Ala Thr
            195                 200                 205

Ala Thr Gly Gly Gly Cys Thr Gly Ala Ala Thr Ala Cys Ala Ala Ala
            210                 215                 220

Thr Cys Ala Cys Ala Gly Ala Ala Thr Cys Gly Thr Cys Gly Thr Ala
225                 230                 235                 240

Thr Gly Cys Ala Gly Thr Gly Ala Ala Ala Cys Thr Cys Thr Cys
                245                 250                 255

Thr Thr Cys Ala Ala Thr Thr Cys Thr Thr Thr Ala Thr Gly Cys Cys
                260                 265                 270

Gly Gly Thr Gly Thr Thr Gly Gly Cys Gly Cys Gly Thr Thr Ala
            275                 280                 285

Thr Thr Thr Ala Thr Cys Gly Gly Ala Gly Thr Thr Gly Cys Ala Gly
```

-continued

```
            290                 295                 300
Thr Thr Gly Cys Gly Cys Cys Gly Cys Gly Ala Ala Cys Gly Ala
305                 310                 315                 320
Cys Ala Thr Thr Thr Ala Thr Ala Ala Thr Gly Ala Ala Cys Gly Thr
                325                 330                 335
Gly Ala Ala Thr Thr Gly Cys Thr Cys Ala Ala Cys Ala Gly Thr Ala
                340                 345                 350
Thr Gly Gly Gly Cys Ala Thr Thr Thr Cys Gly Cys Ala Gly Cys Cys
                355                 360                 365
Thr Ala Cys Cys Gly Thr Gly Gly Thr Gly Thr Thr Cys Gly Thr Thr
370                 375                 380
Thr Cys Cys Ala Ala Ala Ala Gly Gly Gly Thr Thr Gly Cys
385                 390                 395                 400
Ala Ala Ala Ala Ala Ala Thr Thr Thr Thr Gly Ala Ala Cys Gly Thr
                405                 410                 415
Gly Cys Ala Ala Ala Ala Ala Ala Gly Cys Thr Cys Cys Ala
                420                 425                 430
Ala Thr Cys Ala Thr Cys Cys Ala Ala Ala Ala Ala Thr Thr Ala
    435                 440                 445
Thr Thr Ala Thr Cys Ala Thr Gly Gly Ala Thr Thr Cys Thr Ala Ala
450                 455                 460
Ala Ala Cys Gly Gly Ala Thr Thr Ala Cys Ala Gly Gly Gly Ala
465                 470                 475                 480
Thr Thr Thr Cys Ala Gly Thr Cys Gly Ala Thr Gly Thr Ala Cys Ala
                485                 490                 495
Cys Gly Thr Thr Cys Gly Thr Cys Ala Cys Ala Thr Cys Thr Cys Ala
                500                 505                 510
Thr Cys Thr Ala Cys Cys Thr Cys Cys Cys Gly Gly Thr Thr Thr Thr
    515                 520                 525
Ala Ala Thr Gly Ala Ala Thr Ala Cys Gly Ala Thr Thr Thr Thr Gly
                530                 535                 540
Thr Gly Cys Cys Ala Gly Ala Gly Thr Cys Cys Thr Thr Cys Gly Ala
545                 550                 555                 560
Thr Ala Gly Gly Gly Ala Cys Ala Ala Gly Ala Cys Ala Ala Thr Thr
                565                 570                 575
Gly Cys Ala Cys Thr Gly Ala Thr Cys Ala Thr Gly Ala Ala Cys Thr
                580                 585                 590
Cys Cys Thr Cys Thr Gly Gly Ala Thr Cys Thr Ala Cys Thr Gly Gly
    595                 600                 605
Thr Cys Thr Gly Cys Cys Thr Ala Ala Ala Gly Gly Thr Gly Thr Cys
610                 615                 620
Gly Cys Thr Cys Thr Gly Cys Cys Thr Cys Ala Thr Ala Gly Ala Ala
625                 630                 635                 640
Cys Thr Gly Cys Cys Thr Gly Cys Gly Thr Gly Ala Gly Ala Thr Thr
                645                 650                 655
Cys Thr Cys Gly Cys Ala Thr Gly Cys Cys Ala Gly Ala Gly Ala Thr
                660                 665                 670
Cys Cys Thr Ala Thr Thr Thr Thr Gly Gly Cys Ala Ala Thr Cys
    675                 680                 685
Ala Ala Ala Thr Cys Ala Thr Thr Cys Cys Gly Gly Ala Thr Ala Cys
                690                 695                 700
Thr Gly Cys Gly Ala Thr Thr Thr Thr Ala Ala Gly Thr Gly Thr Thr
705                 710                 715                 720
```

-continued

Gly Thr Thr Cys Cys Ala Thr Thr Cys Cys Ala Thr Cys Ala Cys Gly
725 730 735

Gly Thr Thr Thr Thr Gly Gly Ala Ala Thr Gly Thr Thr Thr Ala Cys
740 745 750

Thr Ala Cys Ala Cys Thr Cys Gly Gly Ala Thr Ala Thr Thr Thr Gly
755 760 765

Ala Thr Ala Thr Gly Thr Gly Gly Ala Thr Thr Thr Cys Gly Ala Gly
770 775 780

Thr Cys Gly Thr Cys Thr Thr Ala Ala Thr Gly Thr Ala Thr Ala Gly
785 790 795 800

Ala Thr Thr Thr Gly Ala Ala Gly Ala Ala Gly Ala Gly Cys Thr Gly
805 810 815

Thr Thr Thr Cys Thr Gly Ala Gly Gly Ala Gly Cys Cys Thr Thr Cys
820 825 830

Ala Gly Gly Ala Thr Thr Ala Cys Ala Ala Gly Ala Thr Thr Cys Ala
835 840 845

Ala Ala Gly Thr Gly Cys Gly Cys Thr Gly Cys Thr Gly Gly Thr Gly
850 855 860

Cys Cys Ala Ala Cys Cys Cys Thr Ala Thr Thr Cys Thr Cys Cys Thr
865 870 875 880

Thr Cys Thr Thr Cys Gly Cys Cys Ala Ala Ala Ala Gly Cys Ala Cys
885 890 895

Thr Cys Thr Gly Ala Thr Thr Gly Ala Cys Ala Ala Ala Thr Ala Cys
900 905 910

Gly Ala Thr Thr Thr Ala Thr Cys Thr Ala Ala Thr Thr Thr Ala Cys
915 920 925

Ala Cys Gly Ala Ala Ala Thr Thr Gly Cys Thr Thr Cys Thr Gly Gly
930 935 940

Thr Gly Gly Cys Gly Cys Thr Cys Cys Cys Cys Thr Cys Thr Cys Thr
945 950 955 960

Ala Ala Gly Gly Ala Ala Gly Thr Cys Gly Gly Gly Gly Ala Ala Gly
965 970 975

Cys Gly Gly Thr Thr Gly Cys Cys Ala Ala Gly Ala Gly Gly Thr Thr
980 985 990

Cys Cys Ala Thr Cys Thr Gly Cys Cys Ala Gly Gly Thr Ala Thr Cys
995 1000 1005

Ala Gly Gly Cys Ala Ala Gly Gly Ala Thr Ala Thr Gly Gly Gly
1010 1015 1020

Cys Thr Cys Ala Cys Thr Gly Ala Gly Ala Cys Thr Ala Cys Ala
1025 1030 1035

Thr Cys Ala Gly Cys Thr Ala Thr Thr Cys Thr Gly Ala Thr Thr
1040 1045 1050

Ala Cys Ala Cys Cys Cys Gly Ala Gly Gly Gly Gly Gly Ala Thr
1055 1060 1065

Gly Ala Thr Ala Ala Ala Cys Cys Gly Gly Gly Cys Gly Cys Gly
1070 1075 1080

Gly Thr Cys Gly Gly Thr Ala Ala Ala Gly Thr Thr Gly Thr Thr
1085 1090 1095

Cys Cys Ala Thr Thr Thr Thr Thr Thr Gly Ala Ala Gly Cys Gly
1100 1105 1110

Ala Ala Gly Gly Thr Thr Gly Thr Gly Gly Ala Thr Cys Thr Gly
1115 1120 1125

Gly Ala Thr Ala Cys Cys Gly Gly Gly Ala Ala Ala Ala Cys Gly
1130 1135 1140

```
Cys Thr Gly Gly Gly Cys Gly Thr Thr Ala Ala Thr Cys Ala Ala
    1145                1150                1155

Ala Gly Ala Gly Gly Cys Gly Ala Ala Cys Thr Gly Thr Gly Thr
    1160                1165                1170

Gly Thr Gly Ala Gly Ala Gly Gly Thr Cys Cys Thr Ala Thr Gly
    1175                1180                1185

Ala Thr Thr Ala Thr Gly
    1190

<210> SEQ ID NO 23
<211> LENGTH: 398
<212> TYPE: PRT
<213> ORGANISM: Photinus pyralis

<400> SEQUENCE: 23

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320
```

```
Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
            355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met
385                 390                 395
```

<210> SEQ ID NO 24
<211> LENGTH: 459
<212> TYPE: DNA
<213> ORGANISM: Photinus pyralis

<400> SEQUENCE: 24

```
tccggttatg taaacaatcc ggaagcgacc aacgccttga ttgacaagga tggatggcta      60
cattctggag acatagctta ctgggacgaa gacgaacact tcttcatcgt tgaccgcctg     120
aagtctctga ttaagtacaa aggctatcag gtggctcccg ctgaattgga atccatcttg     180
ctccaacacc ccaacatctt cgacgcaggt gtcgcaggtc ttcccgacga tgacgccggt     240
gaacttcccg ccgccgttgt tgttttggag cacggaaaga cgatgacgga aaaagagatc     300
gtggattacg tcgccagtca agtaacaacc gcgaaaaagt tgcgcggagg agttgtgttt     360
gtggacgaag taccgaaagg tcttaccgga aaactcgacg caagaaaaat cagagagatc     420
ctcataaagg ccaagaaggg cggaaagatc gccgtgtaa                           459
```

<210> SEQ ID NO 25
<211> LENGTH: 153
<212> TYPE: PRT
<213> ORGANISM: Photinus pyralis

<400> SEQUENCE: 25

```
Met Ser Gly Tyr Val Asn Asn Pro Glu Ala Thr Asn Ala Leu Ile Asp
1               5                   10                  15

Lys Asp Gly Trp Leu His Ser Gly Asp Ile Ala Tyr Trp Asp Glu Asp
            20                  25                  30

Glu His Phe Phe Ile Val Asp Arg Leu Lys Ser Leu Ile Lys Tyr Lys
        35                  40                  45

Gly Tyr Gln Val Ala Pro Ala Glu Leu Glu Ser Ile Leu Leu Gln His
    50                  55                  60

Pro Asn Ile Phe Asp Ala Gly Val Ala Gly Leu Pro Asp Asp Ala
65                  70                  75                  80

Gly Glu Leu Pro Ala Ala Val Val Val Leu Glu His Gly Lys Thr Met
                85                  90                  95

Thr Glu Lys Glu Ile Val Asp Tyr Val Ala Ser Gln Val Thr Thr Ala
            100                 105                 110

Lys Lys Leu Arg Gly Gly Val Val Phe Val Asp Glu Val Pro Lys Gly
        115                 120                 125

Leu Thr Gly Lys Leu Asp Ala Arg Lys Ile Arg Glu Ile Leu Ile Lys
    130                 135                 140

Ala Lys Lys Gly Gly Lys Ile Ala Val
145                 150
```

<210> SEQ ID NO 26

-continued

```
<211> LENGTH: 471
<212> TYPE: DNA
<213> ORGANISM: Photinus pyralis

<400> SEQUENCE: 26
cctatgatta tgtccggtta tgtaaacaat ccggaagcga ccaacgcctt gattgacaag      60
gatggatggc tacattctgg agacatagct tactgggacg aagacgaaca cttcttcatc    120
gttgaccgcc tgaagtctct gattaagtac aaaggctatc aggtggctcc cgctgaattg    180
gaatccatct tgctccaaca ccccaacatc ttcgacgcag gtgtcgcagg tcttcccgac    240
gatgacgccg gtgaacttcc cgccgccgtt gttgttttgg agcacggaaa gacgatgacg    300
gaaaaagaga tcgtggatta cgtcgccagt caagtaacaa ccgcgaaaaa gttgcgcgga    360
ggagttgtgt ttgtggacga agtaccgaaa ggtcttaccg gaaaactcga cgcaagaaaa    420
atcagagaga tcctcataaa ggccaagaag ggcggaaaga tcgccgtgta a             471

<210> SEQ ID NO 27
<211> LENGTH: 157
<212> TYPE: PRT
<213> ORGANISM: Photinus pyralis

<400> SEQUENCE: 27

Gly Pro Met Ile Met Ser Gly Tyr Val Asn Asn Pro Glu Ala Thr Asn
1               5                   10                  15

Ala Leu Ile Asp Lys Asp Gly Trp Leu His Ser Gly Asp Ile Ala Tyr
            20                  25                  30

Trp Asp Glu Asp Glu His Phe Phe Ile Val Asp Arg Leu Lys Ser Leu
        35                  40                  45

Ile Lys Tyr Lys Gly Tyr Gln Val Ala Pro Ala Glu Leu Glu Ser Ile
    50                  55                  60

Leu Leu Gln His Pro Asn Ile Phe Asp Ala Gly Val Ala Gly Leu Pro
65                  70                  75                  80

Asp Asp Asp Ala Gly Glu Leu Pro Ala Ala Val Val Val Leu Glu His
                85                  90                  95

Gly Lys Thr Met Thr Glu Lys Glu Ile Val Asp Tyr Val Ala Ser Gln
            100                 105                 110

Val Thr Thr Ala Lys Lys Leu Arg Gly Gly Val Val Phe Val Asp Glu
        115                 120                 125

Val Pro Lys Gly Leu Thr Gly Lys Leu Asp Ala Arg Lys Ile Arg Glu
    130                 135                 140

Ile Leu Ile Lys Ala Lys Lys Gly Gly Lys Ile Ala Val
145                 150                 155

<210> SEQ ID NO 28
<211> LENGTH: 1629
<212> TYPE: DNA
<213> ORGANISM: Pyrophorus plagiophthalamus

<400> SEQUENCE: 28
atggtaaagc gtgagaaaaa tgtcatctat ggccctgagc tctccatcc tttggaggat      60 ttgactgccg gcgaaatgct gtttcgtgct ctccgcaagc actctcattt gcctcaagcc    120
ttggtcgatg tggtcggcga tgaatctttg agctacaagg agttttttga ggcaaccgtc    180
ttgctggctc agtccctcca caattgtggc tacaagatga cgacgtcgt tagtatctgt    240 gctgaaaaca ataccgtttt cttcattcca gtcatcgccg catggtatat cggtatgatc    300
gtggctccag tcaacgagag ctacattccc gacgaactgt gtaaagtcat gggtatctct    360
```

```
aagccacaga ttgtcttcac cactaagaat attctgaaca aagtcctgga agtccaaagc    420
cgcaccaact ttattaagcg tatcatcatc ttggacactg tggagaatat tcacggttgc    480
gaatctttgc ctaatttcat ctctcgctat tcagacggca acatcgcaaa ctttaaacca    540
ctccacttcg accctgtgga acaagttgca gccattctgt gtagcagcgg tactactgga    600
ctcccaaagg gagtcatgca gacccatcaa aacatttgcg tgcgtctgat ccatgctctc    660
gatccacgct acggcactca gctgattcct ggtgtcaccg tcttggtcta cttgcctttc    720
ttccatgctt tcggctttca tattactttg ggttacttta tggtcggtct ccgcgtgatt    780
atgttccgcc gttttgatca ggaggctttc ttgaaagcca tccaagatta tgaagtccgc    840
agtgtcatca acgtgcctag cgtgatcctg tttttgtcta agagcccact cgtggacaag    900
tacgacttgt cttcactgcg tgaattgtgt tgcggtgccg ctccactggc taaggaggtc    960
gctgaagtgg ccgccaaacg cttgaatctt ccagggattc gttgtggctt cggcctcacc   1020
gaatctacca gtgcgattat ccagactctc ggggatgagt ttaagagcgg ctctttgggc   1080
cgtgtcactc cactcatggc tgctaagatc gctgatcgcg aaactggtaa ggctttgggc   1140
ccgaaccaag tgggcgagct gtgtatcaaa ggccctatgg tgagcaaggg ttatgtcaat   1200
aacgttgaag ctaccaagga ggccatcgac gacgacggct ggttgcattc tggtgatttt   1260
ggatattacg acgaagatga gcattttac gtcgtggatc gttacaagga gctgatcaaa   1320
tacaagggta gccaggttgc tccagctgag ttggaggaga ttctgttgaa aaatccatgc   1380
attcgcgatg tcgctgtggt cggcattcct gatctgagg ccggcgaact gccttctgct   1440
ttcgttgtca agcagcctgg tacagaaatt accgccaaag aagtgtatga ttacctggct   1500
gaacgtgtga gccatactaa gtacttgcgt ggcggcgtgc gttttgttga ctccatccct   1560
cgtaacgtaa caggcaaaat tacccgcaag gagctgttga acaattgtt ggtgaaggcc   1620
ggcggttag                                                           1629

<210> SEQ ID NO 29
<211> LENGTH: 542
<212> TYPE: PRT
<213> ORGANISM: Pyrophorus plagiophthalamus

<400> SEQUENCE: 29

Met Val Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Gly Asp Glu
        35                  40                  45

Ser Leu Ser Tyr Lys Glu Phe Phe Glu Ala Thr Val Leu Leu Ala Gln
    50                  55                  60

Ser Leu His Asn Cys Gly Tyr Lys Met Asn Asp Val Val Ser Ile Cys
65                  70                  75                  80

Ala Glu Asn Asn Thr Arg Phe Phe Ile Pro Val Ile Ala Ala Trp Tyr
                85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
    130                 135                 140

Ile Lys Arg Ile Ile Ile Leu Asp Thr Val Glu Asn Ile His Gly Cys
```

```
            145                 150                 155                 160
Glu Ser Leu Pro Asn Phe Ile Ser Arg Tyr Ser Asp Gly Asn Ile Ala
                    165                 170                 175

Asn Phe Lys Pro Leu His Phe Asp Pro Val Glu Gln Val Ala Ala Ile
                180                 185                 190

Leu Cys Ser Ser Gly Thr Thr Gly Leu Pro Lys Gly Val Met Gln Thr
            195                 200                 205

His Gln Asn Ile Cys Val Arg Leu Ile His Ala Leu Asp Pro Arg Tyr
        210                 215                 220

Gly Thr Gln Leu Ile Pro Gly Val Thr Val Leu Val Tyr Leu Pro Phe
225                 230                 235                 240

Phe His Ala Phe Gly Phe His Ile Thr Leu Gly Tyr Phe Met Val Gly
                245                 250                 255

Leu Arg Val Ile Met Phe Arg Arg Phe Asp Gln Glu Ala Phe Leu Lys
                260                 265                 270

Ala Ile Gln Asp Tyr Glu Val Arg Ser Val Ile Asn Val Pro Ser Val
                275                 280                 285

Ile Leu Phe Leu Ser Lys Ser Pro Leu Val Asp Lys Tyr Asp Leu Ser
290                 295                 300

Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Arg Cys Gly
                325                 330                 335

Phe Gly Leu Thr Glu Ser Thr Ser Ala Ile Ile Gln Thr Leu Gly Asp
                340                 345                 350

Glu Phe Lys Ser Gly Ser Leu Gly Arg Val Thr Pro Leu Met Ala Ala
                355                 360                 365

Lys Ile Ala Asp Arg Glu Thr Gly Lys Ala Leu Gly Pro Asn Gln Val
                370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Gly Trp Leu His
                    405                 410                 415

Ser Gly Asp Phe Gly Tyr Tyr Asp Glu Asp Glu His Phe Tyr Val Val
                420                 425                 430

Asp Arg Tyr Lys Glu Leu Ile Lys Tyr Lys Gly Ser Gln Val Ala Pro
                435                 440                 445

Ala Glu Leu Glu Glu Ile Leu Leu Lys Asn Pro Cys Ile Arg Asp Val
450                 455                 460

Ala Val Val Gly Ile Pro Asp Leu Glu Ala Gly Glu Leu Pro Ser Ala
465                 470                 475                 480

Phe Val Val Lys Gln Pro Gly Thr Glu Ile Thr Ala Lys Glu Val Tyr
                485                 490                 495

Asp Tyr Leu Ala Glu Arg Val Ser His Thr Lys Tyr Leu Arg Gly Gly
                500                 505                 510

Val Arg Phe Val Asp Ser Ile Pro Arg Asn Val Thr Gly Lys Ile Thr
                515                 520                 525

Arg Lys Glu Leu Leu Lys Gln Leu Leu Val Lys Ala Gly Gly
530                 535                 540

<210> SEQ ID NO 30
<211> LENGTH: 558
<212> TYPE: DNA
<213> ORGANISM: Gaussia princeps
```

```
<400> SEQUENCE: 30
atgggagtga aagttctttt tgcccttatt tgtattgctg tggccgaggc caaaccaact      60
gaaaacaatg aagatttcaa cattgtagct gtagctagca actttgctac aacggatctc     120
gatgctgacc gtggtaaatt gcccggaaaa aaattaccac ttgaggtact caagaaaatg     180
gaagccaatg ctaggaaagc tggctgcact aggggatgtc tgatatgcct gtcacacatc     240
aagtgtacac ccaaaatgaa gaagtttatc ccaggaagat gccacaccta tgaaggagac     300
aaagaaagtg cacagggagg aataggagag ctattgttg acattcctga aattcctggg      360
tttaaggatt tggaacccat ggaacaattc attgcacaag ttgacctatg tgtagactgc     420
acaactggat gcctcaaagg tcttgccaat gtgcaatgtt ctgatttact caagaaatgg     480
ctgccacaaa gatgtgcaac ttttgctagc aaaattcaag gccaagtgga caaaataaag     540
ggtgccggtg gtgattaa                                                   558

<210> SEQ ID NO 31
<211> LENGTH: 185
<212> TYPE: PRT
<213> ORGANISM: Gaussia princeps

<400> SEQUENCE: 31

Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
    50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
    130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp
            180                 185

<210> SEQ ID NO 32
<211> LENGTH: 567
<212> TYPE: DNA
<213> ORGANISM: Aequorea victoria

<400> SEQUENCE: 32
atgcttacat cagacttcga caacccaaga tggattggac gacacaagca tatgttcaat      60
ttccttgatg tcaaccacaa tggaaaaatc tctcttgacg agatggtcta caggcatct     120 gatattgtca tcaataacct tggagcaaca cctgagcaag ccaaacgaca caagatgct     180
```

```
gtagaagcct tcttcggagg agctggaatg aaatatggtg tggaaactga ttggcctgca      240
tatattgaag gatggaaaaa attggctact gatgaattgg agaaatacgc caaaaacgaa      300
ccaacgctca tccgtatatg gggtgatgct ttgtttgata tcgttgacaa agatcaaaat      360
ggagccatta cactggatga atggaaagca taccaccaaag ctgctggtat catccaatca      420
tcagaagatt gcgaggaaac attcagagtg tgcgatattg atgaaagtgg acaactcgat      480
gttgatgaga tgacaagaca acatttagga ttttggtaca ccatggatcc tgcttgcgaa      540
aagctctacg gtggagctgt cccctaa                                          567
```

<210> SEQ ID NO 33
<211> LENGTH: 188
<212> TYPE: PRT
<213> ORGANISM: Aequorea victoria

<400> SEQUENCE: 33

```
Met Leu Thr Ser Asp Phe Asp Asn Pro Arg Trp Ile Gly Arg His Lys
1               5                   10                  15

His Met Phe Asn Phe Leu Asp Val Asn His Asn Gly Lys Ile Ser Leu
            20                  25                  30

Asp Glu Met Val Tyr Lys Ala Ser Asp Ile Val Ile Asn Asn Leu Gly
        35                  40                  45

Ala Thr Pro Glu Gln Ala Lys Arg His Lys Asp Ala Val Glu Ala Phe
    50                  55                  60

Phe Gly Gly Ala Gly Met Lys Tyr Gly Val Glu Thr Asp Trp Pro Ala
65                  70                  75                  80

Tyr Ile Glu Gly Trp Lys Lys Leu Ala Thr Asp Glu Leu Glu Lys Tyr
                85                  90                  95

Ala Lys Asn Glu Pro Thr Leu Ile Arg Ile Trp Gly Asp Ala Leu Phe
            100                 105                 110

Asp Ile Val Asp Lys Asp Gln Asn Gly Ala Ile Thr Leu Asp Glu Trp
        115                 120                 125

Lys Ala Tyr Thr Lys Ala Ala Gly Ile Ile Gln Ser Ser Glu Asp Cys
    130                 135                 140

Glu Glu Thr Phe Arg Val Cys Asp Ile Asp Glu Ser Gly Gln Leu Asp
145                 150                 155                 160

Val Asp Glu Met Thr Arg Gln His Leu Gly Phe Trp Tyr Thr Met Asp
                165                 170                 175

Pro Ala Cys Glu Lys Leu Tyr Gly Gly Ala Val Pro
            180                 185
```

<210> SEQ ID NO 34
<211> LENGTH: 691
<212> TYPE: DNA
<213> ORGANISM: Vibrio harveyi

<400> SEQUENCE: 34

```
atgaataaat ggaattacgg agtcttcttc gttaactttt ataataaagg ccaacaagag      60
ccatcaaaaa cgatgaataa tgcattagaa acattacgta ttattgatga agatacatct     120
atttatgatg tgattaatat tgatgaccac tatcttgtaa agaaagacag tgaagataaa     180
aagctagcgt cttttattac actaggagaa aaactatatg tgcttgctac cagtgaaaac     240
acagttgata ttgcagcgaa atatgcatta ccgttagttt tcaaatggga tgatataaat     300
gaggaacgac ttaaattgtt gagttttat aatgcatccg caagtaaata taacaagaat     360
atagatttgg ttcgacacca gcttatgtta catgtcaatg ttaatgaggc agaaactgta     420
```

```
gcaaaagaag aactcaaatt atatattgaa aactatgtag catgtacaca gcctagtaat    480
tttaatggct cgattgatag tattattcag agtaacgtga cagggagtta taaagactgt    540
ttgtcatatg tagcgaatct tgctggtaaa tttgataata ctgtggactt cttactttgt    600
tttgagtcaa tgcaagatca aaataagaaa aaatcagtaa tgatagatct taataatcaa    660
gttattaagt ccgccaaga  taataatcta a                                    691
```

<210> SEQ ID NO 35
<211> LENGTH: 231
<212> TYPE: PRT
<213> ORGANISM: Vibrio harveyi
<220> FEATURE:
<221> NAME/KEY: misc_feature
<222> LOCATION: (231)..(231)
<223> OTHER INFORMATION: Xaa can be any naturally occurring amino acid

<400> SEQUENCE: 35

```
Met Asn Lys Trp Asn Tyr Gly Val Phe Phe Val Asn Phe Tyr Asn Lys
1               5                   10                  15

Gly Gln Gln Glu Pro Ser Lys Thr Met Asn Asn Ala Leu Glu Thr Leu
            20                  25                  30

Arg Ile Ile Asp Glu Asp Thr Ser Ile Tyr Asp Val Ile Asn Ile Asp
        35                  40                  45

Asp His Tyr Leu Val Lys Lys Asp Ser Glu Asp Lys Lys Leu Ala Ser
    50                  55                  60

Phe Ile Thr Leu Gly Glu Lys Leu Tyr Val Leu Ala Thr Ser Glu Asn
65                  70                  75                  80

Thr Val Asp Ile Ala Ala Lys Tyr Ala Leu Pro Leu Val Phe Lys Trp
                85                  90                  95

Asp Asp Ile Asn Glu Glu Arg Leu Lys Leu Leu Ser Phe Tyr Asn Ala
            100                 105                 110

Ser Ala Ser Lys Tyr Asn Lys Asn Ile Asp Leu Val Arg His Gln Leu
        115                 120                 125

Met Leu His Val Asn Val Asn Glu Ala Glu Thr Val Ala Lys Glu Glu
    130                 135                 140

Leu Lys Leu Tyr Ile Glu Asn Tyr Val Ala Cys Thr Gln Pro Ser Asn
145                 150                 155                 160

Phe Asn Gly Ser Ile Asp Ser Ile Ile Gln Ser Asn Val Thr Gly Ser
                165                 170                 175

Tyr Lys Asp Cys Leu Ser Tyr Val Ala Asn Leu Ala Gly Lys Phe Asp
            180                 185                 190

Asn Thr Val Asp Phe Leu Leu Cys Phe Glu Ser Met Gln Asp Gln Asn
        195                 200                 205

Lys Lys Lys Ser Val Met Ile Asp Leu Asn Asn Gln Val Ile Lys Phe
    210                 215                 220

Arg Gln Asp Asn Asn Leu Xaa
225                 230
```

<210> SEQ ID NO 36
<211> LENGTH: 687
<212> TYPE: DNA
<213> ORGANISM: Renilla reniformis

<400> SEQUENCE: 36

```
atggcttcca aggtgtacga ccccgagcaa cgcaaacgca tgatcactgg gcctcagtgg    60
tgggctcgct gcaagcaaat gaacgtgctg gactccttca tcaactacta tgattccgag   120
aagcacgccg agaacgccgt gattttctg catggtaacg ctgcctccag ctacctgtgg   180
```

```
aggcacgtcg tgcctcacat cgagcccgtg gctagatgca tcatccctga tctgatcgga    240
atgggtaagt ccggcaagag cgggaatggc tcatatcgcc tcctggatca ctacaagtac    300
ctcaccgctt ggttcgagct gctgaacctt ccaaagaaaa tcatctttgt gggccacgac    360
tgggggcttt gtctggcctt tcactactcc tacgagcacc aagacaagat caaggccatc    420
gtccatgctg agagtgtcgt ggacgtgatc gagtcctggg acgagtggcc tgacatcgag    480
gaggatatcg ccctgatcaa gagcgaagag ggcgagaaaa tggtgcttga gaataacttc    540
ttcgtcgaga ccatgctccc aagcaagatc atgcggaaac tggagcctga ggagttcgct    600
gcctacctgg agccattcaa ggagaagggc gaggttagac ggcctaccct ctcctggcct    660
cgcgagatcc ctctcgttaa gggaggc                                        687
```

<210> SEQ ID NO 37
<211> LENGTH: 229
<212> TYPE: PRT
<213> ORGANISM: Renilla reniformis

<400> SEQUENCE: 37

```
Ala Ser Met Ala Ser Lys Val Tyr Asp Pro Glu Gln Arg Lys Arg Met
1               5                   10                  15

Ile Thr Gly Pro Gln Trp Trp Ala Arg Cys Lys Gln Met Asn Val Leu
            20                  25                  30

Asp Ser Phe Ile Asn Tyr Tyr Asp Ser Glu Lys His Ala Glu Asn Ala
        35                  40                  45

Val Ile Phe Leu His Gly Asn Ala Ala Ser Ser Tyr Leu Trp Arg His
    50                  55                  60

Val Val Pro His Ile Glu Pro Val Ala Arg Cys Ile Ile Pro Asp Leu
65                  70                  75                  80

Ile Gly Met Gly Lys Ser Gly Lys Ser Gly Asn Gly Ser Tyr Arg Leu
                85                  90                  95

Leu Asp His Tyr Lys Tyr Leu Thr Ala Trp Phe Glu Leu Leu Asn Leu
            100                 105                 110

Pro Lys Lys Ile Ile Phe Val Gly His Asp Trp Gly Ala Cys Leu Ala
        115                 120                 125

Phe His Tyr Ser Tyr Glu His Gln Asp Lys Ile Lys Ala Ile Val His
    130                 135                 140

Ala Glu Ser Val Val Asp Val Ile Glu Ser Trp Asp Glu Trp Pro Asp
145                 150                 155                 160

Ile Glu Glu Asp Ile Ala Leu Ile Lys Ser Glu Glu Gly Glu Lys Met
                165                 170                 175

Val Leu Glu Asn Asn Phe Phe Val Glu Thr Met Leu Pro Ser Lys Ile
            180                 185                 190

Met Arg Lys Leu Glu Pro Glu Glu Phe Ala Ala Tyr Leu Glu Pro Phe
        195                 200                 205

Lys Glu Lys Gly Glu Val Arg Arg Pro Thr Leu Ser Trp Pro Arg Glu
    210                 215                 220

Ile Pro Leu Val Lys
225
```

<210> SEQ ID NO 38
<211> LENGTH: 249
<212> TYPE: DNA
<213> ORGANISM: Renilla reniformis -continued

```
<400> SEQUENCE: 38
aagcccgacg tcgtccagat tgtccgcaac tacaacgcct accttcgggc cagcgacgat      60
ctgcctaaga tgttcatcga gtccgaccct gggttctttt ccaacgctat tgtcgaggga     120
gctaagaagt tccctaacac cgagttcgtg aaggtgaagg cctccacttc agccaggag     180 gacgctccag atgaaatggg taagtacatc aagagcttcg tggagcgcgt gctgaagaac     240
gagcagtaa                                                             249

<210> SEQ ID NO 39
<211> LENGTH: 82
<212> TYPE: PRT
<213> ORGANISM: Renilla reniformis

<400> SEQUENCE: 39

Lys Pro Asp Val Val Gln Ile Val Arg Asn Tyr Asn Ala Tyr Leu Arg
1               5                  10                  15

Ala Ser Asp Asp Leu Pro Lys Met Phe Ile Glu Ser Asp Pro Gly Phe
            20                  25                  30

Phe Ser Asn Ala Ile Val Glu Gly Ala Lys Lys Phe Pro Asn Thr Glu
        35                  40                  45

Phe Val Lys Val Lys Gly Leu His Phe Ser Gln Glu Asp Ala Pro Asp
    50                  55                  60

Glu Met Gly Lys Tyr Ile Lys Ser Phe Val Glu Arg Val Leu Lys Asn
65                  70                  75                  80

Glu Gln

<210> SEQ ID NO 40
<211> LENGTH: 550
<212> TYPE: PRT
<213> ORGANISM: Homo sapiens

<400> SEQUENCE: 40

Met Glu Asp Ala Lys Asn Ile Lys Lys Gly Pro Ala Pro Phe Tyr Pro
1               5                  10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190
```

```
Ala Leu Ile Met Asn Ser Ser Gly Ser Thr Gly Leu Pro Lys Gly Val
            195                 200                 205

Ala Leu Pro His Arg Thr Ala Cys Val Arg Phe Ser His Ala Arg Asp
        210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
    530                 535                 540

Gly Gly Lys Ile Ala Val
545                 550
```